United States Patent
Fukushima et al.

(10) Patent No.: US 10,869,465 B2
(45) Date of Patent: Dec. 22, 2020

(54) TRANSGENIC MOUSE MODEL OF RETINAL VASCULAR DISEASE, METHOD OF MAKING, AND METHOD OF USING

(71) Applicant: OSAKA UNIVERSITY, Osaka (JP)

(72) Inventors: Yoko Fukushima, Osaka (JP); Kohji Nishida, Osaka (JP); Toru Nakano, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 87 days.

(21) Appl. No.: 16/058,568

(22) Filed: Aug. 8, 2018

(65) Prior Publication Data

US 2019/0045759 A1 Feb. 14, 2019

(30) Foreign Application Priority Data

Aug. 10, 2017 (JP) ................. 2017-156031

(51) Int. Cl.
*A01K 67/027* (2006.01)
*C12N 15/00* (2006.01)
*G01N 33/00* (2006.01)
*A61K 49/00* (2006.01)
*C12N 9/12* (2006.01)

(52) U.S. Cl.
CPC ...... *A01K 67/0275* (2013.01); *A61K 49/0008* (2013.01); *C12N 9/12* (2013.01); *C12Y 207/11001* (2013.01); *A01K 2217/052* (2013.01); *A01K 2227/105* (2013.01); *A01K 2267/035* (2013.01)

(58) Field of Classification Search
USPC ........................................... 800/3, 8, 18, 21
See application file for complete search history.

(56) References Cited

U.S. PATENT DOCUMENTS

| | | | |
|---|---|---|---|
| 7,112,715 B2 * | 9/2006 | Chambon .......... | A01K 67/0276 800/18 |
| 2011/0191871 A1 * | 8/2011 | Walsh .............. | A61P 3/10 800/13 |

OTHER PUBLICATIONS

Egawa (J. Invest. Derm., 2009, vol. 129, p. 2386-2395).*
Ouyang (J. Immunol., 2019, vol. 202, p. 1441-1452).*
Littlewood (Nucleic acids Research, 1995, vol. 23, No. 10, p. 1686-1690).*
Ristevski (Mol. Biotech., 2005, vol. 29, p. 153-163).*
McCarthy (Mol. Cell. Biol., 1997, vol. 17, No. 5, p. 2401-2412).*
Zhang (Nucleic acids research, 1996, vol. 24, No. 4, p. 543-548).*
Condorelli (PNAS, 2002, vol. 99, No. 19, p. 12333-12338).*
Andersson (Transgenic Res., 2010, vol. 19, p. 715-725).*
Murayama (Oncogene, 2007, vol. 26, p. 4882-4888).*
Kita (Genes to Cells, 2008, vol. 13, p. 839-850).*
Kimura (Development, 2008, vol. 135, p. 869-879).*
Lois E. H. Smith et al., "Oxygen-Induced Retinopathy in the Mouse", Investigative Ophthalmology & Visual Science, vol. 35, No. 1, Jan. 1994, pp. 101-111.

* cited by examiner

*Primary Examiner* — Michael C Wilson
(74) *Attorney, Agent, or Firm* — Greenblum & Bernstein, P.L.C.

(57) ABSTRACT

Provided are a non-human model animal of a retinal vascular disease that can favorably show symptoms similar to those of human retinal vascular diseases such as human diabetic retinopathy, and a method for producing the non-human model animal. In particular, provided are a non-human model animal that is suitable for establishing a method for treating, preventing, or diagnosing retinal edema, which causes highly impaired vision, and a method for producing the non-human model animal. A method for screening a drug for treating and preventing a retinal vascular disease, the method using a non-human model animal, is provided. Provided are a non-human model animal of a retinal vascular disease in which constitutively active Akt is expressed, a method for producing a non-human model animal of a retinal vascular disease in which constitutively active Akt is expressed, and a method for screening a drug for treating or preventing a retinal vascular disease.

11 Claims, 16 Drawing Sheets

Specification includes a Sequence Listing.

SEQUENCE LISTING

<160> NUMBER OF SEQ ID NOS: 29

<210> SEQ ID NO 1
<211> LENGTH: 1116
<212> TYPE: DNA
<213> ORGANISM: Homo sapiens

<400> SEQUENCE: 1

```
ggatccacca tggggagtag caagagcaag cctaaggacc ccagccagcg cagcgaggct      60
gaagagatgg aggtgtccct ggccaagccc aagcaccgcg tgaccatgaa cgagtttgag     120
tacctgaagc tgctgggcaa gggcactttc ggcaaggtga tcctggtgaa ggagaaggcc     180
acaggccgct actacgccat gaagatcctc aagaaggaag tcatcgtggc caaggacgag     240
gtggcccaca cactcaccga gaaccgcgtc ctgcagaact ccaggcaccc cttcctcaca     300
gccctgaagt actctttcca gacccacgac cgcctctgct ttgtcatgga gtacgccaac     360
gggggcgagc tgttcttcca cctgtcccgg gaacgtgtgt tctccgagga ccgggcccgc     420
ttctatggcg ctgagattgt gtcagccctg gactacctgc actcggagaa gaacgtggtg     480
taccgggacc tcaagctgga gaacctcatg ctggacaagg acgggcacat taagatcaca     540
gacttcgggc tgtgcaagga ggggatcaag gacggtgcca ccatgaagac cttttgcggc     600
acacctgagt acctggcccc cgaggtgctg gaggacaatg actacggccg tgcagtggac     660
tggtgggggc tgggcgtggt catgtacgag atgatgtgcg gtcgcctgcc cttctacaac     720
caggaccatg agaagctttt tgagctcatc ctcatggagg agatccgctt cccgcgcacg     780
cttggtcccg aggccaagtc cttgctttca gggctgctca agaaggaccc caagcagagg    840
```

```
cttggcgggg gctccgagga cgccaaggag atcatgcagc atcgcttctt tgccggtatc    900
gtgtggcagc acgtgtacga gaagaagctc agcccaccct tcaagcccca ggtcacgtcg    960
gagactgaca ccaggtattt tgatgaggag ttcacggccc agatgatcac catcacacca   1020
cctgaccaag atgacagcat ggagtgtgtg gacagcgagc gcaggcccca cttccccag    1080 ttctcctact cggccagcag cacggcctga ggatcc                              1116
```

```
<210> SEQ ID NO 2
<211> LENGTH: 366
<212> TYPE: PRT
<213> ORGANISM: Homo sapiens

<400> SEQUENCE: 2
```

```
Met Gly Ser Ser Lys Ser Lys Pro Lys Asp Pro Ser Gln Arg Ser Glu
1               5                   10                  15

Ala Glu Glu Met Glu Val Ser Leu Ala Lys Pro Lys His Arg Val Thr
                20                  25                  30

Met Asn Glu Phe Glu Tyr Leu Lys Leu Leu Gly Lys Gly Thr Phe Gly
            35                  40                  45

Lys Val Ile Leu Val Lys Glu Lys Ala Thr Gly Arg Tyr Tyr Ala Met
    50                  55                  60

Lys Ile Leu Lys Lys Glu Val Ile Val Ala Lys Asp Glu Val Ala His
65                  70                  75                  80

Thr Leu Thr Glu Asn Arg Val Leu Gln Asn Ser Arg His Pro Phe Leu
                85                  90                  95

Thr Ala Leu Lys Tyr Ser Phe Gln Thr His Asp Arg Leu Cys Phe Val
            100                 105                 110

Met Glu Tyr Ala Asn Gly Gly Glu Leu Phe Phe His Leu Ser Arg Glu
        115                 120                 125

Arg Val Phe Ser Glu Asp Arg Ala Arg Phe Tyr Gly Ala Glu Ile Val
    130                 135                 140

Ser Ala Leu Asp Tyr Leu His Ser Glu Lys Asn Val Val Tyr Arg Asp
145                 150                 155                 160

Leu Lys Leu Glu Asn Leu Met Leu Asp Lys Asp Gly His Ile Lys Ile
                165                 170                 175

Thr Asp Phe Gly Leu Cys Lys Glu Gly Ile Lys Asp Gly Ala Thr Met
            180                 185                 190

Lys Thr Phe Cys Gly Thr Pro Glu Tyr Leu Ala Pro Glu Val Leu Glu
        195                 200                 205

Asp Asn Asp Tyr Gly Arg Ala Val Asp Trp Trp Gly Leu Gly Val Val
    210                 215                 220

Met Tyr Glu Met Met Cys Gly Arg Leu Pro Phe Tyr Asn Gln Asp His
225                 230                 235                 240

Glu Lys Leu Phe Glu Leu Ile Leu Met Glu Glu Ile Arg Phe Pro Arg
                245                 250                 255

Thr Leu Gly Pro Glu Ala Lys Ser Leu Leu Ser Gly Leu Leu Lys Lys
            260                 265                 270

Asp Pro Lys Gln Arg Leu Gly Gly Gly Ser Glu Asp Ala Lys Glu Ile
        275                 280                 285

Met Gln His Arg Phe Phe Ala Gly Ile Val Trp Gln His Val Tyr Glu
    290                 295                 300

Lys Lys Leu Ser Pro Pro Phe Lys Pro Gln Val Thr Ser Glu Thr Asp
305                 310                 315                 320
```

Thr Arg Tyr Phe Asp Glu Glu Phe Thr Ala Gln Met Ile Thr Ile Thr
            325                 330                 335

Pro Pro Asp Gln Asp Asp Ser Met Glu Cys Val Asp Ser Glu Arg Arg
            340                 345                 350

Pro His Phe Pro Gln Phe Ser Tyr Ser Ala Ser Ser Thr Ala
            355                 360                 365

<210> SEQ ID NO 3
<211> LENGTH: 6309
<212> TYPE: DNA
<213> ORGANISM: Homo sapiens
<220> FEATURE:
<221> NAME/KEY: modified_base
<222> LOCATION: (909)..(1008)
<223> OTHER INFORMATION: a, c, t, or g
<220> FEATURE:
<221> NAME/KEY: modified_base
<222> LOCATION: (1377)..(1476)
<223> OTHER INFORMATION: a, c, t, or g
<220> FEATURE:
<221> NAME/KEY: modified_base
<222> LOCATION: (1733)..(1832)
<223> OTHER INFORMATION: a, c, t, or g
<220> FEATURE:
<221> NAME/KEY: modified_base
<222> LOCATION: (2310)..(2409)
<223> OTHER INFORMATION: a, c, t, or g
<220> FEATURE:
<221> NAME/KEY: modified_base
<222> LOCATION: (2754)..(2853)
<223> OTHER INFORMATION: a, c, t, or g
<220> FEATURE:
<221> NAME/KEY: modified_base
<222> LOCATION: (3343)..(3442)
<223> OTHER INFORMATION: a, c, t, or g
<220> FEATURE:
<221> NAME/KEY: modified_base
<222> LOCATION: (3748)..(3847)
<223> OTHER INFORMATION: a, c, t, or g
<220> FEATURE:
<221> NAME/KEY: modified_base
<222> LOCATION: (4067)..(4166)
<223> OTHER INFORMATION: a, c, t, or g
<220> FEATURE:
<221> NAME/KEY: modified_base
<222> LOCATION: (4512)..(4611)
<223> OTHER INFORMATION: a, c, t, or g
<220> FEATURE:
<221> NAME/KEY: modified_base
<222> LOCATION: (5007)..(5106)
<223> OTHER INFORMATION: a, c, t, or g
<220> FEATURE:
<221> NAME/KEY: modified_base
<222> LOCATION: (5451)..(5550)
<223> OTHER INFORMATION: a, c, t, or g
<220> FEATURE:
<221> NAME/KEY: modified_base
<222> LOCATION: (5946)..(6045)
<223> OTHER INFORMATION: a, c, t, or g

<400> SEQUENCE: 3
cccacttact tgctgcctcc cgactgctgt aattatgggt ctgtaaccac cctggactgg      60
gtgctcctca ctgacggact tgtctgaacc tctctttgtc tccagcgccc agcactgggc     120
ctggcaaaac ctgagacgcc cggtacatgt tggccaaatg aatgaaccag attcagaccg     180 gcagggcgc tgtggtttag gagggggcctg gggtttctcc caggaggttt ttgggcttgc     240
gctggagggc tctggactcc cgtttgcgcc agtggcctgc atcctggtcc tgtcttcctc     300
atgtttgaat ttctttgctt tcctagtctg gggagcaggg aggagccctg tgccctgtcc     360
caggatccat gggtaggaac accatggaca gggagagcaa acggggccat ctgtcaccag     420

| | |
|---|---|
| gggcttaggg aaggccgagc cagcctgggt caaagaagtc aaaggggctg cctggaggag | 480 |
| gcagcctgtc agctggtgca tcaggttagg gaggctggga aggccttttg gggatgggggg | 540 |
| tgatttgtcc aacggctggg ggaggtggga atggggaggt gagcaaggca gcagctctca | 600 |
| gggcctggct gttgcgggtg gtggtggcag gggctgagg ctctaagcct agaataagga | 660 |
| gaggcccagg tccagggaac tgtgttcaat tacatggatt tgacacttgg cagccctgag | 720 |
| tgttttgggg agagggaagg caggcggca gatgggggtc agagagctta gagggatggc | 780 |
| agcccacctg ggaaggcagg tgcgggtgga gccccaggc acgtgcagtg ggtctctggc | 840 |
| tcacccaggg cgaggagctg cccttagcca ggcgtggcct cacattcagc ttcctttgct | 900 |
| tctcccagnn nnnnnnnnn nnnnnnnnn nnnnnnnnn nnnnnnnnn nnnnnnnnn | 960 |
| nnnnnnnnn nnnnnnnnn nnnnnnnnn nnnnnnnnn nnnnnnnngg gcagatgggg | 1020 |
| gtcagagagc ttagagggat ggcagcccac ctgggaaggc aggtgcgggt ggagccccca | 1080 |
| ggcacgtgca gtgggtctct ggctcaccca gggcgaggag ctgcccttag ccaggcgtgg | 1140 |
| cctcacattc agcttccttt gcttctccca gaggctgtgg ccaggccagc tgggctcggg | 1200 |
| gagcgccagc ctgagaggag cgcgtgagcg tcgcgggagc ctcgggcacc atgagcgacg | 1260 |
| tggctattgt gaaggagggt tggctgcaca acgaggtta gtacccgctg ccagggctgg | 1320 |
| gcctggggag ggagagacag gggtagtagc cccagggtct gtgagtgcct gtgcccnnnn | 1380 |
| nnnnnnnnn nnnnnnnnn nnnnnnnnn nnnnnnnnn nnnnnnnnn nnnnnnnnn | 1440 |
| nnnnnnnnn nnnnnnnnn nnnnnnnnn nnnnnntggc tgcctggcga aggtctgacg | 1500 |
| ggtagagtgt gcgtggctct caccacccgc acgtctgtag gggagtacat caagacctgg | 1560 |
| cggccacgct acttcctcct caagaatgat ggcaccttca ttggctacaa ggagcggccg | 1620 |
| caggatgtgg accaacgtga ggctcccctc aacaacttct ctgtggcgcg taagtatccc | 1680 |
| cttggcctct cgggattcag atttgggggg ttggctggag ccctctttgc ccnnnnnnnn | 1740 |
| nnnnnnnnn nnnnnnnnn nnnnnnnnn nnnnnnnnn nnnnnnnnn nnnnnnnnn | 1800 |
| nnnnnnnnn nnnnnnnnn nnnnnnnnn nngacgatgg tgggggtttg acctgacgcc | 1860 |
| gggccagatg ccctgtgtgg ctgcctcagc ctggagtaga gtgtctgagc tggaacaggg | 1920 |
| gtcctagccc cactctgtga ggcgagaaac tgaggcttgg agagaggaag agatggggct | 1980 |
| tcccaggacc tggtgggtgg tatgcaaggg gagctggctg gtgcagcggg ggctgtggtg | 2040 |
| agggccctgg gaggggcagg gggatgcacg cagacaaagg ctctgcctgc ccgcagagtg | 2100 |
| ccagctgatg aagacggagc ggccccggcc caacaccttc atcatccgct gcctgcagtg | 2160 |
| gaccactgtc atcgaacgca ccttccatgt ggagactcct gaggagcggt acgtgggctg | 2220 |
| tggcggccag gccaggcact tgggcagccc cagcgcttag gagggacacg gggatggcgg | 2280 |
| ggtgctggca cctctgcctg tagccatccn nnnnnnnnn nnnnnnnnn nnnnnnnnn | 2340 |
| nnnnnnnnn nnnnnnnnn nnnnnnnnn nnnnnnnnn nnnnnnnnn nnnnnnnnn | 2400 |
| nnnnnnnng cgggtgggtg aaagacgtgg ggtggagctc ctgatctggt acaggcctgc | 2460 |
| agcctcacct gacctcctgc agggaggagt ggacaaccgc catccagact gtggctgacg | 2520 |
| gcctcaagaa gcaggaggag gaggagatgg acttccggtc gggctcaccc agtgacaact | 2580 |
| caggggctga agagatggag gtgtccctgg ccaagcccaa gcaccgcgtg gtaggtgtcc | 2640 |
| ccacttctgc ctgtgcctgg ggctgccttg gactgtggag ggctgggtgg gtcatggggt | 2700 |
| cccagctcgg cccaggagac actcagcact ccacggcatc tccacctagg ccgnnnnnnn | 2760 |
| nnnnnnnnn nnnnnnnnn nnnnnnnnn nnnnnnnnn nnnnnnnnn nnnnnnnnn | 2820 |

-continued

```
nnnnnnnnnn nnnnnnnnnn nnnnnnnnnn nnngtgaagt ggacgcctct cctggctctg    2880
ccttcgactc tggggcccct catgccaccc cacgcatgcc gaccagctgg gcactgttgg    2940
cagcgccgct tgctgaccct ggtgcctgcc catagaccat gaacgagttt gagtacctga    3000
agctgctggg caagggcact ttcggcaagg tgatcctggt gaaggagaag ccacaggcc     3060 gctactacgc catgaagatc ctcaagaagg aagtcatcgt ggccaaggtg gggccggggc    3120
ggtggggcag ggtggagatg agggtgcggg gtggcagctc acccagccct gctttacagg    3180
acgaggtggc ccacacactc accgagaacc gcgtcctgca gaactccagg cacccctttcc   3240 tcacagtgag tgggagccca gatggggctg aagggctggg gccaggtagc gactcctggg    3300
gctgtctcta ggggacgatg tcctgtcttc ttgggcacgt gannnnnnnn nnnnnnnnnn    3360
nnnnnnnnnn nnnnnnnnnn nnnnnnnnnn nnnnnnnnnn nnnnnnnnnn nnnnnnnnnn    3420
nnnnnnnnnn nnnnnnnnnn nnggtatcag gcgacgtggt atcaagcagc gtggtgtcgg    3480
gcagcgtggt gcgggctgc cgtcctgcct gtggggccgc agttccagct ccccttcctt     3540
gcaggccctg aagtactctt tccagaccca cgaccgcctc tgctttgtca tggagtacgc    3600 caacggggc gaggtagggg ctggggctgc ggggatgga cttcgcggcc tgtggcccgc      3660
ccatggtggg gccggtcctt cccggagcct cggctactct ccatggcacc agacggtgct    3720
ccctgctggg tgggtggtgt gatgcctnnn nnnnnnnnn nnnnnnnnnn nnnnnnnnnn     3780
nnnnnnnnnn nnnnnnnnnn nnnnnnnnnn nnnnnnnnnn nnnnnnnnnn nnnnnnnnnn    3840
nnnnnnngct gtgcctcagg ttgcgcctcc cgcagctgtt cttccacctg tcccgggaac    3900
gtgtgttctc cgaggaccgg gcccgcttct atggcgctga gattgtgtca gccctggact    3960
acctgcactc ggagaagaac gtggtgtacc gggacctcaa ggtgcgctgg cgggcaggca    4020 gggggcagg gccctggggg cctggcggca ctgacctgag gccaccnnnn nnnnnnnnn     4080 nnnnnnnnnn nnnnnnnnnn nnnnnnnnnn nnnnnnnnnn nnnnnnnnnn nnnnnnnnnn    4140
nnnnnnnnnn nnnnnnnnnn nnnnnntggc gctgagattg tgtcagccct ggactacctg    4200
cactcggaga agaacgtggt gtaccgggac ctcaaggtgc gctggcgggc aggcaggggg    4260
gcagggccct gggggcctgg cggcactgac ctgaggccac ctttcccta gctggagaac    4320 ctcatgctgg acaaggacgg gcacattaag atcacagact tcgggctgtg caaggagggg    4380
atcaaggacg gtgccaccat gaagaccttt tgcggcacac tgagtacct ggcccccgag    4440 gtgtgcgccc cacctgcgtg catacgcgtt gctgcgtccc cacgtcctga gcacacgcaa    4500
tgctgtgtcc tnnnnnnnnn nnnnnnnnnn nnnnnnnnnn nnnnnnnnnn nnnnnnnnnn    4560
nnnnnnnnnn nnnnnnnnnn nnnnnnnnnn nnnnnnnnnn nnnnnnnnnn nggacacccc    4620
ttgatgccga gtcctgccca tctgccaccc gtgcaggtgc tggaggacaa tgactacggc    4680
cgtgcagtgg actggtgggg gctgggcgtg gtcatgtacg agatgatgtg cggtcgcctg    4740
cccttctaca accaggacca tgagaagctt tttgagctca tcctcatgga ggagatccgc    4800
ttcccgcgca cgcttggtcc cgaggccaag tccttgcttt cagggctgct caagaaggac    4860
cccaagcaga ggtgagggcc gcccatccca gctacaggct acacctccat cccctcatcc    4920
ccaggctgca cctgccctg cgccaggcgg tcctggcacc tcccagacta cactgatagc     4980
caaagcttga tgtccttggc cagggcnnnn nnnnnnnnnn nnnnnnnnnn nnnnnnnnnn    5040
nnnnnnnnnn nnnnnnnnnn nnnnnnnnnn nnnnnnnnnn nnnnnnnnnn nnnnnnnnnn    5100
nnnnnntgtg gtgctttgct acccacagct gctcagggac gctgcaccac cggctcccct    5160
```

-continued

```
ccctggcccc ggaacgtcct gtctggcggg ccctacatca caggaggaag gggcctgaac    5220
ccagggcctg gcaggtggc ggtaccgaca ctgtggcctt gtttcctgcc tgcaggcttg     5280
gcggggctc cgaggacgcc aaggagatca tgcagcatcg cttctttgcc ggtatcgtgt     5340
ggcagcacgt gtacgagaag aaggtgcggc tgctccccgc atattcacgc gcacgcatgc    5400
tccccacata tccacactca cgcatgcacg tggcacgctc gccagatttc nnnnnnnnnn    5460
nnnnnnnnnn nnnnnnnnnn nnnnnnnnnn nnnnnnnnnn nnnnnnnnnn nnnnnnnnnn    5520
nnnnnnnnnn nnnnnnnnnn nnnnnnnnnn ggcttgctgc tctctgacat cagtcctgcc    5580
tggagacccc ttggagatcc aggtgctttg aaggtcttga gcacacttga gggtgtgctg    5640
ggagtgggga gcgaagctca tgactgtccc gtctgcccac ctctgcagct cagcccaccc    5700
ttcaagcccc aggtcacgtc ggagactgac accaggtatt ttgatgagga gttcacggcc    5760
cagatgatca ccatcacacc acctgaccaa ggtgagggc cactgcctgc cccgcccac     5820
tcccttttct ctccacactc agagaggcct gcagtgttca gcttttttgg cttcagatgt    5880
tttaaaatct aaatatttaa aaaggttcct tttggagagt gccaatgatc agggtgggag    5940
gcagtnnnnn nnnnnnnnnn nnnnnnnnnn nnnnnnnnnn nnnnnnnnnn nnnnnnnnnn    6000
nnnnnnnnnn nnnnnnnnnn nnnnnnnnnn nnnnnnnnnn nnnnnaggtt ggcttcctac    6060
tggagctgtg ggtgggtgga ggtgcaggg aggtggggca ccggggtctg agctgtctac     6120
acccacagat gacagcatgg agtgtgtgga cagcgagcgc aggccccact tcccccagtt    6180
ctcctactcg gccagcagca cggcctgagg cggcggtgga ctgcgctgga cgatagcttg    6240
gagggatgga gaggcggcct cgtgccatga tctgtattta atggtttta tttctcgggt     6300
gcatttgag                                                            6309
```

<210> SEQ ID NO 4
<211> LENGTH: 480
<212> TYPE: PRT
<213> ORGANISM: Homo sapiens

<400> SEQUENCE: 4

```
Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
```

165                 170                 175
Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
    370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
        435                 440                 445

Ile Thr Pro Pro Asp Gln Asp Asp Ser Met Glu Cys Val Asp Ser Glu
    450                 455                 460

Arg Arg Pro His Phe Pro Gln Phe Ser Tyr Ser Ala Ser Ser Thr Ala
465                 470                 475                 480

<210> SEQ ID NO 5
<211> LENGTH: 2878
<212> TYPE: DNA
<213> ORGANISM: Homo sapiens
<220> FEATURE:
<221> NAME/KEY: CDS
<222> LOCATION: (425)..(1867)

<400> SEQUENCE: 5
cggcaggacc gagcgcggca ggcggctggc ccagcgcagc cagcgcggcc cgaaggacgg     60
gagcaggcgg ccgagcaccg agcgctgggc accgggcacc gagcggcggc ggcacgcgag    120
gcccggcccc gagcagcgcc cccgcccgcc gcggcctcca gcccggcccc gcccagcgcc    180
ggcccgcggg gatgcggagc ggcggcgcgc ggaggccgcg gcccggctag gcccgcgctc    240
gcgcccggac gcggcggccc ggggcttagg gaaggccgag ccagcctggg tcaaagaagt    300

```
caaagggct gcctggagga ggcagcctgt cagctggtgc atcagaggct gtggccaggc        360
cagctgggct cggggagcgc cagcctgaga ggagcgcgtg agcgtcgcgg gagcctcggg        420 cacc atg agc gac gtg gct att gtg aag gag ggt tgg ctg cac aaa cga        469
     Met Ser Asp Val Ala Ile Val Lys Glu Gly Trp Leu His Lys Arg
     1               5                   10                  15 ggg gag tac atc aag acc tgg cgg cca cgc tac ttc ctc ctc aag aat         517
Gly Glu Tyr Ile Lys Thr Trp Arg Pro Arg Tyr Phe Leu Leu Lys Asn
                20                  25                  30 gat ggc acc ttc att ggc tac aag gag cgg ccg cag gat gtg gac caa         565
Asp Gly Thr Phe Ile Gly Tyr Lys Glu Arg Pro Gln Asp Val Asp Gln
            35                  40                  45 cgt gag gct ccc ctc aac aac ttc tct gtg gcg cag tgc cag ctg atg         613
Arg Glu Ala Pro Leu Asn Asn Phe Ser Val Ala Gln Cys Gln Leu Met
        50                  55                  60 aag acg gag cgg ccc cgg ccc aac acc ttc atc atc cgc tgc ctg cag         661
Lys Thr Glu Arg Pro Arg Pro Asn Thr Phe Ile Ile Arg Cys Leu Gln
    65                  70                  75 tgg acc act gtc atc gaa cgc acc ttc cat gtg gag act cct gag gag         709
Trp Thr Thr Val Ile Glu Arg Thr Phe His Val Glu Thr Pro Glu Glu
80                  85                  90                  95 cgg gag gag tgg aca acc gcc atc cag act gtg gct gac ggc ctc aag         757
Arg Glu Glu Trp Thr Thr Ala Ile Gln Thr Val Ala Asp Gly Leu Lys
                100                 105                 110 aag cag gag gag gag gag atg gac ttc cgg tcg ggc tca ccc agt gac         805
Lys Gln Glu Glu Glu Glu Met Asp Phe Arg Ser Gly Ser Pro Ser Asp
            115                 120                 125 aac tca ggg gct gaa gag atg gag gtg tcc ctg gcc aag ccc aag cac         853
Asn Ser Gly Ala Glu Glu Met Glu Val Ser Leu Ala Lys Pro Lys His
        130                 135                 140 cgc gtg acc atg aac gag ttt gag tac ctg aag ctg ctg ggc aag ggc         901
Arg Val Thr Met Asn Glu Phe Glu Tyr Leu Lys Leu Leu Gly Lys Gly
    145                 150                 155 act ttc ggc aag gtg atc ctg gtg aag gag aag gcc aca ggc cgc tac         949
Thr Phe Gly Lys Val Ile Leu Val Lys Glu Lys Ala Thr Gly Arg Tyr
160                 165                 170                 175 tac gcc atg aag atc ctc aag aag gaa gtc atc gtg gcc aag gac gag         997
Tyr Ala Met Lys Ile Leu Lys Lys Glu Val Ile Val Ala Lys Asp Glu
                180                 185                 190 gtg gcc cac aca ctc acc gag aac cgc gtc ctg cag aac tcc agg cac        1045
Val Ala His Thr Leu Thr Glu Asn Arg Val Leu Gln Asn Ser Arg His
            195                 200                 205 ccc ttc ctc aca gcc ctg aag tac tct ttc cag acc cac gac cgc ctc        1093
Pro Phe Leu Thr Ala Leu Lys Tyr Ser Phe Gln Thr His Asp Arg Leu
        210                 215                 220 tgc ttt gtc atg gag tac gcc aac ggg ggc gag ctg ttc ttc cac ctg        1141
Cys Phe Val Met Glu Tyr Ala Asn Gly Gly Glu Leu Phe Phe His Leu
    225                 230                 235 tcc cgg gag cgt gtg ttc tcc gag gac cgg gcc cgc ttc tat ggc gct        1189
Ser Arg Glu Arg Val Phe Ser Glu Asp Arg Ala Arg Phe Tyr Gly Ala
240                 245                 250                 255 gag att gtg tca gcc ctg gac tac ctg cac tcg gag aag aac gtg gtg        1237
Glu Ile Val Ser Ala Leu Asp Tyr Leu His Ser Glu Lys Asn Val Val
                260                 265                 270 tac cgg gac ctc aag ctg gag aac ctc atg ctg gac aag gac ggg cac        1285
Tyr Arg Asp Leu Lys Leu Glu Asn Leu Met Leu Asp Lys Asp Gly His
            275                 280                 285 att aag atc aca gac ttc ggg ctg tgc aag gag ggg atc aag gac ggt        1333
Ile Lys Ile Thr Asp Phe Gly Leu Cys Lys Glu Gly Ile Lys Asp Gly
```

-continued

```
                290                 295                 300
gcc acc atg aag acc ttt tgc ggc aca cct gag tac ctg gcc ccc gag    1381
Ala Thr Met Lys Thr Phe Cys Gly Thr Pro Glu Tyr Leu Ala Pro Glu
    305                 310                 315 gtg ctg gag gac aat gac tac ggc cgt gca gtg gac tgg tgg ggg ctg    1429
Val Leu Glu Asp Asn Asp Tyr Gly Arg Ala Val Asp Trp Trp Gly Leu
320                 325                 330                 335 ggc gtg gtc atg tac gag atg atg tgc ggt cgc ctg ccc ttc tac aac    1477
Gly Val Val Met Tyr Glu Met Met Cys Gly Arg Leu Pro Phe Tyr Asn
                340                 345                 350 cag gac cat gag aag ctt ttt gag ctc atc ctc atg gag gag atc cgc    1525
Gln Asp His Glu Lys Leu Phe Glu Leu Ile Leu Met Glu Glu Ile Arg
            355                 360                 365 ttc ccg cgc acg ctt ggt ccc gag gcc aag tcc ttg ctt tca ggg ctg    1573
Phe Pro Arg Thr Leu Gly Pro Glu Ala Lys Ser Leu Leu Ser Gly Leu
        370                 375                 380 ctc aag aag gac ccc aag cag agg ctt ggc ggg ggc tcc gag gac gcc    1621
Leu Lys Lys Asp Pro Lys Gln Arg Leu Gly Gly Gly Ser Glu Asp Ala
    385                 390                 395 aag gag atc atg cag cat cgc ttc ttt gcc ggt atc gtg tgg cag cac    1669
Lys Glu Ile Met Gln His Arg Phe Phe Ala Gly Ile Val Trp Gln His
400                 405                 410                 415 gtg tac gag aag aag ctc agc cca ccc ttc aag ccc cag gtc acg tcg    1717
Val Tyr Glu Lys Lys Leu Ser Pro Pro Phe Lys Pro Gln Val Thr Ser
                420                 425                 430 gag act gac acc agg tat ttt gat gag gag ttc acg gcc cag atg atc    1765
Glu Thr Asp Thr Arg Tyr Phe Asp Glu Glu Phe Thr Ala Gln Met Ile
            435                 440                 445 acc atc aca cca cct gac caa gat gac agc atg gag tgt gtg gac agc    1813
Thr Ile Thr Pro Pro Asp Gln Asp Asp Ser Met Glu Cys Val Asp Ser
        450                 455                 460 gag cgc agg ccc cac ttc ccc cag ttc tcc tac tcg gcc agc ggc acg    1861
Glu Arg Arg Pro His Phe Pro Gln Phe Ser Tyr Ser Ala Ser Gly Thr
    465                 470                 475 gcc tga ggcggcggtg gactgcgctg gacgatagct tggagggatg gagaggcggc    1917
Ala
480 ctcgtgccat gatctgtatt taatggtttt tatttctcgg gtgcatttga gagaagccac    1977 gctgtcctct cgagcccaga tggaaagacg tttttgtgct gtgggcagca ccctcccccg    2037 cagcggggta gggaagaaaa ctatcctgcg ggttttaatt tatttcatcc agtttgttct    2097 ccgggtgtgg cctcagccct cagaacaatc cgattcacgt agggaaatgt taaggacttc    2157 tgcagctatg cgcaatgtgg cattgggggg ccgggcaggt cctgcccatg tgtcccctca    2217 ctctgtcagc cagccgccct gggctgtctg tcaccagcta tctgtcatct ctctggggcc    2277 ctgggcctca gttcaacctg gtggcaccag atgcaacctc actatggtat gctggccagc    2337 accctctcct gggggtggca ggcacacagc agccccccag cactaaggcc gtgtctctga    2397 ggacgtcatc ggaggctggg cccctgggat gggaccaggg atgggggatg ggccagggtt    2457 tacccagtgg gacagaggag caaggtttaa atttgttatt gtgtattatg ttgttcaaat    2517 gcatttgggg ggttttttaat cttttgtgaca ggaaagccct ccccttccc cttctgtgtc    2577 acagttcttg gtgactgtcc caccgggagc ctcccccctca gatgatctct ccacggtagc    2637 acttgacctt ttcgacgctt aacctttccg ctgtcgcccc aggccctccc tgactccctg    2697 tgggggtggc catccctggg ccccctccacg cctcctggcc agacgctgcc gctgccgctg    2757 caccacggcg ttttttttaca acattcaact ttagtatttt tactattata atataatatg    2817
```

```
gaaccttccc tccaaattct tcaataaaag ttgcttttca aaaaaaaaaa aaaaaaaaaa    2877
a                                                                    2878
```

<210> SEQ ID NO 6
<211> LENGTH: 480
<212> TYPE: PRT
<213> ORGANISM: Homo sapiens

<400> SEQUENCE: 6

```
Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Tyr Asn Gln
            340                 345                 350
```

```
Asp His Glu Lys Leu Phe Glu Leu Ile Leu Met Glu Ile Arg Phe
            355                 360                 365
Pro Arg Thr Leu Gly Pro Glu Ala Lys Ser Leu Leu Ser Gly Leu Leu
        370                 375                 380
Lys Lys Asp Pro Lys Gln Arg Leu Gly Gly Ser Glu Asp Ala Lys
385                 390                 395                 400
Glu Ile Met Gln His Arg Phe Phe Ala Gly Ile Val Trp Gln His Val
                405                 410                 415
Tyr Glu Lys Lys Leu Ser Pro Pro Phe Lys Pro Gln Val Thr Ser Glu
            420                 425                 430
Thr Asp Thr Arg Tyr Phe Asp Glu Glu Phe Thr Ala Gln Met Ile Thr
        435                 440                 445
Ile Thr Pro Pro Asp Gln Asp Asp Ser Met Glu Cys Val Asp Ser Glu
    450                 455                 460
Arg Arg Pro His Phe Pro Gln Phe Ser Tyr Ser Ala Ser Gly Thr Ala
465                 470                 475                 480

<210> SEQ ID NO 7
<211> LENGTH: 5317
<212> TYPE: DNA
<213> ORGANISM: Homo sapiens
<220> FEATURE:
<221> NAME/KEY: CDS
<222> LOCATION: (300)..(1745)

<400> SEQUENCE: 7
tgggaggggg cggtaagcgg gggctggggg gaggggcgg ggggggccgc gccgtgctag    60
ccgttgggcc tgcctcggag gaggcgtcgc cgccgccgct gccgctgccg gcgccgttgc   120
cgctgccggg aaacacaagg aaagggaacc agcgcagcgt ggcgatgggc gggggtagag   180
ccccgccgga gaggctgggc ggctgccggt gacagactgt gccctgtcca cggtgcctcc   240
tgcatgtcct gctgccctga gctgtcccga gctaggtgac agcgtaccac gctgccacc    299 atg aat gag gtg tct gtc atc aaa gaa ggc tgg ctc cac aag cgt ggt    347
Met Asn Glu Val Ser Val Ile Lys Glu Gly Trp Leu His Lys Arg Gly
1               5                   10                  15 gaa tac atc aag acc tgg agg cca cgg tac ttc ctg ctg aag agc gac    395
Glu Tyr Ile Lys Thr Trp Arg Pro Arg Tyr Phe Leu Leu Lys Ser Asp
            20                  25                  30 ggc tcc ttc att ggg tac aag gag agg ccc gag gcc cct gat cag act    443
Gly Ser Phe Ile Gly Tyr Lys Glu Arg Pro Glu Ala Pro Asp Gln Thr
        35                  40                  45 cta ccc ccc tta aac aac ttc tcc gta gca gaa tgc cag ctg atg aag    491
Leu Pro Pro Leu Asn Asn Phe Ser Val Ala Glu Cys Gln Leu Met Lys
    50                  55                  60 acc gag agg ccg cga ccc aac acc ttt gtc ata cgc tgc ctg cag tgg    539
Thr Glu Arg Pro Arg Pro Asn Thr Phe Val Ile Arg Cys Leu Gln Trp
65                  70                  75                  80 acc aca gtc atc gag agg acc ttc cac gtg gat tct cca gac gag agg    587
Thr Thr Val Ile Glu Arg Thr Phe His Val Asp Ser Pro Asp Glu Arg
                85                  90                  95 gag gag tgg atg cgg gcc atc cag atg gtc gcc aac agc ctc aag cag    635
Glu Glu Trp Met Arg Ala Ile Gln Met Val Ala Asn Ser Leu Lys Gln
            100                 105                 110 cgg gcc cca ggc gag gac ccc atg gac tac aag tgt ggc tcc ccc agt    683
Arg Ala Pro Gly Glu Asp Pro Met Asp Tyr Lys Cys Gly Ser Pro Ser
        115                 120                 125 gac tcc tcc acg act gag gag atg gaa gtg gcg gtc agc aag gca cgg    731
Asp Ser Ser Thr Thr Glu Glu Met Glu Val Ala Val Ser Lys Ala Arg
```

```
                130                  135                  140
gct aaa gtg acc atg aat gac ttc gac tat ctc aaa ctc ctt ggc aag      779
Ala Lys Val Thr Met Asn Asp Phe Asp Tyr Leu Lys Leu Leu Gly Lys
145                 150                 155                 160 gga acc ttt ggc aaa gtc atc ctg gtg cgg gag aag gcc act ggc cgc      827
Gly Thr Phe Gly Lys Val Ile Leu Val Arg Glu Lys Ala Thr Gly Arg
                165                 170                 175 tac tac gcc atg aag atc ctg cgg aag gaa gtc atc att gcc aag gat      875
Tyr Tyr Ala Met Lys Ile Leu Arg Lys Glu Val Ile Ile Ala Lys Asp
            180                 185                 190 gaa gtc gct cac aca gtc acc gag agc cgg gtc ctc cag aac acc agg      923
Glu Val Ala His Thr Val Thr Glu Ser Arg Val Leu Gln Asn Thr Arg
        195                 200                 205 cac ccg ttc ctc act gcg ctg aag tat gcc ttc cag acc cac gac cgc      971
His Pro Phe Leu Thr Ala Leu Lys Tyr Ala Phe Gln Thr His Asp Arg
    210                 215                 220 ctg tgc ttt gtg atg gag tat gcc aac ggg ggt gag ctg ttc ttc cac     1019
Leu Cys Phe Val Met Glu Tyr Ala Asn Gly Gly Glu Leu Phe Phe His
225                 230                 235                 240 ctg tcc cgg gag cgt gtc ttc aca gag gag cgg gcc cgg ttt tat ggt     1067
Leu Ser Arg Glu Arg Val Phe Thr Glu Glu Arg Ala Arg Phe Tyr Gly
                245                 250                 255 gca gag att gtc tcg gct ctt gag tac ttg cac tcg cgg gac gtg gta     1115
Ala Glu Ile Val Ser Ala Leu Glu Tyr Leu His Ser Arg Asp Val Val
            260                 265                 270 tac cgc gac atc aag ctg gaa aac ctc atg ctg gac aaa gat ggc cac     1163
Tyr Arg Asp Ile Lys Leu Glu Asn Leu Met Leu Asp Lys Asp Gly His
        275                 280                 285 atc aag atc act gac ttt ggc ctc tgc aaa gag ggc atc agt gac ggg     1211
Ile Lys Ile Thr Asp Phe Gly Leu Cys Lys Glu Gly Ile Ser Asp Gly
    290                 295                 300 gcc acc atg aaa acc ttc tgt ggg acc ccg gag tac ctg gcg cct gag     1259
Ala Thr Met Lys Thr Phe Cys Gly Thr Pro Glu Tyr Leu Ala Pro Glu
305                 310                 315                 320 gtg ctg gag gac aat gac tat ggc cgg gcc gtg gac tgg tgg ggg ctg     1307
Val Leu Glu Asp Asn Asp Tyr Gly Arg Ala Val Asp Trp Trp Gly Leu
                325                 330                 335 ggt gtg gtc atg tac gag atg atg tgc ggc cgc ctg ccc ttc tac aac     1355
Gly Val Val Met Tyr Glu Met Met Cys Gly Arg Leu Pro Phe Tyr Asn
            340                 345                 350 cag gac cac gag cgc ctc ttc gag ctc atc ctc atg gaa gag atc cgc     1403
Gln Asp His Glu Arg Leu Phe Glu Leu Ile Leu Met Glu Glu Ile Arg
        355                 360                 365 ttc ccg cgc acg ctc agc ccc gag gcc aag tcc ctg ctt gct ggg ctg     1451
Phe Pro Arg Thr Leu Ser Pro Glu Ala Lys Ser Leu Leu Ala Gly Leu
    370                 375                 380 ctt aag aag gac ccc aag cag agg ctt ggt ggg ggg ccc agc gat gcc     1499
Leu Lys Lys Asp Pro Lys Gln Arg Leu Gly Gly Gly Pro Ser Asp Ala
385                 390                 395                 400 aag gag gtc atg gag cac agg ttc ttc ctc agc atc aac tgg cag gac     1547
Lys Glu Val Met Glu His Arg Phe Phe Leu Ser Ile Asn Trp Gln Asp
                405                 410                 415 gtg gtc cag aag aag ctc ctg cca ccc ttc aaa cct cag gtc acg tcc     1595
Val Val Gln Lys Lys Leu Leu Pro Pro Phe Lys Pro Gln Val Thr Ser
            420                 425                 430 gag gtc gac aca agg tac ttc gat gat gaa ttt acc gcc cag tcc atc     1643
Glu Val Asp Thr Arg Tyr Phe Asp Asp Glu Phe Thr Ala Gln Ser Ile
        435                 440                 445 aca atc aca ccc cct gac cgc tat gac agc ctg ggc tta ctg gag ctg     1691
```

```
Thr Ile Thr Pro Pro Asp Arg Tyr Asp Ser Leu Gly Leu Leu Glu Leu
    450             455                 460 gac cag cgg acc cac ttc ccc cag ttc tcc tac tcg gcc agc atc cgc    1739
Asp Gln Arg Thr His Phe Pro Gln Phe Ser Tyr Ser Ala Ser Ile Arg
465             470                 475                 480 gag tga gcagtctgcc cacgcagagg acgcacgctc gctgccatca ccgctgggtg    1795
Glu gtttttccc cctaactttt tacttagcct ttttggtttg tgtccccacc cccacctcct    1855
cacccctttt ccagttcttc ttcaggcccc tcccagacgc accccagcgg ccctgcagc     1915 ccctgcctcc agcctccagc ctcacctttg tgcccagact cgcatttgga agactccacc   1975
tcccgcccag gcctgggctg ttgggcggtt ggagattcag gttttaatcc acacaagccc   2035
cagtgagggg tgaagcatgg cgcctggggc ctgcctgagt ttctggcctg ggtgtcgtgc   2095
tggtgtctgc ctccgcgctg ctgcatctgg acgaaggctg ccttctggtg ggacgcgaca   2155
cccggcagac agtggtgctg ccttccaggc cccgtggcct aggctcggag tggccaggca   2215
cggggcggtc caatccccca cccgctgtcc ccctatgggg gcagaaaagc aataatgtcc   2275 agggcaggc aggggccctt gggagctgca gggctggggg ttagggctgc tccctggtga    2335
atggagtcag atcctaggat ctgtaccatg ggaaccagg agtggccggg ctgggtgccg    2395
cctcctggtc cggcctcctc cccaccaaac tgtcctcacc ctatggatga ggcaggagga   2455
acatttgggg ccaaacctgc ctgcctccca gccccgtgcc ttactagggc ttccttccag   2515
ctggccttac ctcccgctgg accctgggcc tggcctggcc ccactggggg ctatgggctg   2575
ggctcaccct ctcctctgcg ggggtggagg gccaccagcc ttggctgtta caatcttaca   2635
ccggacagta ttgggcccca tggacttggt cagggagggg tggggtggg catctctggt    2695 acctattggg gtgggggggcc tctgaaaagg gaggctccta ggccccctc acccctccct   2755 ctccccaggg cccacgttc tgcagcctta aggttgaaca tgagtgcacg tccatgtcag    2815
tgctgtggga ctcctgtgcg tgcctcggac tgcgtgtgtc ggcgggacgc aggcacacgt   2875
gggtgtgtgt gcatgtgtgt ttgtgtgagg gcagcgtgtc ctccagtgtg catggtgtgt   2935
gggcttgggc cccatccctg gcccgagcat ttcatcctgt gggggagggg tgctgaccta   2995
gtgggaggag cccactgtg atccatgagc tgccctgccc acgcctcccc tccctgtagc    3055
aacacctctg ggtgtttgga gtttagcttt tgtgggtttg ctctccctat cccatctcct   3115
gtactacaca gttcatggca gggtgggag gggtggggtt ggttcgggtg ggtgagggtc    3175 ttttcctct gtgtgcgatg ttgttatctg acagttctcc gtcccactg gccttctcc      3235 tcgtcttcat atttgtacgg tacaagcaat aaagacactc atttcagacc agggcccagc   3295
ctgcactcac gccagcccaa ccactctggg ctttgccttg gtgatggagt cagacccctg   3355
ggccccagct cctcctgtac tagccgttcc cttcagcaag gagggcactg agctcagggt   3415
gagggcagct ggggtgtgtg caggagctca ggctggagag ggtgggtgga gctggtgctg   3475
tggggctgag gggtatggga aggctccccg catgtggggg tgggtggac agagaccact    3535 ccaggccctc agtgctgctt aggctaagag aggtgggtg gagggacagg gctggaagat    3595
ctgggtagcc cagaatgagg agggtgcctg tgctgtcact gaatgagagg gagtggttca   3655
ttccacccgg ctgccgagcc tcagaggggg gcattcctat cctgccccac ctccctgttt   3715
atgctgccac ctggaagcct tgaggccccc aaattccagt acagacccag tggtgtgttc   3775
atggtggcgt ggttgctgtc acctgggagc tcctgagcgt ttggttagaa ccctgttcag   3835
cttggggtca gccctcccct agtcactgcc ctttagcctg gatgtgtctg ggcccctgca   3895
```

-continued

```
cttcccgtgc ttgagtcacg tggctgcatg gccgggcgct ggccggatgg aacacctccc    3955
ccagcaaggg accagggacc agagccctgg cctgccctgc tgagccctgc tgtgcagagg    4015
gcctggcaca gatgaatttg agattttgcc gcaaggtgtt agcacttcac acccattgag    4075
tctttgagat tttaagtgaa tgtaagcaga aaaagtcaga tccaatttac agaaatcaga    4135
gttagctaca gctaggactc gtttggttgg ggttttttag tttgtctttc taaagtcatg    4195
tggaccttaa tttaattaca aaagtctacc ctggtggtca taaaataggc aggcctatga    4255
agaaaggcct tttactcttc catctcgtcc cagccccgag ttgacccacg ttgctgctcc    4315
tcacaccatg gtgatgcagg tctcgtagtg tgggcacagg cctggctacc tcatcttttt    4375
agtgcctctc tcctcttcca caggatgggg tcccacagct gcagcagctg gccccgtagt    4435
tgagcatgtg tggttatcct gtagagcttt tcccaagaag ggtgtttgaa cttagagtct    4495
taataaaatc ttaccaaata aattttgagt agaataatcg tcttttgcaa tgtacatttt    4555
aaaaatttca cacattcttt tttgtatata agaacagtg actgggcaca gtggctcatg    4615
cctgtaatcc cagcaatttg ggaggccgag gcgggcgggt ctcttgaggc caggggttcg    4675
agaccagcct gggcatcata gggagacctt catctctaca aaaaatacaa aaattagctg    4735
ggcatggtgg tgcatgcctg caatcccagc taacttggaa ggctgaggtg aggtgggaag    4795
atcacttgag cccaggagtt tgaggctgca gtgagctatg attgcggcac tgcactgcag    4855
cctgggacaa tgagactgtg tctctaaaaa taaaaaaaaa aaaaacatga tacatgctat    4915
taaaaaagac agcaaagcag gagtataaga aaggaaattc acccgaggtc gcagggcctt    4975
gagtactcat tttggtgctg attacctctc tgcaaatgga cacggcatca taaattggta    5035
gtttcctgct cttttgtgt aatctttcc agttaatgtg aagcctctgg gggctgccct    5095
cgtgcactga tggttgtgtg gagtcggggg cggcagtgcg attccctttt agctgctgca    5155
tgggggggaac tcaggctttc cagctgcttc ctggggttcc atggggtaga ccctcaacc    5215
gcttcagctg ccccgttaac aggaattgac ttggtttcgt ttggtgctac cagcagtcct    5275
gtaataaact agctatccat ctgtaaaaaa aaaaaaaaaa aa                       5317
```

<210> SEQ ID NO 8
<211> LENGTH: 481
<212> TYPE: PRT
<213> ORGANISM: Homo sapiens

<400> SEQUENCE: 8

```
Met Asn Glu Val Ser Val Ile Lys Glu Gly Trp Leu His Lys Arg Gly
1               5                   10                  15

Glu Tyr Ile Lys Thr Trp Arg Pro Arg Tyr Phe Leu Leu Lys Ser Asp
            20                  25                  30

Gly Ser Phe Ile Gly Tyr Lys Glu Arg Pro Glu Ala Pro Asp Gln Thr
        35                  40                  45

Leu Pro Pro Leu Asn Asn Phe Ser Val Ala Glu Cys Gln Leu Met Lys
    50                  55                  60

Thr Glu Arg Pro Arg Pro Asn Thr Phe Val Ile Arg Cys Leu Gln Trp
65                  70                  75                  80

Thr Thr Val Ile Glu Arg Thr Phe His Val Asp Ser Pro Asp Glu Arg
                85                  90                  95

Glu Glu Trp Met Arg Ala Ile Gln Met Val Ala Asn Ser Leu Lys Gln
            100                 105                 110

Arg Ala Pro Gly Glu Asp Pro Met Asp Tyr Lys Cys Gly Ser Pro Ser
```

```
                    115                 120                 125
Asp Ser Ser Thr Thr Glu Glu Met Glu Val Ala Val Ser Lys Ala Arg
130                 135                 140

Ala Lys Val Thr Met Asn Asp Phe Asp Tyr Leu Lys Leu Leu Gly Lys
145                 150                 155                 160

Gly Thr Phe Gly Lys Val Ile Leu Val Arg Glu Lys Ala Thr Gly Arg
                165                 170                 175

Tyr Tyr Ala Met Lys Ile Leu Arg Lys Glu Val Ile Ile Ala Lys Asp
            180                 185                 190

Glu Val Ala His Thr Val Thr Glu Ser Arg Val Leu Gln Asn Thr Arg
        195                 200                 205

His Pro Phe Leu Thr Ala Leu Lys Tyr Ala Phe Gln Thr His Asp Arg
    210                 215                 220

Leu Cys Phe Val Met Glu Tyr Ala Asn Gly Gly Glu Leu Phe Phe His
225                 230                 235                 240

Leu Ser Arg Glu Arg Val Phe Thr Glu Glu Arg Ala Arg Phe Tyr Gly
                245                 250                 255

Ala Glu Ile Val Ser Ala Leu Glu Tyr Leu His Ser Arg Asp Val Val
            260                 265                 270

Tyr Arg Asp Ile Lys Leu Glu Asn Leu Met Leu Asp Lys Asp Gly His
        275                 280                 285

Ile Lys Ile Thr Asp Phe Gly Leu Cys Lys Glu Gly Ile Ser Asp Gly
    290                 295                 300

Ala Thr Met Lys Thr Phe Cys Gly Thr Pro Glu Tyr Leu Ala Pro Glu
305                 310                 315                 320

Val Leu Glu Asp Asn Asp Tyr Gly Arg Ala Val Asp Trp Trp Gly Leu
                325                 330                 335

Gly Val Val Met Tyr Glu Met Met Cys Gly Arg Leu Pro Phe Tyr Asn
            340                 345                 350

Gln Asp His Glu Arg Leu Phe Glu Leu Ile Leu Met Glu Glu Ile Arg
        355                 360                 365

Phe Pro Arg Thr Leu Ser Pro Glu Ala Lys Ser Leu Leu Ala Gly Leu
    370                 375                 380

Leu Lys Lys Asp Pro Lys Gln Arg Leu Gly Gly Gly Pro Ser Asp Ala
385                 390                 395                 400

Lys Glu Val Met Glu His Arg Phe Phe Leu Ser Ile Asn Trp Gln Asp
                405                 410                 415

Val Val Gln Lys Lys Leu Leu Pro Pro Phe Lys Pro Gln Val Thr Ser
            420                 425                 430

Glu Val Asp Thr Arg Tyr Phe Asp Asp Glu Phe Thr Ala Gln Ser Ile
        435                 440                 445

Thr Ile Thr Pro Pro Asp Arg Tyr Asp Ser Leu Gly Leu Leu Glu Leu
    450                 455                 460

Asp Gln Arg Thr His Phe Pro Gln Phe Ser Tyr Ser Ala Ser Ile Arg
465                 470                 475                 480

Glu

<210> SEQ ID NO 9
<211> LENGTH: 1734
<212> TYPE: DNA
<213> ORGANISM: Homo sapiens
<220> FEATURE:
<221> NAME/KEY: CDS
<222> LOCATION: (113)..(1510)
```

```
<400> SEQUENCE: 9
gctgagtcat cactagagag tgggaagggc agcagcagca gagaatccaa accctaaagc      60
tgatatcaca aagtaccatt tctccaagtt gggggctcag aggggagtca tc atg agc     118
                                                          Met Ser
                                                          1 gat gtt acc att gtg aaa gaa ggt tgg gtt cag aag agg gga gaa tat       166
Asp Val Thr Ile Val Lys Glu Gly Trp Val Gln Lys Arg Gly Glu Tyr
        5                  10                  15 ata aaa aac tgg agg cca aga tac ttc ctt ttg aag aca gat ggc tca       214
Ile Lys Asn Trp Arg Pro Arg Tyr Phe Leu Leu Lys Thr Asp Gly Ser
 20                  25                  30 ttc ata gga tat aaa gag aaa cct caa gat gtg gat tta cct tat ccc       262
Phe Ile Gly Tyr Lys Glu Lys Pro Gln Asp Val Asp Leu Pro Tyr Pro
 35                  40                  45                  50 ctc aac aac ttt tca gtg gca aaa tgc cag tta atg aaa aca gaa cga       310
Leu Asn Asn Phe Ser Val Ala Lys Cys Gln Leu Met Lys Thr Glu Arg
                 55                  60                  65 cca aag cca aac aca ttt ata atc aga tgt ctc cag tgg act act gtt       358
Pro Lys Pro Asn Thr Phe Ile Ile Arg Cys Leu Gln Trp Thr Thr Val
             70                  75                  80 ata gag aga aca ttt cat gta gat act cca gag gaa agg gaa gaa tgg       406
Ile Glu Arg Thr Phe His Val Asp Thr Pro Glu Glu Arg Glu Glu Trp
         85                  90                  95 aca gaa gct atc cag gct gta gca gac aga ctg cag agg caa gaa gag       454
Thr Glu Ala Ile Gln Ala Val Ala Asp Arg Leu Gln Arg Gln Glu Glu
    100                 105                 110 gag aga atg aat tgt agt cca act tca caa att gat aat ata gga gag       502
Glu Arg Met Asn Cys Ser Pro Thr Ser Gln Ile Asp Asn Ile Gly Glu
115                 120                 125                 130 gaa gag atg gat gcc tct aca acc cat cat aaa aga aag aca atg aat       550
Glu Glu Met Asp Ala Ser Thr Thr His His Lys Arg Lys Thr Met Asn
                135                 140                 145 gat ttt gac tat ttg aaa cta cta ggt aaa ggc act ttt ggg aaa gtt       598
Asp Phe Asp Tyr Leu Lys Leu Leu Gly Lys Gly Thr Phe Gly Lys Val
            150                 155                 160 att ttg gtt cga gag aag gca agt gga aaa tac tat gct atg aag att       646
Ile Leu Val Arg Glu Lys Ala Ser Gly Lys Tyr Tyr Ala Met Lys Ile
        165                 170                 175 ctg aag aaa gaa gtc att att gca aag gat gaa gtg gca cac act cta       694
Leu Lys Lys Glu Val Ile Ile Ala Lys Asp Glu Val Ala His Thr Leu
    180                 185                 190 act gaa agc aga gta tta aag aac act aga cat ccc ttt tta aca tcc       742
Thr Glu Ser Arg Val Leu Lys Asn Thr Arg His Pro Phe Leu Thr Ser
195                 200                 205                 210 ttg aaa tat tcc ttc cag aca aaa gac cgt ttg tgt ttt gtg atg gaa       790
Leu Lys Tyr Ser Phe Gln Thr Lys Asp Arg Leu Cys Phe Val Met Glu
                215                 220                 225 tat gtt aat ggg ggc gag ctg ttt ttc cat ttg tcg aga gag cgg gtg       838
Tyr Val Asn Gly Gly Glu Leu Phe Phe His Leu Ser Arg Glu Arg Val
            230                 235                 240 ttc tct gag gac cgc aca cgt ttc tat ggt gca gaa att gtc tct gcc       886
Phe Ser Glu Asp Arg Thr Arg Phe Tyr Gly Ala Glu Ile Val Ser Ala
        245                 250                 255 ttg gac tat cta cat tcc gga aag att gtg tac cgt gat ctc aag ttg       934
Leu Asp Tyr Leu His Ser Gly Lys Ile Val Tyr Arg Asp Leu Lys Leu
    260                 265                 270 gag aat cta atg ctg gac aaa gat ggc cac ata aaa att aca gat ttt       982
Glu Asn Leu Met Leu Asp Lys Asp Gly His Ile Lys Ile Thr Asp Phe
275                 280                 285                 290
```

```
gga ctt tgc aaa gaa ggg atc aca gat gca gcc acc atg aag aca ttc      1030
Gly Leu Cys Lys Glu Gly Ile Thr Asp Ala Ala Thr Met Lys Thr Phe
                295                 300                 305 tgt ggc act cca gaa tat ctg gca cca gag gtg tta gaa gat aat gac      1078
Cys Gly Thr Pro Glu Tyr Leu Ala Pro Glu Val Leu Glu Asp Asn Asp
            310                 315                 320 tat ggc cga gca gta gac tgg tgg ggc cta ggg gtt gtc atg tat gaa      1126
Tyr Gly Arg Ala Val Asp Trp Trp Gly Leu Gly Val Val Met Tyr Glu
        325                 330                 335 atg atg tgt ggg agg tta cct ttc tac aac cag gac cat gag aaa ctt      1174
Met Met Cys Gly Arg Leu Pro Phe Tyr Asn Gln Asp His Glu Lys Leu
    340                 345                 350 ttt gaa tta ata tta atg gaa gac att aaa ttt cct cga aca ctc tct      1222
Phe Glu Leu Ile Leu Met Glu Asp Ile Lys Phe Pro Arg Thr Leu Ser
355                 360                 365                 370 tca gat gca aaa tca ttg ctt tca ggg ctc ttg ata aag gat cca aat      1270
Ser Asp Ala Lys Ser Leu Leu Ser Gly Leu Leu Ile Lys Asp Pro Asn
                375                 380                 385 aaa cgc ctt ggt gga gga cca gat gat gca aaa gaa att atg aga cac      1318
Lys Arg Leu Gly Gly Gly Pro Asp Asp Ala Lys Glu Ile Met Arg His
            390                 395                 400 agt ttc ttc tct gga gta aac tgg caa gat gta tat gat aaa aag ctt      1366
Ser Phe Phe Ser Gly Val Asn Trp Gln Asp Val Tyr Asp Lys Lys Leu
        405                 410                 415 gta cct cct ttt aaa cct caa gta aca tct gag aca gat act aga tat      1414
Val Pro Pro Phe Lys Pro Gln Val Thr Ser Glu Thr Asp Thr Arg Tyr
    420                 425                 430 ttt gat gaa gaa ttt aca gct cag act att aca ata aca cca cct gaa      1462
Phe Asp Glu Glu Phe Thr Ala Gln Thr Ile Thr Ile Thr Pro Pro Glu
435                 440                 445                 450 aaa tgt cag caa tca gat tgt ggc atg ctg ggt aac tgg aaa aaa taa      1510
Lys Cys Gln Gln Ser Asp Cys Gly Met Leu Gly Asn Trp Lys Lys
                455                 460                 465 taaaaatcgg cttcctacag ccagcagcac agtcacccat ggaactgttg gctttggatt   1570
aaatgtggaa ttgaacgact acccagaagt gttctggaaa gaagcgagat gtgtggcctg   1630
cctcaccgtc ctcacccatc aaaagcacca gcaggcacgt taactcgaat tctcacaagg   1690
aaaaggccat taaagctcaa ggtgcatttc aaactccagg ctac                   1734

<210> SEQ ID NO 10
<211> LENGTH: 465
<212> TYPE: PRT
<213> ORGANISM: Homo sapiens

<400> SEQUENCE: 10

Met Ser Asp Val Thr Ile Val Lys Glu Gly Trp Val Gln Lys Arg Gly
1               5                   10                  15

Glu Tyr Ile Lys Asn Trp Arg Pro Arg Tyr Phe Leu Leu Lys Thr Asp
            20                  25                  30

Gly Ser Phe Ile Gly Tyr Lys Glu Lys Pro Gln Asp Val Asp Leu Pro
        35                  40                  45

Tyr Pro Leu Asn Asn Phe Ser Val Ala Lys Cys Gln Leu Met Lys Thr
    50                  55                  60

Glu Arg Pro Lys Pro Asn Thr Phe Ile Ile Arg Cys Leu Gln Trp Thr
65                  70                  75                  80

Thr Val Ile Glu Arg Thr Phe His Val Asp Thr Pro Glu Glu Arg Glu
                85                  90                  95
```

Glu Trp Thr Glu Ala Ile Gln Ala Val Ala Asp Arg Leu Gln Arg Gln
            100                 105                 110

Glu Glu Glu Arg Met Asn Cys Ser Pro Thr Ser Gln Ile Asp Asn Ile
    115                 120                 125

Gly Glu Glu Met Asp Ala Ser Thr Thr His His Lys Arg Lys Thr
130                 135                 140

Met Asn Asp Phe Asp Tyr Leu Lys Leu Leu Gly Lys Gly Thr Phe Gly
145                 150                 155                 160

Lys Val Ile Leu Val Arg Glu Lys Ala Ser Gly Lys Tyr Tyr Ala Met
                165                 170                 175

Lys Ile Leu Lys Lys Glu Val Ile Ile Ala Lys Asp Glu Val Ala His
            180                 185                 190

Thr Leu Thr Glu Ser Arg Val Leu Lys Asn Thr Arg His Pro Phe Leu
            195                 200                 205

Thr Ser Leu Lys Tyr Ser Phe Gln Thr Lys Asp Arg Leu Cys Phe Val
        210                 215                 220

Met Glu Tyr Val Asn Gly Gly Glu Leu Phe Phe His Leu Ser Arg Glu
225                 230                 235                 240

Arg Val Phe Ser Glu Asp Arg Thr Arg Phe Tyr Gly Ala Glu Ile Val
                245                 250                 255

Ser Ala Leu Asp Tyr Leu His Ser Gly Lys Ile Val Tyr Arg Asp Leu
            260                 265                 270

Lys Leu Glu Asn Leu Met Leu Asp Lys Asp Gly His Ile Lys Ile Thr
        275                 280                 285

Asp Phe Gly Leu Cys Lys Glu Gly Ile Thr Asp Ala Ala Thr Met Lys
290                 295                 300

Thr Phe Cys Gly Thr Pro Glu Tyr Leu Ala Pro Glu Val Leu Glu Asp
305                 310                 315                 320

Asn Asp Tyr Gly Arg Ala Val Asp Trp Trp Gly Leu Gly Val Val Met
                325                 330                 335

Tyr Glu Met Met Cys Gly Arg Leu Pro Phe Tyr Asn Gln Asp His Glu
            340                 345                 350

Lys Leu Phe Glu Leu Ile Leu Met Glu Asp Ile Lys Phe Pro Arg Thr
        355                 360                 365

Leu Ser Ser Asp Ala Lys Ser Leu Leu Ser Gly Leu Leu Ile Lys Asp
370                 375                 380

Pro Asn Lys Arg Leu Gly Gly Gly Pro Asp Asp Ala Lys Glu Ile Met
385                 390                 395                 400

Arg His Ser Phe Phe Ser Gly Val Asn Trp Gln Asp Val Tyr Asp Lys
                405                 410                 415

Lys Leu Val Pro Pro Phe Lys Pro Gln Val Thr Ser Glu Thr Asp Thr
            420                 425                 430

Arg Tyr Phe Asp Glu Glu Phe Thr Ala Gln Thr Ile Thr Ile Thr Pro
        435                 440                 445

Pro Glu Lys Cys Gln Gln Ser Asp Cys Gly Met Leu Gly Asn Trp Lys
        450                 455                 460

Lys
465

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic

```
                Motif for N-myristoylation
<220> FEATURE:
<221> NAME/KEY: MOD_RES
<222> LOCATION: (3)..(5)
<223> OTHER INFORMATION: Any naturally occurring amino acid
<220> FEATURE:
<221> NAME/KEY: MOD_RES
<222> LOCATION: (6)..(6)
<223> OTHER INFORMATION: Ser, Ala, Thr or Phe
<220> FEATURE:
<221> NAME/KEY: MOD_RES
<222> LOCATION: (7)..(9)
<223> OTHER INFORMATION: Any naturally occurring amino acid

<400> SEQUENCE: 11

Met Gly Xaa Xaa Xaa Xaa Xaa Xaa Xaa
1               5

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      N-myristoylation signal sequence

<400> SEQUENCE: 12

Met Gly Ser Ser Lys Ser Lys Pro Lys Asp Pro Ser Gln Arg
1               5                   10

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      N-myristoylation signal sequence

<400> SEQUENCE: 13

Met Gly Ser Ser Lys Ser Lys Pro Lys Asp Pro Ser Gln Arg Arg Arg
1               5                   10                  15

Arg Ile Arg Thr
            20

<210> SEQ ID NO 14
<211> LENGTH: 969
<212> TYPE: DNA
<213> ORGANISM: Artificial Sequence
<220> FEATURE:
<223> OTHER INFORMATION: Description of Artificial Sequence: Synthetic
      Mer nucleotide

<400> SEQUENCE: 14
ggagatccac gaaatgaaat gggtgcttca ggagacatga gggctgccaa cctttggcca      60
agccctcttg tgattaagca cactaagaag aatagccctg ccttgtcctt gacagctgac     120
cagatggtca gtgccttgtt ggatgctgaa ccgcccatga tctattctga atatgatcct     180
tctagaccct tcagtgaagc ctcaatgatg ggcttattga ccaacctagc agatagggag     240
ctggttcata tgatcaactg gcaaagagag tgccaggct tgggggactt gaatctccat     300
gatcaggtcc accttctcga gtgtgcctgg ctggagattc tgatgattgg tctcgtctgg     360
cgctccatgg aacacccggg gaagctcctg tttgctccta acttgctcct ggacaggaat     420
caaggtaaat gtgtggaagg catggtggag atctttgaca tgttgctggc tacgtcaagt     480
cggttccgca tgatgaacct gcagggagaa gagtttgtgt gcctcaaatc catcattttg     540
```

```
cttaattccg agtgtacac gtttctgtcc agcaccttga agtctctgga agagaaggac    600
cacatccacc gtgtcctgga caagatcaca gacactttga tccacctgat ggccaaagct    660
ggcctgactc tgcagcagca gcatcgccgc ctagctcagc tccttctcat tctttcccat    720
atccggcaca tgagtaacaa aggcatggag catctctaca acatgaaatg caagaacgtt    780
gtgcccctct atgacctgct cctggagatg ttggatgccc accgcttca tgccccagcc    840 agtcgcatgg gagtgccccc agaggagccc agccagaccc agctggccac caccagctcc    900
acttcagcac attccttaca aacctactac atacccccgg aagcagaggg cttccccaac    960
acgatctga                                                           969
```

<210> SEQ ID NO 15
<211> LENGTH: 322
<212> TYPE: PRT
<213> ORGANISM: Artificial Sequence
<220> FEATURE:
<223> OTHER INFORMATION: Description of Artificial Sequence: Synthetic
      Mer amino acid

<400> SEQUENCE: 15

```
Gly Asp Pro Arg Asn Glu Met Gly Ala Ser Gly Asp Met Arg Ala Ala
1               5                   10                  15

Asn Leu Trp Pro Ser Pro Leu Val Ile Lys His Thr Lys Lys Asn Ser
            20                  25                  30

Pro Ala Leu Ser Leu Thr Ala Asp Gln Met Val Ser Ala Leu Leu Asp
        35                  40                  45

Ala Glu Pro Pro Met Ile Tyr Ser Glu Tyr Asp Pro Ser Arg Pro Phe
    50                  55                  60

Ser Glu Ala Ser Met Met Gly Leu Leu Thr Asn Leu Ala Asp Arg Glu
65                  70                  75                  80

Leu Val His Met Ile Asn Trp Ala Lys Arg Val Pro Gly Phe Gly Asp
                85                  90                  95

Leu Asn Leu His Asp Gln Val His Leu Leu Glu Cys Ala Trp Leu Glu
            100                 105                 110

Ile Leu Met Ile Gly Leu Val Trp Arg Ser Met Glu His Pro Gly Lys
        115                 120                 125

Leu Leu Phe Ala Pro Asn Leu Leu Leu Asp Arg Asn Gln Gly Lys Cys
    130                 135                 140

Val Glu Gly Met Val Glu Ile Phe Asp Met Leu Leu Ala Thr Ser Ser
145                 150                 155                 160

Arg Phe Arg Met Met Asn Leu Gln Gly Glu Glu Phe Val Cys Leu Lys
                165                 170                 175

Ser Ile Ile Leu Leu Asn Ser Gly Val Tyr Thr Phe Leu Ser Ser Thr
            180                 185                 190

Leu Lys Ser Leu Glu Glu Lys Asp His Ile His Arg Val Leu Asp Lys
        195                 200                 205

Ile Thr Asp Thr Leu Ile His Leu Met Ala Lys Ala Gly Leu Thr Leu
    210                 215                 220

Gln Gln Gln His Arg Arg Leu Ala Gln Leu Leu Leu Ile Leu Ser His
225                 230                 235                 240

Ile Arg His Met Ser Asn Lys Gly Met Glu His Leu Tyr Asn Met Lys
                245                 250                 255

Cys Lys Asn Val Val Pro Leu Tyr Asp Leu Leu Leu Glu Met Leu Asp
            260                 265                 270

Ala His Arg Leu His Ala Pro Ala Ser Arg Met Gly Val Pro Pro Glu
```

|     |     |     |     |     |     |     |     |     |     |     |     |     |     |
| --- | --- | --- | --- | --- | --- | --- | --- | --- | --- | --- | --- | --- | --- |
|     |     | 275 |     |     |     | 280 |     |     |     | 285 |     |     |     |
| Glu | Pro | Ser | Gln | Thr | Gln | Leu | Ala | Thr | Thr | Ser | Ser | Thr | Ser | Ala | His |
|     |     | 290 |     |     |     | 295 |     |     |     | 300 |     |     |     |
| Ser | Leu | Gln | Thr | Tyr | Tyr | Ile | Pro | Pro | Glu | Ala | Glu | Gly | Phe | Pro | Asn |
| 305 |     |     |     |     | 310 |     |     |     |     | 315 |     |     |     |     | 320 |
| Thr | Ile |

<210> SEQ ID NO 16
<211> LENGTH: 34
<212> TYPE: DNA
<213> ORGANISM: Escherichia virus Lambda
<220> FEATURE:
<223> OTHER INFORMATION: LoxP Sequence

<400> SEQUENCE: 16
ataacttcgt ataatgtatg ctatacgaag ttat                                    34

<210> SEQ ID NO 17
<211> LENGTH: 1032
<212> TYPE: DNA
<213> ORGANISM: Escherichia virus Lambda
<220> FEATURE:
<223> OTHER INFORMATION: Cre

<400> SEQUENCE: 17
atgtccaatt tactgaccgt acaccaaaat ttgcctgcat taccggtcga tgcaacgagt      60
gatgaggttc gcaagaacct gatggacatg ttcagggatc gccaggcgtt tctgagcat      120
acctggaaaa tgcttctgtc cgtttgccgg tcgtgggcgg catggtgcaa gttgaataac    180
cggaaatggt tcccgcagaa acctgaagat gttcgcgatt atcttctata tcttcaggcg    240
cgcggtctgg cagtaaaaac tatccagcaa catttgggcc agctaaacat gcttcatcgt    300
cggtccgggc tgccacgacc aagtgacagc aatgctgttt cactggttat gcggcggatc    360
cgaaaagaaa acgttgatgc cggtgaacgt gcaaaacagg ctctagcgtt cgaacgcact    420
gatttcgacc aggttcgttc actcatggaa atagcgatc gctgccagga tatacgtaat    480
ctggcatttc tggggattgc ttataacacc ctgttacgta tagccgaaat tgccaggatc    540
agggttaaag atatctcacg tactgacggt gggagaatgt taatccatat tggcagaacg    600
aaaacgctgg ttagcaccgc aggtgtagag aaggcactta gcctgggggt aactaaactg    660
gtcgagcgat ggatttccgt ctctggtgta gctgatgatc cgaataacta cctgttttgc    720
cgggtcagaa aaaatggtgt tgccgcgcca tctgccacca gccagctatc aactcgcgcc    780
ctggaaggga ttttttgaagc aactcatcga ttgatttacg gcgctaagga tgactctggt    840
cagagatacc tggcctggtc tggacacagt gcccgtgtcg gagccgcgcg agatatggcc    900
cgcgctggag tttcaatacc ggagatcatg caagctggtg gctggaccaa tgtaaatatt    960
gtcatgaact atatccgtaa cctggatagt gaaacagggg caatggtgcg cctgctggaa   1020
gatggcgatt ag                                                        1032

<210> SEQ ID NO 18
<211> LENGTH: 343
<212> TYPE: PRT
<213> ORGANISM: Escherichia virus Lambda
<220> FEATURE:
<223> OTHER INFORMATION: Cre

<400> SEQUENCE: 18

Met Ser Asn Leu Leu Thr Val His Gln Asn Leu Pro Ala Leu Pro Val

```
          1               5                  10                 15
        Asp Ala Thr Ser Asp Glu Val Arg Lys Asn Leu Met Asp Met Phe Arg
                        20                 25                 30

Asp Arg Gln Ala Phe Ser Glu His Thr Trp Lys Met Leu Leu Ser Val
                        35                 40                 45

Cys Arg Ser Trp Ala Ala Trp Cys Lys Leu Asn Asn Arg Lys Trp Phe
                        50                 55                 60

Pro Ala Glu Pro Glu Asp Val Arg Asp Tyr Leu Leu Tyr Leu Gln Ala
         65                 70                 75                 80

Arg Gly Leu Ala Val Lys Thr Ile Gln Gln His Leu Gly Gln Leu Asn
                         85                 90                 95

Met Leu His Arg Arg Ser Gly Leu Pro Arg Pro Ser Asp Ser Asn Ala
                        100                105                110

Val Ser Leu Val Met Arg Arg Ile Arg Lys Glu Asn Val Asp Ala Gly
                        115                120                125

Glu Arg Ala Lys Gln Ala Leu Ala Phe Glu Arg Thr Asp Phe Asp Gln
                        130                135                140

Val Arg Ser Leu Met Glu Asn Ser Asp Arg Cys Gln Asp Ile Arg Asn
        145                150                155                160

Leu Ala Phe Leu Gly Ile Ala Tyr Asn Thr Leu Leu Arg Ile Ala Glu
                        165                170                175

Ile Ala Arg Ile Arg Val Lys Asp Ile Ser Arg Thr Asp Gly Gly Arg
                        180                185                190

Met Leu Ile His Ile Gly Arg Thr Lys Thr Leu Val Ser Thr Ala Gly
                        195                200                205

Val Glu Lys Ala Leu Ser Leu Gly Val Thr Lys Leu Val Glu Arg Trp
                        210                215                220

Ile Ser Val Ser Gly Val Ala Asp Pro Asn Asn Tyr Leu Phe Cys
        225                230                235                240

Arg Val Arg Lys Asn Gly Val Ala Ala Pro Ser Ala Thr Ser Gln Leu
                        245                250                255

Ser Thr Arg Ala Leu Glu Gly Ile Phe Glu Ala Thr His Arg Leu Ile
                        260                265                270

Tyr Gly Ala Lys Asp Asp Ser Gly Gln Arg Tyr Leu Ala Trp Ser Gly
                        275                280                285

His Ser Ala Arg Val Gly Ala Ala Arg Asp Met Ala Arg Ala Gly Val
                        290                295                300

Ser Ile Pro Glu Ile Met Gln Ala Gly Gly Trp Thr Asn Val Asn Ile
        305                310                315                320

Val Met Asn Tyr Ile Arg Asn Leu Asp Ser Glu Thr Gly Ala Met Val
                        325                330                335

Arg Leu Leu Glu Asp Gly Asp
                        340

<210> SEQ ID NO 19
<211> LENGTH: 1383
<212> TYPE: DNA
<213> ORGANISM: Artificial Sequence
<220> FEATURE:
<223> OTHER INFORMATION: Description of Artificial Sequence: Synthetic
      IRES-EGFP

<400> SEQUENCE: 19
gaattcctgc aggcctcgag ggccggcgcg ccgcggccgc tacgtaaatt ccgcccctct      60
ccctcccccc cccctaacgt tactggccga agccgcttgg aataaggccg gtgtgcgttt     120
```

```
gtctatatgt tattttccac catattgccg tcttttggca atgtgagggc ccggaaacct    180
ggccctgtct tcttgacgag cattcctagg ggtctttccc ctctcgccaa aggaatgcaa    240
ggtctgttga atgtcgtgaa ggaagcagtt cctctggaag cttcttgaag acaaacaacg    300
tctgtagcga ccctttgcag gcagcggaac cccccacctg cgacaggtg cctctgcggc     360 caaaagccac gtgtataaga tacacctgca aggcggcac aaccccagtg ccacgttgtg     420
agttggatag ttgtggaaag agtcaaatgg ctctcctcaa gcgtattcaa caaggggctg    480
aaggatgccc agaaggtacc ccattgtatg ggatctgatc tggggcctcg gtgcacatgc    540
tttacatgtg tttagtcgag gttaaaaaac gtctaggccc cccgaaccac ggggacgtgg    600
ttttcctttg aaaaacacga tgataagctt gccacaacca tggtgagcaa gggcgaggag    660
ctgttcaccg gggtggtgcc catcctggtc gagctggacg gcgacgtaaa cggccacaag    720
ttcagcgtgt ccggcgaggg cgagggcgat gccacctacg gcaagctgac cctgaagttc    780
atctgcacca ccggcaagct gcccgtgccc tggcccaccc tcgtgaccac cctgacctac    840
ggcgtgcagt gcttcagccg ctaccccgac cacatgaagc agcacgactt cttcaagtcc    900
gccatgcccg aaggctacgt ccaggagcgc accatcttct tcaaggacga cggcaactac    960
aagacccgcg ccgaggtgaa gttcgagggc gacaccctgg tgaaccgcat cgagctgaag    1020
ggcatcgact tcaaggagga cggcaacatc ctggggcaca gctggagta caactacaac    1080 agccacaacg tctatatcat ggccgacaag cagaagaacg gcatcaaggt gaacttcaag    1140
atccgccaca acatcgagga cggcagcgtg cagctcgccg accactacca gcagaacacc    1200
cccatcggcg acggccccgt gctgctgccc gacaaccact acctgagcac ccagtccgcc    1260
ctgagcaaag accccaacga gaagcgcgat cacatggtcc tgctggagtt cgtgaccgcc    1320
gccgggatca ctctcggcat ggacgagctg tacaagtaaa gcggcccagc cacagtggtc    1380
gac                                                                 1383

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cggaattcac catggggagt agcaag                                           26

<210> SEQ ID NO 21
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cggaattcgg atccagcgta atctggaaca tcgtatgggt aggccgtgct gctggccgag     60

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 22
cgggatccgg agatccacga aatgaaatg                               29

<210> SEQ ID NO 23
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cgggatccgt cgactcagat cgtgttgggg aagcc                        35

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tacacaattc agagcgatgt gtggt                                   25

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ctggttcctc caatgggata tcttc                                   25

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggctgtaatt cccctccatc g                                       21

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ccagttggta acaatgccat gt                                      22

<210> SEQ ID NO 28
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 28
gaattctcga ggaattc                                                  17

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gaattcctcg aggcggccgc                                               20
```

TRANSGENIC MOUSE MODEL OF RETINAL VASCULAR DISEASE, METHOD OF MAKING, AND METHOD OF USING

CROSS REFERENCE TO RELATED APPLICATIONS

This application is based on and claims priority under 35 U.S.C. § 119 to Japanese Patent Application 2017-156031, filed on Aug. 10, 2017, the entire content of which is incorporated herein by reference.

SEQUENCE LISTING

The instant application contains a Sequence Listing which has been submitted electronically in ASCII format and is hereby incorporated by reference in its entirety. Said ASCII copy, created on Sep. 28, 2018, is named P55331_SL.txt and is 74,053 bytes in size.

TECHNICAL FIELD

The present disclosure relates to a non-human model animal of a retinal vascular disease such as diabetic retinopathy, a method for producing a non-human model animal of a retinal vascular disease, and a method for screening a drug for treating or preventing a retinal vascular disease.

BACKGROUND DISCUSSION

A retinal vascular disease collectively refers to ocular diseases caused by pathological changes such as hemorrhage, effusion, aneurysm, edema, ischemia, and infarct that occur in at least part of retinal blood vessels. Representative cases of the retinal vascular diseases are diabetic retinopathy, retinopathy of prematurity, and retinal venous occlusion. The retinal vascular diseases also include Coats' disease and the like.

Chronic complications of diabetes are caused by microvascular angiopathy occurring in arterioles, capillaries, and the like, and include retinopathy, nephropathy, neuropathy and the like. In particular, diabetic retinopathy is caused by microvascular angiopahty occurring in the retina due to a continuous hyperglycemic state, and may lead to blindness at the age of maturity. The meta-research based on 35 research projects in the world reporting the prevalence rate for diabetic retinopathy has reported that one in every three diabetic patients suffers from some type of retinopathy, and one in every eight or nine diabetic patients suffers from retinopathy that may adversely affect eyesight.

Hypertension or arteriosclerosis is considered as a risk factor for retinal venous occlusion. Retinal venous occlusion occurs at relatively high frequency, and the prevalence rate for retinal venous occlusion in people of forty and above is 2%. Retinal venous occlusion is less likely to lead to blindness, but may lead to a decrease in vision accompanied with anorthopia, and the quality of vision is thus lowered significantly.

Retinopathy of prematurity is a main factor for infant blindness, and it is considered that more than fifty thousand patients lose their eyesight in the world. In this country, retinopathy of prematurity is the first-ranking cause of blindness in the schools for the blind, and severe cases increase with the improvement of neonatal care.

In retinal vascular diseases such as diabetic retinopathy, retinal ischemia caused by vascular occlusion and retinal edema caused by increased vascular permeability lead to a decrease in vision. Ischemic retina falls into a hypoxic state, produces a vascular endothelial growth factor (abbreviated as "VEGF" hereinafter), and induces angiogenesis. However, pathological new blood vessels are formed deviating from the retina, and do not lead to the improvement of ischemia. Furthermore, new blood vessels are weak, and thus hemorrhage is likely to occur. In addition, the contraction of membranous tissues around the blood vessels causes detached retina, leading to blindness. On the other hand, regarding retinal edema, vascular permeability increases based on vasodilatation or an aneurysm following occlusion or inflammation of retinal blood vessels, leading to edema. Retinal edema does not lead to blindness, but causes a significant decrease in vision. If retinal edema lingers for a long period of time, visual cells and retinal nerve cells will undergo irreversible degeneration, and the vision will not be recovered even if edema disappears.

Surgical treatments such as photocoagulation and vitreous surgery, and drug treatments using a drug such as an anti-VEGF drug for inhibiting VEGF protein are known as treatments for ischemia (and subsequent intraocular hemorrhage or retinal detachment) in retinal vascular diseases. An object of these treatments is to inhibit pathological angiogenesis in retinal ischemia, and the treatments do not improve ischemia itself, but a therapeutic effect of stopping the progression of ischemia and preventing blindness is confirmed. On the other hand, a main treatment for retinal edema is a treatment using anti-VEGF drugs that are approved in recent years. An effect of suppressing an increase in permeability, which is exhibited by the anti-VEGF drugs, lasts temporarily, and it is necessary to continuously administer the very expensive drugs intraocularly due to repeated recurrence. Considering that the number of patients suffering from diabetic maculopathy is about one million and one hundred thousand in this country, a further increase in medical cost cannot be avoided in the future. Furthermore, it is difficult to say that a vision improvement effect is not sufficient, and therefore, there has been a demand for the development of a novel therapeutic drug.

Regarding diabetic nephropathy, microvascular sclerosis occurs in the glomeruli, leading to the deterioration of the renal function, due to a continuous hyperglycemic state. In advanced cases, renal sclerosis is promoted by the occurrence of an ischemic state, leading to renal failure. A main treatment for diabetic nephropathy is strict control of blood sugar and blood pressure, and a certain therapeutic effect is confirmed in a treatment using angiotensin converting enzyme inhibitor or an angiotensin II receptor antagonist, but diabetic nephropathy is not completely cured. When renal failure occurs, the treatment is shifted to a treatment using dialysis.

An attempt is made to use non-human disease model animals in the development of a method for treating, preventing, or diagnosing a disease, in the pathologic analysis of a disease, and the like. For example, it is reported that spontaneous model animals, genetically modified model animals, and model animals in which the onset of a disease is induced by drugs or the like have been produced as non-human diabetic model animals. Furthermore, non-human model animals in which retinal ischemia is artificially induced by high oxygen loading to form abnormal new blood vessels have been reported (Non-Patent Document 1).

CITATION LIST

Non Patent Literature

Non-Patent Document 1: L. E. Smith et al., "Oxygen-induced retinopathy in the mouse", Investigative Ophthalmology & Visual Science January 1994, Vol. 35, 101-111

SUMMARY

Technical Problem

A method for treating or preventing diabetic nephropathy and retinal vascular diseases such as diabetic retinopathy is not established, and the establishment of the treatment method or prevention method is an urgent issue. Non-existence of appropriate non-human model animals causes the difficulty in establishing an effective treatment method and an effective prevention method, for example. Non-human model animals that have been reported do not show symptoms similar to those of human diabetic nephropathy and human retinal vascular diseases such as human diabetic retinopathy. In particular, non-human model animals of a type of retinal vascular disease that leads to retinal edema caused by increased vascular permeability have not been reported.

Accordingly, the present disclosure was achieved to provide a non-human model animal of a retinal vascular disease that can favorably show symptoms similar to those of human retinal vascular diseases such as human diabetic retinopathy, and a method for producing the non-human model animal. Specifically, the present disclosure was achieved to provide a non-human model animal of a retinal vascular disease that can be used to develop a method for treating, preventing, or diagnosing a retinal vascular disease and to elucidate the onset mechanism and pathology of a retinal vascular disease, and a method for producing the non-human model animal. In particular, the present disclosure was achieved to provide a non-human model animal that can be favorably used to establish a method for treating, preventing, or diagnosing retinal edema, which causes highly impaired vision, and a method for producing the non-human model animal. Furthermore, the present disclosure was achieved to provide a method for screening a drug for treating and preventing a retinal vascular disease, the method using a non-human model animal.

Solution to Problem

As a result of performing intensive studies to solve the above-mentioned problems, the inventors of the present disclosure focused on Akt protein, which is a serine/threonine kinase, in order to induce symptoms similar to those of human retinal vascular diseases in non-human animals. When Akt was persistently activated in retinal blood vessels in their incipient stage, it was confirmed that the blood vessels increased in their diameter with varicose deformity, the extension of the blood vessels was delayed, and vascular permeability increased. Based on these findings, the inventors succeeded in producing a non-human model animal showing symptoms similar to those of human retinal vascular diseases, and thus achieved the present disclosure.

Specifically, in order to address the foregoing problems, the disclosure including the configurations and methods described in [1] to [10] below is provided.

[1] A non-human model animal of a retinal vascular disease in which constitutively active Akt is expressed.

[2] The non-human model animal of a retinal vascular disease according to [1] above, wherein the constitutively active Akt is constitutively active Akt-Mer.

[3] The non-human model animal of a retinal vascular disease according to [1] above, wherein the expression of the constitutively active Akt is under the control of a Cre-LoxP system.

[4] The non-human model animal of a retinal vascular disease according to any one of [1] to [3] above, wherein the retinal vascular disease is diabetic retinopathy.

[5] The non-human model animal of a retinal vascular disease according to any one of [1] to [4] above, wherein the retinal vascular disease shows at least one symptom selected from retinal edema, retinal hemorrhage, a retinal microaneurysm, and retinal vascular expansion.

With the configurations described in [1] to [5], a non-human model animal of a retinal vascular disease showing symptoms similar to those of human retinal vascular diseases such as human diabetic retinopathy can be provided. Retinal hemorrhage, the structure of a microaneurysm, and the like in the non-human model animal of a retinal vascular disease with these configurations are similar to those of pathological specimens of human diabetic retinopathy, and, in particular, a non-human model animal capable of reproducing the symptoms of retinal edema caused by increased vascular permeability for which no effective treatment method is currently present can be provided. Therefore, the non-human model animal of a retinal vascular disease with these configurations can be favorably used as a research material for searching for a method for treating, preventing, or diagnosing a retinal vascular disease, for the pathologic analysis of a retinal vascular disease, and the like. Furthermore, the degree of severity can be controlled in the non-human model animal of a retinal vascular disease with these configurations, and therefore, a treatment method, prevention method, or diagnosis method appropriate for the degree of progress of symptoms can be searched for, and, in addition, the non-human model animal can be favorably used as a research material for the pathologic analysis of the disease such as the onset and progress of the disease, and the like.

In particular, with the configurations described in [2] and [3] above, the Akt activity of the constitutively active Akt can be controlled by 4-hydroxytamoxifen and Cre recombinase. Therefore, a non-human model animal showing symptoms similar to those of a desired human retinal vascular disease can be provided through a simple artificial manipulation. Since the degree of severity of a retinal vascular disease or the like can be controlled, it is possible to provide a non-human model animal of a retinal vascular disease that can be particularly favorably used as a research material for searching for a treatment method, prevention method, or diagnosis method appropriate for the degree of progress of symptoms, for the pathologic analysis of the disease such as the onset and progress of the disease, and the like. With the configuration described in [4] above, it is possible to provide a non-human model animal that can be favorably used as a research material for searching for a method for treating, preventing, or diagnosing diabetic retinopathy, for the pathologic analysis of diabetic retinopathy, and the like. With the configuration described in [5] above, a non-human model animal showing the symptoms specific to retinal vascular diseases can be provided. In particular, a non-human model animal capable of reproducing the symptoms of retinal edema caused by increased vascular permeability for which no effective treatment method is currently present can be provided.

[6] A method for producing a non-human model animal of a retinal vascular disease, including:
  a step of producing a transgenic non-human animal into which a construct including a DNA coding for constitutively active Akt so as to enable Akt activity to be controlled by an artificial manipulation is introduced; and
  a step of inducing a retinal vascular disease by controlling the Akt activity of the constitutively active Akt.

[7] The method for producing a non-human model animal of a retinal vascular disease according to [6] above, wherein the constitutively active Akt is constitutively active Akt-Mer, and the Akt activity of the constitutively active Akt is controlled through administration of 4-hydroxytamoxifen to the transgenic non-human animal.

[8] The method for producing a non-human model animal of a retinal vascular disease according to [7] above, wherein the 4-hydroxytamoxifen is administered at a dose of 5 to 50 μg/g weight/day during a desired period between the first day and the fourteenth day after birth.

[9] The method for producing a non-human model animal of a retinal vascular disease according to [6] above,
  wherein the expression of the constitutively active Akt is under the control of a Cre-LoxP system,
  the transgenic non-human animal is produced by introducing a construct in which a DNA coding for the constitutively active Akt is arranged in a state in which the expression of the constitutively active Akt is inhibited due to intervention of the LoxP sequence, and
  the Akt activity of the constitutively active Akt is controlled by mating the transgenic non-human animal with a transgenic non-human animal in which a Cre recombinase is expressed in a vascular specific manner or time specific manner to obtain an offspring in which the Cre recombinase can be expressed or the activity of the Cre recombinase can be induced in a vascular specific manner or time specific manner in cells including the construct.

With the methods described in [6] to [8] above, a non-human model animal of a retinal vascular disease showing symptoms similar to those of human retinal vascular diseases such as human diabetic retinopathy can be produced. Retinal hemorrhage, the structure of a microaneurysm, and the like in the non-human model animal produced using these methods are similar to those of pathological specimens of human diabetic retinopathy, and, in particular, the symptoms of retinal edema caused by increased vascular permeability for which no effective treatment method is currently present can be reproduced. The non-human model animal of a retinal vascular disease produced using these methods can show the symptoms of a human retinal vascular disease in a very short time after the Akt activity of the constitutively active Akt is controlled. Therefore, these methods can be favorably used in the fields of a search for a method for treating, preventing, or diagnosing a retinal vascular disease, the pathologic analysis of the state of a retinal vascular disease, and the like. Furthermore, the degree of severity in the non-human model animal produced using these methods can be controlled by artificially manipulating the Akt activity of the constitutively active Akt, and therefore, the non-human model animal can be used very favorably as a research material for searching for a treatment method, prevention method, or diagnosis method appropriate for the degree of progress of symptoms, particularly for the pathologic analysis of the disease such as the onset and progress of the disease, and the like.

In particular, with the methods described in [7] to [9] above, the Akt activity of the constitutively active Akt can be controlled by 4-hydroxytamoxifen and Cre recombinase. Therefore, a non-human model animal showing symptoms similar to those of a desired human retinal vascular disease can be provided through a simple artificial manipulation. Since the degree of severity of a retinal vascular disease or the like can be controlled, the non-human model animal can be particularly favorably used as a research material for searching for a treatment method, prevention method, or diagnosis method appropriate for the degree of progress of symptoms, for the pathologic analysis of the disease such as the onset and progress of the disease, and the like.

[10] A method for screening a drug for treating or preventing a retinal vascular disease, comprising:
  a step of administering a test substance to the non-human model animal of a retinal vascular disease according to any one of [1] to [5] above; and
  a step of determining a treatment effect or a prevention effect of the test substance.

With the method described in [10] above, it is possible to provide a method for screening a drug for treating or preventing a retinal vascular disease, the method using a non-human model animal showing symptoms similar to those of human retinal vascular diseases. Since a non-human model animal showing symptoms similar to those of human retinal vascular diseases is used, the treatment effect and prevention effect of the test substance can be determined with high reliability. Since the degree of severity of a retinal vascular disease or the like can be controlled by controlling the Akt activity of the constitutively active Akt, a treatment drug and a prevention drug appropriate for the symptoms can be developed. Furthermore, the screening method can be favorably used for the development of treatment drugs and prevention drugs for retinal vascular diseases leading to retinal edema caused by increased vascular permeability for which no effective treatment method is currently present. Therefore, the screening method is expected to significantly contribute to the development in techniques for treating and preventing retinal vascular diseases.

BRIEF DESCRIPTION OF DRAWINGS

FIG. 2 discloses SEQ ID NOS 28-29, respectively, in order of appearance.

DESCRIPTION OF EMBODIMENTS

Figure 1:
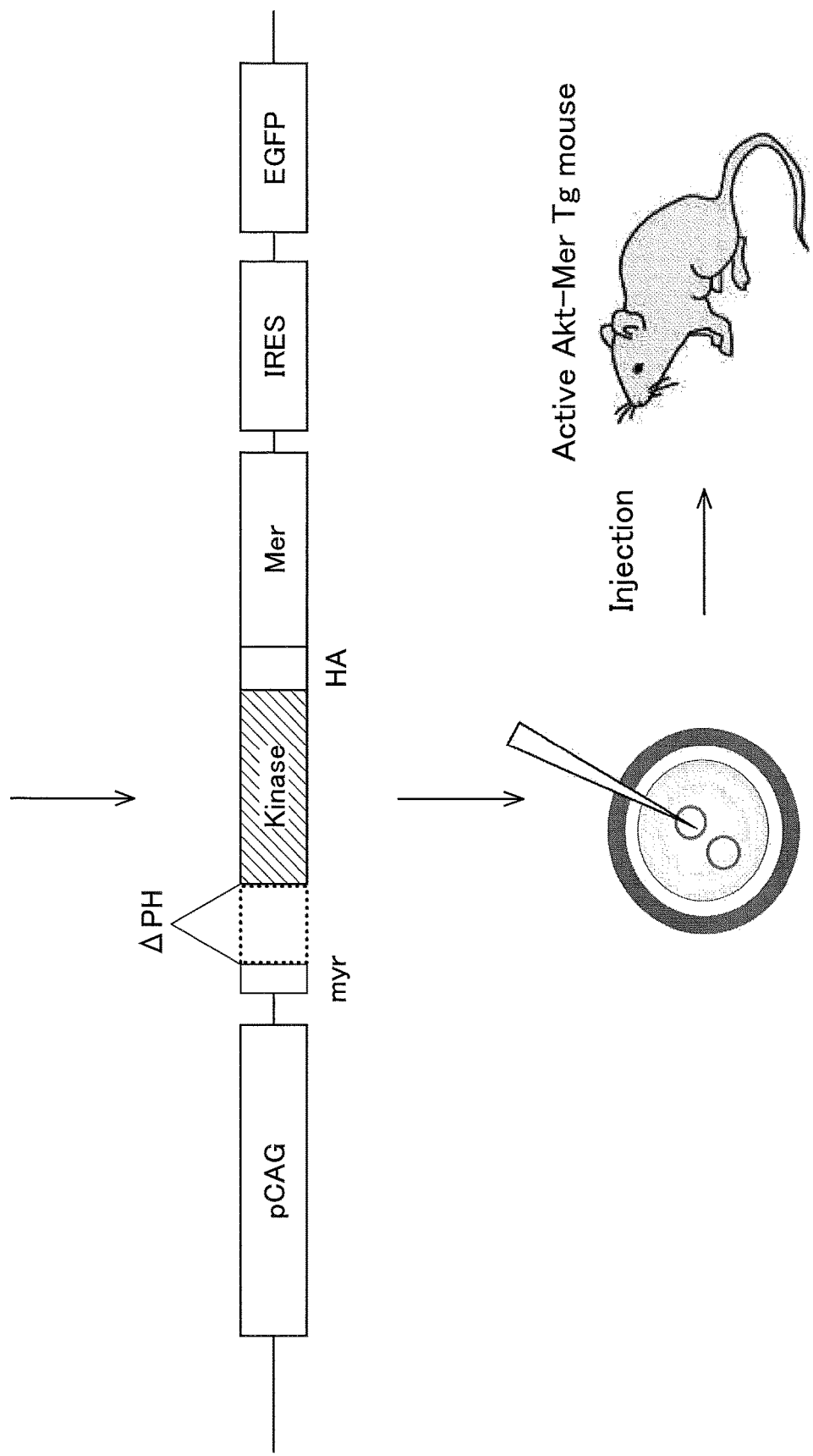
FIG. 1 is a schematic diagram illustrating the construction of a non-human transgenic animal in which constitutively active Akt-Mer is expressed in Example 1.

Hereinafter, embodiments of the present disclosure will be described in detail. However, the present disclosure is not limited to the embodiments described below.

(Non-Human Model Animal)
(Non-Human Model Animal of Retinal Vascular Disease)

A non-human model animal according to this embodiment relates to a non-human model animal of a retinal vascular disease showing the pathology of a retinal vascular disease. In the non-human model animal of a retinal vascular disease according to this embodiment, constitutively active Akt is expressed.

A mammalian animal other than a human is used for the non-human model animal of a retinal vascular disease according to this embodiment, and there is no particular limitation on the species. Examples thereof include rodents such as mice, guinea pigs, hamsters, and rats, rabbits, dogs, cats, monkeys, sheep, pigs, cows, and horses. Mice are preferable.

Regarding the non-human model animal of a retinal vascular disease according to this embodiment, the "retinal vascular disease" collectively refers to ocular diseases caused by pathological changes such as hemorrhage, effusion, aneurysm, edema, ischemia, and infarct that occur in at least part of retinal blood vessels. Representative cases of the retinal vascular diseases are diabetic retinopathy, retinopathy of prematurity, and retinal venous occlusion. The retinal vascular diseases also include Coats' disease and the like. The non-human model animal of a retinal vascular disease according to this embodiment is targeted for all the cases.

Diabetic retinopathy is one of the diabetic complications and is caused by microvascular disorder occurring in the retina due to a continuous hyperglycemic state. Diabetic retinopathy can be classified into three stages, namely simple retinopathy, preproliferative retinopathy, and proliferative retinopathy, for example, depending on the degree of severity. The non-human model animal of a retinal vascular disease according to this embodiment is targeted for all the cases. In simple retinopathy, microvascular walls are damaged, leading to microaneurysms, petechial retinal hemorrhage, and the like. Specifically, the retinal microvascular walls are weakened through the degeneration of vascular endothelial cells, the decidualization and degeneration of perithelial cells, and the thickening of basement membranes, and petechial hemorrhage thus occurs due to the formation and breakage of microaneurysms. In preproliferative retinopathy, partial microvascular occlusion causes an ischemic portion. In proliferative retinopathy, new blood vessels are formed in order to compensate the retinal ischemic state, and extend to the retinal surface and the vitreous body. New blood vessels are weak due to their immaturity and thus easily break and bleed. In addition, a fibrous proliferative membrane that is also referred to as "proliferative tissue" is formed, and pulls the retina locating therearound, leading to detached retina. Then, irrespective of the degree of severity, blood plasma accumulates in the retina due to an increase in microvascular permeability caused by the formation of retinal microaneurysms and the like, leading to retinal edema.

Retinal venous occlusion is caused by the occlusion of the retinal veins, and includes central retinal venous occlusion caused by the occlusion of the central retinal vein, and branch retinal venous occlusion caused by the occlusion of veins located on the peripheral side with respect to the central retinal vein. The non-human model animal of a retinal vascular disease according to this embodiment is targeted for both cases. In the early stage, an increase in a venous perfusion pressure and the stasis of the blood flow causes retinal hemorrhage and edema. In the chronic stage, retinal edema remains due to the expansion or meandering of capillaries located around the blocked veins and the formation of aneurysms. Severe venous occlusion causes retinal ischemia, and pathological angiogenesis is induced as in other retinal vascular diseases, leading to detached retina.

Retinopathy of prematurity is caused by the immaturity of retinal blood vessels observed in low-birth-weight infants and premature infants born before 37 weeks gestation. Retinopathy of prematurity is classified into type I, which progresses mildly, and type II, which progresses rapidly. Type I is classified into five stages depending on the degree of severity. The non-human model animal of a retinal vascular disease according to this embodiment is targeted for both cases. Type I is classified into five stages depending on the degree of severity. At a first stage, tissues called boundaries are formed at the leading ends of blood vessels that are extending from the optic papilla toward the periphery thereof. At a second stage, vascular proliferation accompanied with fibrous components occurs, and the thicknesses of the boundaries increase. At a third stage, fibrovascular proliferative tissues protrude toward the vitreous body and extends. At a fourth stage and a fifth stage, the surrounding retina is pulled due to the contraction of the fibrovascular proliferative tissues that have increased on the vitreous body side, and is thus detached. At all the stages, the expansion of retinal veins and the meandering of arteries are considered to be signs of aggravation. In type II, retinal blood vessels significantly expand and meander, and the state of the disease does not progress in a stepwise manner and rapidly leads to detached retina.

Examples of the funduscopic findings of such retinal vascular diseases include a microaneurysm, localized hemorrhage such as retinal petechial hemorrhage, retinal ecchymosis, and retinal splinter hemorrhage, hard exudate, retinal edema, retinal thickening, soft exudate, venous disorder, retinal microvascular disorder, retinal and papillary angiogenesis, preretinal and vitreous hemorrhage, a fibrovascular proliferative membrane, and detached retina.

The non-human model animal of a retinal vascular disease according to this embodiment shows one or more of the above-mentioned symptoms. For example, a stereoscopic microscope or a fluorescence microscope can be used to confirm retinal edema, retinal hemorrhage, a retinal microaneurysm, the retinal vascular expansion and the like in the non-human model animal of a retinal vascular disease according to this embodiment. Fluorescence micrographs showing vascular endothelial cells or the like stained through immunostaining or the like can be preferably used to confirm retinal vascular disorder and the like. For example, the non-human model animal a retinal vascular disease according to this embodiment is characterized by the formation of 50 or more microaneurysms, and preferably 80 or more microaneurysms, per retina, or the vascular diameter that is expanded by a factor of 1.5, and particularly preferably a factor of 2 or more, compared with normal retinal blood vessels. Moreover, retinal edema or the like can be preferably confirmed by measuring dye leaking from blood vessels, the thickness of the retina, or the like. For example, the non-human model animal of a retinal vascular disease according to this embodiment is characterized by the thickness of the retina that is 1.2 times or more, and particularly preferably 1.5 times or more, larger than the thickness of a normal retina.

Akt, which is also referred to as "protein kinase B", is a serine/threonine kinase including a PH (Plekstrin homology) domain at the N-terminus, and is known as an important intracellular signaling factor. Akt is activated in a PI3 kinase dependent manner, and phosphorylates various intracellular substrates. The inventors of the present disclosure reported a technique of controlling the Akt activity (kinase activity) to maintain the pluripotency of stem cells and differentiate stem cells as desired (see JP 2005-304487A).

Akt is universally present in any higher animal cells. For example, Akt is conserved in various organisms from yeast to Caenorhabditis elegans, Drosophila, and mammalian animals (see Fabrizio P. et al., Science 2001 Apr. 13: 292(5515): 288-290. Epub 2001 Apr. 5 for yeasts; Paradis S. et al., Genes Dev. 1998 Aug. 15: 12(16): 2488-98 for Caenorhabditis elegans; and Staveley BE. et al., Curr. Biol. 1998 May 7: 8(10): 599-602 for Drosophila). Akt is ubiquitously expressed in various tissues of mammalian animals (see Altomare D. A. et al., Oncogene 11: 1055-1060; Altomare, D. A. et al., Oncogene 116: 2407-2411; Brodbeck D. et al., J. Biol. Chem. 274: 9133-9136; and Nakatani K. et al., Biochem. Biophys. Res. Commun. 257: 906-910).

There is no particular limitation on constitutively active Akt expressed in the non-human model animal of a retinal vascular disease according to this embodiment as long as the Akt activity is constitutively activated. The constitutively active Akt may be derived from any higher animal. Moreover, the constitutively active Akt may be derived from the species that is the same as or different from the non-human animal in which the expression is induced. Akt is preferably derived from a human.

It is known that human-derived Akt includes three isoforms, namely Akt-1, Akt-2, and Akt-3, and the amino acid sequences of these isoforms have very high homology. An example of wild-type human Akt is human wild-type Akt-1 (Accession No. AH011307 or NM_001014432), which is coded for by the base sequence of Sequence ID. No. 3 or Sequence ID No. 5 and consists of the amino acid sequence of Sequence ID. No. 4 or Sequence ID No. 6. In addition, examples thereof include human wild-type Akt-2 (Accession No. NM_001626), which is coded for by the base sequence of Sequence ID No. 7 and consists of the amino acid sequence of Sequence ID No. 8, and human wild-type Akt-3 (Accession No. NM_181690), which is coded for by the base sequence of Sequence ID No. 9 and consists of the amino acid sequence of Sequence ID No. 10. However, there is no limitation thereto, and Akt may have an amino acid sequence with at least a certain ratio of sequence identity with respect to the above-mentioned amino acid sequences, or an amino acid sequence obtained by modifying the above-mentioned amino acid sequences with at least one modification of deletion, substitution, and addition of one or several amino acids, and have the above-mentioned Akt properties.

Phosphorylation at two positions, namely threonine at position 308 (Thr-308) and serine at position 473 (Ser-473), is required to activate Akt-1, phosphorylation at two positions, namely threonine at position 309 (Thr-309) and serine at position 474 (Ser-474), is required to activate Akt-2, and phosphorylation at two positions, namely threonine at position 305 (Thr-305) and serine at position 472 (Ser-472), is required to activate Akt-3. Phosphorylation in the Akt family is controlled on the downstream side of PI3 kinase. Specifically, the PH domain of Akt binds to PI(3,4,5)P3 or the like produced by PI3 kinase, and Akt is thus transferred to the cell membrane. The above-mentioned positions of Akt are phosphorylated by PDK1 and the mTORC2 complex near the cell membrane, and Akt is thereby activated.

The constitutively active Akt includes Akt in which the above-mentioned positions relating to the activation are phosphorylated. Examples thereof include wild-type human Akt-1 in which Thr-308 and Ser-473 are constitutively phosphorylated, wild-type human Akt-2 in which Thr-309 and Ser-474 are constitutively phosphorylated, and wild-type human Akt-3 in which Thr-305 and Ser-472 are constitutively phosphorylated. Amino acid residues to be phosphorylated in Akt-1 are preferably a Thr residue located at a position corresponding to position 308 and a Ser residue located at a position corresponding to position 473 when Sequence ID No. 4 or Sequence ID No. 6 is used as a reference sequence. The same applies to amino acid residues to be phosphorylated in Akt-2 and Akt-3.

An example of the constitutively active Akt is Akt in which a membrane localization signal sequence is added to the N-terminus or C-terminus. Preferable examplse of the constitutively active Akt include wild-type Akt in which the PH domain at the N-terminus is deleted and a myristoylation signal is added to the N-terminus instead, and wild-type Akt in which a myristoylation signal is added to the N-terminus. Akt with a myristoylation signal is of a constitutive membrane-bound type. This type of Akt is constitutively phosphorylated by kinase present on the cell membrane and is brought into a state in which the Akt activity (kinase activity) is activated. The myristoylation signal sequence preferably includes a Met-Gly-Xaa-Xaa-Xaa-Ser/Ala/Thr/Phe-Xaa-Xaa-Xaa motif (Xaa is any amino acid) (Sequence ID No. 11) from its N-terminus (see Utsumi T. et al., The Journal of Biological Chemistry 276(13): 10505-10513 and the like). For example, the N-terminal myritoylation signal sequences (MGSSKSKPKDPSQR (Sequence ID No. 12) and MGSSKSKPKDPSQRRRRIRT (Sequence ID No. 13)) derived from c-Src and the like can be used as the myristoylation signal sequence, but there is no limitation thereto.

Furthermore, constitutively active Akt mutants such as a mutant obtained by substituting glutamic acid at position 40 (Glu-40) of wild-type human Akt-1 with lysine (Lys) (also abbreviated as "E40K-Akt-1" hereinafter) and a mutant obtained by substituting glutamic acid at position 17 (Glu-17) of wild-type human Akt-1 with lysine (Lys) (also abbreviated as "E17K-Akt-1" hereinafter) may also be used. In the same manner, Akt mutants obtained from wild-type human Akt-2 and wild-type human Akt-3 can include mutants having the above-mentioned substitution, namely E40K or E17K. Such mutants can be obtained by screening the natural world or using a gene cloning technique. For example, such mutants can be obtained by using a known mutagenesis technique, and specifically, such mutants can be obtained by inserting a mutation site into a nucleic acid molecule coding for wild-type Akt. There is no particular limitation on the method for inserting a mutation site, and a mutagenesis technique for producing a mutant protein that is known in the art can be used. Examples thereof include known mutagenesis techniques such as site-directed mutagenesis, PCR mutagenesis that uses a PCR or the like to introduce mutation, and transposon insertion mutagenesis. A commercially available mutagenesis kit (e.g., QuikChange (registered trademark) Site-directed Mutagenesis Kit (manufactured by Stratagene)) may also be used.

Amino acid residues to be substituted in Akt-1 are preferably a Glu residue located at a position corresponding to position 40 and a Glu residue located at a position corresponding to position 17 when Sequence ID No. 4 or Sequence ID No. 6 is used as a reference sequence. The substitution positions can be determined based on an alignment between the amino acid sequence of Akt-1 with a different sequence and the amino acid sequence of Akt-1 disclosed in Sequence ID No. 4 or Sequence ID No. 6. In the same manner, amino acid residues to be substituted in Akt-2 and Akt-3 can also be determined using Sequence ID No. 8 and Sequence ID No. 10 as reference sequences. Therefore, the constitutively active Akt mutants may have an amino acid sequence with at least a certain ratio of sequence identity with respect to the above-mentioned amino acid sequences, or an amino acid sequence obtained by modifying the above-mentioned amino acid sequences with at least one modification of deletion, substitution, and addition of one or several amino acids, and have the above-mentioned properties of the constitutively active Akt, as long as the amino acid at the above-mentioned substitution position is substituted.

For example, the constitutively active Akt includes a protein coded for by a nucleic acid molecule consisting of the base sequence of Sequence ID No. 1, and its amino acid sequence is represented by Sequence ID No. 2. However, there is no limitation thereto, and the constitutively active Akt may have an amino acid sequence with at least a certain ratio of sequence identity with respect to the amino acid sequence of Sequence ID No. 2, or an amino acid sequence obtained by modifying the amino acid sequence of Sequence ID No. 2 with at least one modification of deletion, substitution, and addition of one or several amino acids, and have the above-mentioned properties of the constitutively active Akt.

Here, "at least a certain ratio of sequence identity" means preferably having 70%, 75%, 80%, or at least 85% sequence identity, more preferably having at least 90% sequence identity, and particularly preferably 95%, 96%, 97%, 98%, or at least 99% sequence identity.

Such variants can be obtained by screening the natural world or using a gene cloning technique. When an amino acid sequence is modified, a person skilled in the art can easily predict a modification with which the above-mentioned characteristics can be maintained. Specifically, from the viewpoint of maintaining the protein structure, an amino acid whose properties including polarity, electric charge, hydrophilicity, hydrophobicity and the like are similar to those of an amino acid to be substituted can be used in an amino acid substitution, for example. Such substitution is well known to a person skilled in the art as a conservative substitution. Specifically, alanine, valine, leucine, isoleucine, proline, methionine, phenylalanine, and tryptophan are all classified into non-polar amino acids and thus have similar properties, for example. Examples of non-charged amino acids include glycine, serine, threonine, cysteine, tyrosine, asparagine, and glutamine. Examples of acidic amino acids include aspartic acid and glutamic acid. Examples of basic amino acids include lysine, arginine, and histidine. Substitution of amino acids in the same group is allowable because the functions of a protein can be maintained.

It is preferable that the kinase activity of the constitutively active Akt expressed in the non-human model animal of a retinal vascular disease according to this embodiment can be controlled by an artificial manipulation. Examples of the constitutively active Akt whose Akt activity can be controlled by an artificial manipulation include a fusion protein in which constitutively active Akt is coupled to a protein that can adjust the Akt activity with a stimulation from the outside of a living organism in an in-frame manner, constitutively active Akt coexpressed with a protein that can adjust the Akt activity with a stimulation from the outside of a living organism, and a protein that is coded for by a DNA including a DNA coding for constitutively active Akt and a sequence capable of controlling the expression of the DNA coding for constitutively active Akt freely with the action of a site-directed recombinant protein or the like, but there is no limitation thereto. Preferable examples of the constitutively active Akt include active Akt-Mer and constitutively active Akt whose expression is under the control of the Cre-LoxP system, which will be described later.

The constitutively active Akt-Mer, which is an example of the constitutively active Akt, is a fusion protein in which constitutively active Akt is coupled to a modified estrogen receptor (Mer) in an in-frame manner, and a tag sequence may also be inserted between the constitutively active Akt and the Mer. An example of the tag sequence is HA that uses a peptide sequence of hemagglutinin, which is a glycoprotein present on the surface of influenza virus, but there is no limitation thereto.

Mer is a modified estrogen receptor, and does not bind to endogenous estrogen, but binds to 4-hydroxytamoxifen (abbreviated as "4-DHT" hereinafter), which is an artificially synthesized estrogen derivative. Mer binds to a heat shock protein (abbreviated as "Hsp" hereinafter) 90 in the absence of 4-OHT, and is deactivated due to the active site being masked by Hsp 90. However, the masking of Hsp is released in the presence of 4-OHT, and the constitutively active Akt is activated. The Akt activity of the constitutively active Aid to which Mer is coupled in the above-mentioned manner can be freely controlled by 4-OHT.

An example of Mer is a protein coded for by the base sequence of Sequence ID No. 14, and its amino acid sequence is represented by Sequence ID No. 15. However, there is no limitation thereto, and Mer may have an amino acid sequence with at least a certain ratio of sequence identity with respect to the amino acid sequence of Sequence ID No. 15, or an amino acid sequence obtained by modifying the amino acid sequence of Sequence ID No. 15 with at least one modification of deletion, substitution, and addition of one or several amino acids, and have the above-mentioned properties of Mer. Here, "at least a certain ratio of sequence identity" means preferably having 70%, 75%, 85%, or at least 80% sequence identity, more preferably having at least 90% sequence identity, and particularly preferably 95%, 96%, 97%, 98%, or at least 99% sequence identity.

With such a configuration, in the non-human model animal of a retinal vascular disease according to this embodiment, the constitutively active Akt-Mer is expressed, and the Akt activity of the constitutively active Akt is activated in the presence of 4-OHT. The non-human model animal of a retinal vascular disease according to this embodiment thus shows symptoms similar to those of human retinal vascular diseases.

Examples of the constitutively active Akt whose expression is under the control of the Cre-LoxP system, which is an example of the constitutively active Akt, include expression products of DNAs obtained by arranging, in the same direction or opposite directions, a Cre recognition sequence such as a LoxP sequence on the upstream side and downstream side of a DNA coding for the above-mentioned constitutively active Akt. A further example thereof is an expression product of a DNA obtained by arranging the Cre recognition sequences such as the LoxP sequences so as to sandwich a transcription termination sequence or the like and arranging a promoter sequence on the upstream side thereof and a DNA coding for constitutively active Akt on the downstream side thereof.

There is no particular limitation on the DNA coding for constitutively active Akt as long as the DNA codes for constitutively active AKT having the above-mentioned properties. Examples thereof include a DNA having the base sequence of Sequence ID No. 1 coding for constitutively active Akt in which the PH domain of wild-type Akt is deleted and the myristoylation signal is added to the N-terminus instead, and a DNA coding for the amino acid sequence of Sequence ID No. 2 corresponding to the base sequence of Sequence ID No. 1. However, there is no limitation thereto, and the DNA coding for constitutively active Akt may be a DNA having a base sequence with at least a certain ratio of sequence identity with respect to the base sequence of Sequence ID No. 1, a base sequence obtained by modifying the base sequence of Sequence ID No. 1 with at least one modification of deletion, substitution, and addition of one or several bases, or a base sequence that hybridizes to a base sequence complementary to the base sequence of Sequence ID No. 1 under a stringent condition, as long as the DNA codes for a protein having the above-mentioned properties of active Akt.

Here, "at least a certain ratio of sequence identity" means preferably having 70%, 75%, 85%, or at least 85% sequence identity, more preferably having at least 90% sequence identity, and particularly preferably 95%, 96%, 97%, 98%, or at least 99% sequence identity.

The "stringent condition" refers to a condition including the following hybridization condition and washing condition.

Hybridization Condition
  Hybridization in a hybridization solution (100 mM Tris-HCl pH8.0, 1 M NaCl, 10 mM EDTA, 0.2 mM bovine serum albumin, 0.2% Ficoll 400, 0.2% polyvinylpyrrolidone, 100 μg/ml salmon sperm DNA) at 65° C. overnight (at least 16 hours).
Washing Condition
  Washing with a washing solution (0.2×SSC (6.67 mM NaCl, 6.67 mM trisodium citrate dihydrate pH7.0, 0.1% SDS)) at 65° C. for 30 minutes, which is repeated twice.

The Cre/LoxP system is a site-directed recombination reaction system in which bacteriophage P1 Cre recombinase (abbreviated as "Cre" hereinafter) acts on the above-mentioned specific DNA sequence called a LoxP sequence. Here, Cre is a site-directed DNA recombination enzyme, which is a member of a phage λ integrase family.

An example of the LoxP sequence is ataacttcgtataatgtatgctatacgaagttat (Sequence ID No. 16). The sequence of Sequence ID No. 16, which is shown as an example of the LoxP sequence, includes 34 bp, namely inverted repeats (Cre binding domain) of 13 bp on both ends and a region of 8 bp located therebetween. For Cre recognition and a site-directed homologous recombination reaction, which will be described below, it is sufficient that 8 to 10 bases in each of the 13-bp Cre binding domain in the LoxP sequence are identical to those in the sequence of Sequence ID No. 16. In addition, it is required that the region of 8 bp sandwiched between the Cre binding domains has at least a certain ratio of sequence identity with respect to that in the sequence of Sequence ID No. 16.

Therefore, the LoxP sequence is not limited to the sequence of Sequence ID. No. 16, and may have a configuration in which at least 8 to 10 bases of 13 bp at both ends are identical to those in the base sequence of Sequence ID No. 16 and the region of 8 bp sandwiched between the Cre binding domains has at least a certain ratio of sequence identity, or may have a base sequence obtained by modifying the base sequence of Sequence ID No. 16 with at least one modification of deletion, substitution, and addition of one or several bases, as long as it has the properties of a LoxP sequence, which will be described below. Here, "at least a certain ratio of sequence identity" means preferably having 70%, 80%, or at least 90% sequence identity.

When the two LoxP sequences are located extending in the same direction, Cre recognizes the LoxP sequences, and the sequence located between the LoxP sequences is cut out. On the other hand, when the two LoxP sequences are located extending in the opposite directions, Cre recognizes the LoxP sequences, and the sequence located between the LoxP sequences is inverted with respect to the sequences located outside the LoxP sequences. That is, Cre is an enzyme that recognizes the LoxP sequences, and when the two LoxP sequences are located extending in the same direction, Cre catalyzes cutting out the sequence between the LoxP sequences, whereas when the two LoxP sequences are located extending in the opposite directions, Cre catalyzes a reaction of inverting the sequence between the LoxP sequences. An example of Cre is a protein coded for by the base sequence of Sequence ID No. 17, and its amino acid sequence is represented by Sequence ID No. 18. However, there is no limitation thereto, and Cre may have an amino acid sequence with at least a certain ratio of sequence identity with respect to the amino acid sequence of Sequence ID No. 18, or an amino acid sequence obtained by modifying the amino acid sequence of Sequence ID No. 18 with at least one modification of deletion, substitution, and addition of one or several amino acids, and have the above-mentioned properties of Cre. Here, "at least a certain ratio of sequence identity" means preferably having 70%, 75%, 85%, or at least 85% sequence identity, more preferably having at least 90% sequence identity, and particularly preferably 95%, 96%, 97%, 98%, or at least 99% sequence identity.

With such a configuration, in the non-human model animal of a retinal vascular disease according to this embodiment, the Akt activity of the constitutively active Akt can be controlled using a site-directed recombination reaction by the Cre/LoxP system. When the constitutively active Akt is activated, the non-human model animal of a retinal vascular disease according to this embodiment shows the above-mentioned symptoms of a retinal vascular disease. Specifically, when the two LoxP sequences are located extending in the same direction, the base sequence coding for the constitutively active Akt that is arranged to extend in the regular direction is maintained in an activated state in the absence of Cre, whereas the base sequence coding for the constitutively active Akt is cut out in the presence of Cre, leading to the deactivation of the constitutively active Akt. On the other hand, when the two LoxP sequences are located extending in the opposite directions, the base sequence coding for the constitutively active Akt is arranged to extend in the opposite direction, and, in this state, the constitutively active Akt is maintained in a deactivated state in the absence of Cre, whereas the constitutively active Akt is maintained in an activated state in the presence of Cre due to the base sequence coding for the constitutively active Akt being inverted.

Furthermore, a preferable example of the constitutively active Akt whose expression is under the control of the Cre-LoxP system, which is an example of the constitutively active Akt, is a protein coded for by a DNA obtained by arranging, in the same direction, the LoxP sequences on the upstream side and downstream side of a base sequence such as a transcription termination sequence that suppresses the expression of a DNA coding for constitutively active Akt, and arranging a promoter sequence that induces the constitutive expression of the DNA coding for constitutively active Akt on the upstream side of the upstream LoxP sequence and the DNA coding for constitutively active Akt on the downstream side of the downstream LoxP sequence. With such an arrangement, when Cre recognizes the LoxP sequences, the base sequence that suppresses the expression of the DNA coding for constitutively active Akt is cut out, and the DNA coding for constitutively active Akt is brought under the control of the promoter sequence. The DNA coding for constitutively active Akt is thus expressed, and the constitutively active Akt is maintained in an activated state. The non-human model animal of a retinal vascular disease according to this embodiment thus shows the above-mentioned symptoms of a retinal vascular disease.

Furthermore, in addition to the Cre/LoxP system, a combination of another site-directed DNA recombination enzyme and another site-directed DNA recombination enzyme recognition sequence, such as an Flp/FRT system or a Rox/Dre system, can also be used.

The non-human model animal of a retinal vascular disease according to this embodiment shows symptoms similar to those of human retinal vascular diseases such as human diabetic retinopathy. A non-human model animal can be provided in which retinal hemorrhage, the structure of a microaneurysm, and the like are similar to those of pathological specimens of human diabetic retinopathy, and, in particular, the symptoms of retinal edema caused by increased vascular permeability for which no effective treatment method is currently present can be reproduced. Therefore, the non-human model animal of a retinal vascular disease according to this embodiment can be favorably used as a research material for searching for a method for treating, preventing, or diagnosing a retinal vascular disease, for the pathologic analysis of a retinal vascular disease, and the like. Furthermore, the degree of severity can be controlled in the non-human model animal of a retinal vascular disease according to this embodiment, and therefore, a treatment method, prevention method, or diagnosis method appropriate for the degree of progress of symptoms can be searched for, and, in particular, the non-human model animal can be favorably used as a research material for the pathologic analysis of the disease such as the onset and progress of the disease, and the like.

(Non-Human Model Animal of Diabetic Retinopathy)

A non-human model animal according to this embodiment relates to a non-human model animal of diabetic nephropathy showing the symptoms of diabetic nephropathy. In the non-human model animal of diabetic nephropathy according to this embodiment, constitutively active Akt is expressed.

Diabetic nephropathy is one of diabetic complications and is caused by microvascular disorder in the glomeruli of the kidneys due to a continuous hyperglycemic state. A continuous hyperglycemic state causes sclerotic lesions in the capillaries included in the glomeruli, and the glomeruli cannot perform the original function, namely filtration of waste products, due to the destruction or occlusion of the capillaries, leading to the deterioration of the renal functions. Examples of the histological findings of diabetic nephropathy include the thickening of glomerular basement membranes, diffuse lesions or nodal lesions due to the expansion of mesangiums, exudative lesions, microstructural failures of mesangiums such as fusion and microaneurysms, glomerular hypertrophy, microvascular proliferation in the glomerular hyla, global, ischemic or segmental glomerular sclerosis, glomerular changes such as changes of glomerular epithelial cells and glomerular endothelial cells, the thickening of renal tubular basement membranes, the atrophy of renal tubules, the expansion or fibrosis of renal tubular stromata, changes in renal tubules or renal tubular stromata such as cellular infiltration, changes in juxtaglomerular apparatuses such as the expansion of juxtaglomerular apparatuses and the infiltration of T cells, and microangiogenesis at vascular poles. Examples of clinical findings include microalbuminuria, overt albuminuria, persistent proteinurea, edema, hypertension, and renal failure. The non-human model animal of diabetic nephropathy according to this embodiment shows one or more of the above-mentioned histological findings and clinical findings.

It should be noted that, regarding the non-human model animal of diabetic nephropathy according to this embodiment, the non-human animal used and the constitutively active Akt are as described in the section of the non-human model animal of a retinal vascular disease according to this embodiment.

The non-human model animal of diabetic nephropathy according to this embodiment shows symptoms similar to those of human diabetic nephropathy and can be favorably used as a research material for searching for a method for treating, preventing, or diagnosing diabetic nephropathy, for the pathologic analysis of diabetic nephropathy, and the like.

(Method for Producing Non-Human Model Animal)
(Method for Producing Non-Human Model Animal of Retinal Vascular Disease)

A method for producing a non-human model animal according to this embodiment relates to a method for producing a non-human model animal of a retinal vascular disease showing symptoms similar to those of human retinal vascular diseases. The method for producing a non-human model animal of a retinal vascular disease according to this embodiment includes a step of producing a transgenic non-human animal into which a construct including a DNA coding for constitutively active Akt so as to enable the Akt activity to be controlled by an artificial manipulation is introduced (step of producing a transgenic non-human animal), and a step of inducing a retinal vascular disease by controlling the Akt activity of the constitutively active Akt (step of inducing a retinal vascular disease). Hereinafter, each step will be described in detail.

(Step of Producing Transgenic Non-Human Animal)

A construct including a DNA coding for constitutively active Akt so as to enable the Akt activity to be controlled by an artificial manipulation is introduced into a transgenic animal in which constitutively active Akt is expressed.

The "transgenic non-human animal" means a non-human animal having an exogenous gene at an individual level by artificially introducing the exogenous gene at an early stage of development, and its offspring having that exogenous gene. A type of non-human animal used in the method for producing a non-human model animal of a retinal vascular disease according to this embodiment is as described in the section of the non-human model animal according to this embodiment.

The DNA coding for constitutively active Akt is as described in the section of the non-human model animal of a retinal vascular disease according to this embodiment, and examples thereof include a DNA having the base sequence of Sequence ID No. 1 coding for constitutively active Akt in which the PH domain of wild-type Akt is deleted and the myristoylation signal is added to the N-terminus instead, and a DNA coding for the amino acid sequence of Sequence ID No. 2 corresponding to the base sequence of Sequence ID No. 1. However, there is no limitation thereto, and the DNA coding for constitutively active Akt includes a DNA having a base sequence with at least a certain ratio of sequence identity with respect to the base sequence of Sequence ID No. 1, a base sequence obtained by modifying the base sequence of Sequence ID No. 1 with at least one modification of deletion, substitution, and addition of one or several bases, or a base sequence that hybridizes to a base sequence complementary to the base sequence of Sequence ID No. 1 under a stringent condition, as long as the DNA codes for a protein having the properties of constitutively active Akt described in the section of the non-human model animal of a retinal vascular disease according to this embodiment.

The construct including a DNA coding for constitutively active Akt may also include a known base sequence that is necessary to express the functions of the DNA coding for constitutively active Akt. Examples thereof include a promoter sequence, a leader sequence, and a signal sequence. Examples of the promoter sequence include the EF1α promoter, the CAG promoter, the SRα promoter, the SV40 promoter, the LTR promoter, the CMV (cytomegalovirus) promoter, the RSV (Rous sarcoma virus) promoter, the MoMuLV (Moloney murine leukemia virus) LTR, and the HSV-TK (herpes simplex virus thymidinekinase) promoter. In particular, the EF1α promoter, the CAG promoter, the MoMuLV LTR, the CMV promoter, the SRa promoter, and the like are preferable.

The construct including a DNA coding for constitutively active Akt may also include an enhancer, a poly-A addition signal, a selective marker gene, an SV40 replication origin, and the like as desired in addition to a promoter. Examples of the selective marker gene include a dihydrofolate reductase gene, a neomycine resistance gene, and a puromycin resistance gene.

The construct including a DNA coding for constitutively active Akt may also include a reporter gene for confirming the expression of constitutively active Akt. There is no particular limitation on the reporter gene as long as the reporter gene can be used to confirm the expression of constitutively active Akt, and a known reporter gene can be used. Examples thereof include a fluorescent protein gene, a luciferase gene, and a β-galactosidase gene. The fluorescent protein gene is preferable, and a green fluorescent protein (abbreviated as "GFP" hereinafter) and variants of GFP such as an enhanced green fluorescent protein (abbreviated as "EGFP" hereinafter) can be used. Furthermore, the reporter gene may also be coupled to the DNA coding for constitutively active Akt via an IRES (internal ribosome entry site), a sequence coding for a self-cleaving peptide, or the like.

An expression vector incorporating a construct is constructed, for example, for the introduction of the construct. Here, a vector can be used that allows the construct including a DNA coding for constitutively active Akt to be introduced into a target host and allows the constitutively active Akt to be expressed in the host. Therefore, the vector includes at least one restriction enzyme site sequence into which the construct including a DNA coding for constitutively active Akt can be inserted. In addition, it is preferable that the vector includes a drug resistance marker or the like for confirming the introduction of the construct. Examples of the vector include pCMV-Tag, pAdEasy, and pCMVLacI, but there is no limitation thereto.

In the step of producing a transgenic non-human animal, the construct including a DNA coding for constitutively active Akt so as to enable the Akt activity to be controlled by an artificial manipulation is introduced into a non-human animal. Thus, the Akt activity of the constitutively active Akt can be freely controlled by an artificial manipulation. Examples of such introduction of the construct including a DNA coding for constitutively active Akt so as to enable the Akt activity to be controlled by an artificial manipulation include introduction of a construct including a chimeric DNA obtained by coupling a DNA coding for constitutively active Akt and a DNA coding for a protein that can freely adjust the Akt activity with a stimulation from the outside of a living organism in an in-frame manner, cointroduction of a construct including a DNA coding for constitutively active Akt and a construct including a DNA coding for a protein that can freely adjust the Akt activity of the constitutively active Akt with a stimulation from the outside of a living organism, and introduction of a construct including a DNA coding for constitutively active Akt and a sequence capable of controlling the expression of the DNA coding for constitutively active Akt freely with the action of a site-directed recombinant protein or the like. Preferable examples include introduction of a construct including a chimeric DNA coding for constitutively active Akt-Mer, and introduction of a construct including a DNA coding for constitutively active Akt whose expression is under the control of the Cre-LoxP system.

The constitutively active Akt-Mer is a fusion protein of constitutively active Akt and Mer as described in the section of the non-human model animal of a retinal vascular disease according to this embodiment. Examples of the DNA coding for Mer include a DNA having the base sequence of Sequence ID No. 14 and a DNA coding for the amino acid sequence of Sequence ID No. 15. However, there is no limitation thereto, and the DNA coding for Mer may be a DNA having a base sequence with at least a ratio of sequence identity with respect to the base sequence of Sequence ID No. 14, a base sequence obtained by modifying the base sequence of Sequence ID No. 14 with at least one modification of deletion, substitution, and addition of one or several bases, or a base sequence that hybridizes to a base sequence complementary to the base sequence of Sequence ID No. 14 under a stringent condition, as long as the DNA codes for a protein having the above-mentioned properties of Mer. Here, "at least a certain ratio of sequence identity" means preferably having 70%, 75%, 85%, or at least 85% sequence identity, more preferably having at least 90% sequence identity, and particularly preferably 95%, 96%, 97%, 98%, or at least 99% sequence identity. The "stringent condition" is as described above.

Therefore, there is no particular limitation on the DNA coding for constitutively active Akt-Mer as long as the DNA codes for the above-mentioned fusion protein of constitutively active Akt and Mer in an in-frame manner. A DNA coding for a tag sequence may also be inserted between the DNA coding for constitutively active Akt and the DNA coding for Mer.

Examples of the DNA coding for constitutively active Akt whose expression is under the control of the Cre-LoxP system include a DNA obtained by arranging, in the same direction or opposite directions, LoxP sequences on the upstream side and downstream side of a DNA coding for constitutively active Akt described in the section of the non-human model animal of a retinal vascular disease according to this embodiment, and a DNA obtained by arranging, in the same direction, the LoxP sequences on the upstream side and downstream side of a base sequence such as a transcription termination sequence that suppresses the expression of a DNA coding for constitutively active Akt, and arranging a promoter sequence that induces the constitutive expression of the DNA coding for constitutively active Akt on the upstream side of the upstream LoxP sequence and the DNA coding for constitutively active Akt on the downstream side of the downstream LoxP sequence. The base sequence of the DNA coding for constitutively active Akt is as described above.

There is no particular limitation on the method for introducing a construct into a non-human animal as long as a desired construct can be introduced stably. Preferable examples of the method for introducing a construct including a DNA coding for constitutively active Akt include microinjection, retrovirus infection, and adenovirus infection.

In common microinjection using a mouse, a fertilized egg is collected from an oviduct of a female mouse that has been subjected to natural mating or artificial insemination, and a construct including a desired DNA is injected into the male pronucleus of this fertilized egg using a microcapillary or the like, for example. There is no particular limitation on the form of the construct to be injected, but the construct preferably has a linear shape or an annular shape. A fertilized egg into which the construct has been injected is introduced into an oviduct of a pseudopregnant mouse (adoptive parent), and an offspring mouse is obtained after the parent mouse is raised for a predetermined period of time. It is confirmed whether or not the chromosome of the offspring mouse incorporates the desired DNA, and the individual incorporating the desired DNA is selected. In addition, a phyletic line can be established by obtaining the offspring. When the introduced construct includes a reporter sequence, the incorporation of the DNA can be confirmed depending on the type of reporter sequence. For example, when a fluorescent protein or the like is included, the incorporation of the DNA can be confirmed through the observation of the fluorescence in the tail of the offspring mouse. Moreover, the incorporation of the DNA may also be confirmed by using a PCR, Southern hybridization, or the like to analyze a DNA extracted from the tail or the like of the offspring mouse.

Moreover, examples of the method for introducing the construct including a DNA coding for constitutively active Akt so as to enable the Akt activity to be controlled by an artificial manipulation also include use of embryonic stem cells (referred to as "ES cells" hereinafter). When embryonic stem cells are used, a transgenic non-human animal can be produced in the same manner by introducing a desired DNA into ES cells in advance and returning these ES cells into blastocytes, for example. There is no particular limitation on the method for introducing a desired DNA into ES cells as long as a desired DNA can be introduced stably, but examples thereof include electroporation, a calcium phosphate method, a DEAE-dextran method, and lipofection.

In a method for introducing a construct including a DNA coding for constitutively active Akt whose expression is under the control of the Cre-LoxP system to obtain a transgenic non-human animal into which constitutively active Akt under the control of the Cre-LoxP system is introduced, it is preferable that a construct including a promoter sequence is introduced into the ROSA26 locus (target locus) in ES cells through homologous recombination to produce an allele from which the constitutively active Akt gene is not transcribed. An example of the above-mentioned construct including a promoter sequence is a construct in which a promoter sequence, a Cre recognition sequence, a transcripition termination sequence, a Cre recognition sequence, and a DNA coding for constitutively active Akt are arranged in this order from the 5' side to the 3' side. The above-mentioned promoter sequences can be used, and the CAG promoter is particularly preferable. There is no particular limitation on the Cre recognition sequence, but the conventionally known LoxP sequence can be used, for example. It is preferable that a sequence coding for a selective marker is located at a position between the Cre recognition sequences and on the upstream side of the transcription termination sequence in order to confirm the introduction of the construct into ES cells. There is no particular limitation on the selective marker, and examples thereof include a drug resistance marker, a fluorescent protein marker, an enzyme marker, and cell surface receptor marker. The construct is introduced into ES cells based on the above-mentioned conventionally known method such as electroporation, and homologous recombination of the promoter region including the ROSA26 transcription initiation point in the genome of an ES cell is performed. Then, the cells into which the construct has been introduced are cultured, and a strain in which the selective maker is expressed is selected. This strain in which the selective marker is expressed is an ES cell strain having a modified allele into which the above-mentioned construct has been introduced through homologous recombination. When the selective marker is a drug resistance marker, for example, it is sufficient that a drug resistant strain is selected. In the recombinant ES cell strain having this modified allele, the constitutively active Akt gene is not transcribed due to the intervention of the selective marker such as a drug resistance marker and the transcription termination sequence in the construct introduced into the ROSA 26 gene. Next, after the obtained recombinant ES cells are injected into blastocytes, the blastocytes are returned to the womb of a pseudopregnant non-human animal. Then, a chimeric non-human animal born therefrom is mated with a wild-type non-human animal, and a non-human animal having the modified allele (F1, heterozygote) is thus obtained. When the hetero non-human animals are mated with each other, a non-human animal (F2, homozygote) having homo modified alleles can be obtained. The genotype of the non-human animal can be confirmed using a conventionally known method such as Southern blotting.

(Step of Inducing Retinal Vascular Disease)

A retinal vascular disease is induced by activating, by an artificial manipulation, the constitutively active Akt introduced into the transgenic non-human animal. The introduced constitutively active Akt is activated depending on its form.

When the constitutively active Akt is constitutively active Akt-Mer, 4-OHT can be used to control the activation. Therefore, when 4-OHT is administered to the transgenic non-human animal in which the constitutively active Akt-Mer is expressed, the constitutively active Akt is activated, and symptoms similar to those of human retinal vascular diseases, which are described in the section of the non-human model animal of a retinal vascular disease according to this embodiment, are thus induced.

There is no particular limitation on the administration form of 4-OHT as long as the symptoms of a retinal vascular disease are induced, and the administration form can be selected depending on the type of non-human animal to be used, the degree of severity of the induced retinal vascular disease, or the like. Examples thereof include intraperitoneal administration, oral administration, intravenous administration, intraarterial administration, intramuscular administration, subcutaneous administration, intracutaneous administration, intrarectal administration, intraocular administration, tracheobronchial administration, intranasal administration, intraoral administration, sublingual administration, intraventricular administration, intradural administration, epidural administration, enteral administration, dermal administration, and inhalation, but there is no limitation thereto. Intraperitoneal administration is preferable.

There is no limitation on the dose, administration period, and administration frequency of 4-OHT as long as the symptoms of a retinal vascular disease is induced, and they can be determined as appropriate depending on the type of non-human animal to be used, the degree of severity of the induced retinal vascular disease, the administration route, or the like. 4-OHT may be administered continuously or intermittently. 4-OHT may be administered a plurality of times, and in this case, doses may be the same or different. For example, 4-OHT can be administered to the transgenic non-human animal in which the constitutively active Akt-Mer is expressed at a dose of 5 to 50 μg/g weight/day during a desired period between the first day and the fourteenth day after birth, and preferably at a dose of 10 to 100 μg/day×3 days from the fourth day to the sixth day after birth. It should be noted that the weight of the mice used in examples, which will be described below, was about 2 to 4 g on the seventh day after birth. Moreover, with the above-mentioned administration conditions, the symptoms of a retinal vascular disease are significantly shown after the seventh day after birth of the transgenic non-human animal in which the constitutively active Akt-Mer is expressed, but the number of days required for the induction of the symptoms of a retinal vascular disease can be controlled by changing the administration conditions as appropriate.

For example, in the examples, which will be described later, when 100 μg of 4-OHT was intraperitoneally administered to a transgenic non-human animal in which constitutively active Akt-Mer was expressed once per day from the fourth day to the sixth day after birth, and the shapes of the retinal blood vessels were observed on the seventh day after birth, the symptoms such as retinal hemorrhage, a swollen retina, and the obvious formation of microaneurysms were observed, and the overall retinal blood vessels significantly expanded. In human diabetic retinopathy, retinal hemorrhage and edema are found irrespective of the degree of severity. When 10 μg of 4-OHT, which is one tenth of the dose in the above-described case, was administered, and the shapes of the retinal blood vessels were observed on the seventh day after birth, the symptoms such as the formation of microaneurysms, which were milder than those observed in the case of the administration of 100 μg of 4-OHT, were observed. It was confirmed that the observed microaneurysms each had a plurality of nuclei and were formed of clustered endothelial cells. These microaneurysms are similar to the pathological specimens of microaneurysms, which have been reported, derived from human retinal vascular diseases such as human diabetic retinopathy.

On the other hand, in an animal in which constitutively active Akt-Mer was not expressed, and an animal in which constitutively active Akt-Mer was expressed and to which 4-OHT was not administered, vascular disorder was not observed compared with normal retinal blood vessels. Therefore, it is revealed that retinal vascular disorder similar to that in human retinal vascular diseases such as diabetic retinopathy can be reproduced in the non-human model animal by controlling the Akt activity by an artificial manipulation. In addition, symptoms similar to those of human retinal vascular diseases can be induced in very short time after the administration of 4-OHT.

The degree of severity of a retinal vascular disease can be controlled by adjusting the dose and administration period of 4-OHT to adjust the activated state of Akt. Enhancing the activated state of Akt makes it possible to provide a non-human model animal that significantly shows the symptoms of a retinal vascular disease, and the non-human model animal can be particularly favorably used for researches to elucidate the onset mechanism and the pathology of a retinal vascular disease. The expression of the symptoms of a retinal vascular disease can be reduced by lowering the activated state of Akt, and thus a non-human model animal showing symptoms more similar to those of human retinal vascular diseases can be provided. In particular, a non-human model animal showing symptoms similar to those of retinal vascular diseases leading to retinal edema caused by increased vascular permeability can be provided.

When the expression of the constitutively active Akt is under the control of the Cre-LoxP system, Cre can control the Akt activity of the constitutively active Akt. There is no limitation on the introduction of Cre into the transgenic non-human animal into which the constitutively active Akt under the control of the Cre-LoxP system has been introduced, but Cre can be introduced by mating this transgenic non-human animal with a transgenic non-human animal into which a DNA coding for Cre has been introduced and in which Cre is expressed. For example, the transgenic non-human animal into which the constitutively active Akt under the control of the Cre-LoxP system produced as described above is introduced is mated with a female (or male) transgenic non-human animal in which Cre is expressed. Here, the transgenic non-human animal in which Cre is expressed can be produced using a construct including a DNA coding for Cre arranged on the downstream side of an appropriate promoter sequence. When a fertilized egg produced by the above-mentioned mating inherits a modified allele from the mother, a region including a transcription termination sequence (or a selective marker sequence when the selective marker sequence is included) located between Cre recognition sequences such as LoxP sequences is removed by the catalytic action of expressed Cre in the embryonic cells. Since the transcription termination sequence, which suppresses the transcription of the constitutively active Akt gene, is removed, the irreversible conversion to the modified allele from which the constitutively active Akt gene is constitutively expressed by a promoter such as the CAG promoter is performed.

A transgenic non-human animal in which the expression of Cre can be controlled in a tissue specific manner and a time specific manner can be favorably used as the transgenic non-human animal in which Cre is expressed. For example, when a DNA coding for Cre under the control of a promoter (tissue specific promoter) for a gene that is specifically expressed in a specific tissue is introduced, the expression of Cre can be controlled such that Cre is expressed in a tissue specific manner. Preferable examples of the tissue specific promoter include promoters for genes that are specifically expressed in vascular tissues, particularly in vascular endothelial cells, but there is no limitation thereto. A Tie-Cre non-human animal (mouse) into which a DNA coding for Cre under the control of a promoter for the Tie2 gene, a VE-cad-Cre non-human animal (mouse) into which a DNA coding for Cre under the control of a promoter for the VE cadherin gene, or the like can be used. Here, the Tie2 gene codes for a tyrosine kinase receptor, which is also referred to as "TEK receptor tyrosine kinase", and is known to be expressed specifically in endothelial cells. The VE cadherin, which is also referred to as "cadherin 5" or "CD144", is an adhesive molecule belonging to the cadherin family, and is known to be expressed specifically in endothelial cells. When a DNA coding for Cre under the control of a promoter (time specific promoter) for a gene that is activated only after a non-human animal grows to a certain stage is introduced, the expression of Cre can be controlled such that Cre is expressed in a time specific manner.

A transgenic non-human animal in which the recognition of the Cre recognition sequences by Cre and a site-directed recombination reaction can be inductively controlled by the stimulation from the outside such as a drug can also be favorably used as the transgenic non-human animal in which Cre is expressed. A transgenic non-human animal in which tamoxifen inducible Cre is expressed can be favorably used. For example, a CAG-MerCreMer non-human animal (mouse) into which a construct including a DNA coding for, under the control of the CAG promoter, a fusion protein of Cre and the ligand binding domains (above-described Mer) of the mutant estrogen receptor fused to the N-terminus and the C-terminus of the Cre is introduced (see Egawa G. et al., J Invest Dermatol. 2009: 129(10): 2386-95 and the like) can be used. Furthermore, non-human animals in which Cre is expressed, such as a CreER non-human animal (mouse), a CreERT2 non-human animal (mouse), and a Pdgfb-iCreER non-human animal (mouse) (see Claxton S. et al., Genesis. 2008: 46(2): 74-80 and the like), into which a construct including a DNA coding for a fusion protein of Cre and the ligand binding domain of the mutant estrogen receptor can be used. In general, MerCreMer, CreER, and the like stay in cytoplasm, and are not transferred to the nucleus. However, in the presence of tamoxifen, which is a derivative of estrogen, or a derivative of tamoxifen, MerCreMer, CreER, and the like bind to tamoxifen or a derivative of tamoxifen and are transferred to the nucleus, where they recognize the Cre recognition sequences such as the LoxP sequences and catalyze the site-directed recombination reaction. Using these properties makes it possible to control the action of the Cre-LoxP system in a time specific manner and a tissue specific manner.

Examples of the DNA coding for Cre include a DNA having the base sequence of Sequence ID No. 17 and a DNA coding for the amino acid sequence of Sequence ID No. 18. However, there is no limitation thereto, and the DNA coding for Cre may be a DNA having a base sequence with at least a ratio of sequence identity with respect to the base sequence of Sequence ID No. 17, a base sequence obtained by modifying the base sequence of Sequence ID No. 17 with at least one modification of deletion, substitution, and addition of one or several bases, or a base sequence that hybridizes to a base sequence complementary to the base sequence of Sequence ID No. 17 under a stringent condition, as long as the DNA codes for a protein having the above-mentioned properties of Cre. Here, "at least a certain ratio of sequence identity" means preferably having 70%, 75%, 85%, or at least 85% sequence identity, more preferably having at least 90% sequence identity, and particularly preferably 95%, 96%, 97%, 98%, or at least 99% sequence identity.

As described above, when the expression of the constitutively active Akt is under the control of the Cre-LoxP system, the Akt activity of the constitutively active Akt can be preferably controlled through the mating with a transgenic non-human animal in which Cre is expressed. The Akt activity can be favorably controlled by controlling the expression of Cre and the induction of the activity of Cre in a tissue specific manner or a time specific manner, thus making it possible to control the onset or the degree of severity of a retinal vascular disease. For example, when the induction of the activity of Cre is controlled by the stimulation from the outside such as a drug, a drug in the above-mentioned administration form can be administered. The activated state of Akt can be adjusted by adjusting the dose and administration period of the drug, and the degree of severity of a retinal vascular disease can be thus controlled. Therefore, the dose and administration period of the drug can be changed as appropriate depending on the target degree of severity of a retinal vascular disease, the type of drug to be administered, or the like.

With the method for producing a non-human model animal of a retinal vascular disease according to this embodiment, a non-human model animal showing symptoms similar to those of human retinal vascular diseases such as human diabetic retinopathy can be provided. In the non-human model animal produced using the method for producing a non-human model animal of a retinal vascular disease according to this embodiment, retinal hemorrhage, the structure of a microaneurysm, and the like are similar to those of pathological specimens of human diabetic retinopathy. In particular, the non-human model animal can be provided in which the symptoms of retinal edema caused by increased vascular permeability for which no effective treatment method is currently present can be reproduced. In addition, the non-human model animal of a retinal vascular disease according to this embodiment can show the symptoms of a human retinal vascular disease in short time after the Akt activity of the constitutively active Akt is controlled. Therefore, the method for producing a non-human model animal of a retinal vascular disease according to this embodiment can be favorably used in the fields of a search for a method for treating, preventing, or diagnosing a retinal vascular disease, the pathologic analysis of a retinal vascular disease, and the like. Furthermore, the degree of severity in the non-human model animal produced using the method for producing a non-human model animal of a retinal vascular disease according to this embodiment can be controlled by artificially manipulating the activated state of the Akt activity of the constitutively active Akt. Therefore, a non-human model animal can be provided that can be used very favorably as a research material for searching for a treatment method, prevention method, or diagnosis method appropriate for the degree of progress of symptoms, particularly for the pathologic analysis of the disease such as the onset and progress of the disease, and the like.

(Method for Producing Non-Human Model Animal of Diabetic Nephropathy)

A method for producing a non-human model animal according to this embodiment relates to a method for producing a non-human model animal of diabetic nephropathy showing the symptoms of human diabetic nephropathy. The method for producing a non-human model animal according to this embodiment includes a step of producing a transgenic non-human animal into which a construct including a DNA coding for constitutively active Akt so as to enable the Akt activity to be controlled by an artificial manipulation is introduced (step of producing a transgenic non-human animal), and a step of inducing diabetic nephropathy by controlling the Akt activity of the constitutively active Akt (step of inducing diabetic nephropathy).

The step of producing a transgenic non-human animal can be performed as described in the section of the method for producing a non-human model animal of a retinal vascular disease according to this embodiment. The step of inducing diabetic nephropathy can be performed in accordance with the induction step described in the section of the method for producing a non-human model animal of a retinal vascular disease according to this embodiment, and symptoms similar to those of human diabetic nephropathy, which are described in the section of the non-human model animal of diabetic nephropathy according to this embodiment, are induced.

With the method for producing a non-human model animal of diabetic nephropathy according to this embodiment, a non-human model animal showing symptoms similar to those of human diabetic nephropathy can be provided. Therefore, the method for producing a non-human model animal of diabetic nephropathy according to this embodiment can be favorably used in the fields of a search for a method for treating, preventing, or diagnosing diabetic nephropathy, the pathologic analysis of diabetic nephropathy, and the like.

(Method for Screening Drug for Treatment or Prevention)
(Method for Screening Drug for Treating or Preventing Retinal Vascular Disease)

The non-human model animal of a retinal vascular disease according to this embodiment can be favorably used in a method for screening a drug for treating or preventing a retinal vascular disease, and the embodiment of the present disclosure encompasses this screening method.

The method for screening a drug for treating or preventing a retinal vascular disease according to this embodiment includes a step of administering a test substance to the non-human model animal of a retinal vascular disease according to this embodiment, and a step of determining the treatment effect or prevention effect of the test substance.

There is no particular limitation on the test substance as long as it is expected that the substance has an effect of treating or preventing a retinal vascular disease. Therefore, the test substance may be derived from natural products or may be synthesized artificially. Specific examples thereof include peptides, proteins including enzymes, antibodies and the like, nucleic acids including DNAs, RNAs, iRNAs and the like, peptide nucleic acids, lipids, low-molecular compounds, high-molecular compounds, animal cells, plant cells, animal tissue extract, plant tissue extract, cell culture supernatant, animal plasma, animal serum, microorganisms, and viruses, but there is no limitation thereto. When an artificially synthesized substance is used as a test substance, a compound library, a peptide library, or the like including a plurality of test substances that is produced using a combinatorial chemistry technique can be used as the test substance. There is also no particular limitation on the form of the test substance. Therefore, the administration form may be any of a solid, a semi-solid, and a liquid, and can be determined as appropriate depending on the type of test substance, the administration route, the dose, the administration period, or the like.

The administration route of the test substance is determined as appropriate depending on the type of test substance, the administration period, the dose, or the like, and is not particularly limited. Examples thereof include intraperitoneal administration, oral administration, intravenous administration, intraarterial administration, intramuscular administration, subcutaneous administration, intracutaneous administration, intrarectal administration, intraocular administration, tracheobronchial administration, intranasal administration, intraoral administration, sublingual administration, intraventricular administration, intradural administration, epidural administration, enteral administration, dermal administration, and inhalation, but there is no limitation thereto. The administration period and the dose are also determined as appropriate depending on the type of test substance and the administration route, and are not particularly limited.

The treatment effect or the prevention effect of the test substance is determined by measuring changes in the symptoms of a retinal vascular disease shown in the non-human model animal to which the test substance has been administered, evaluating whether or not the treatment effect or the prevention effect is exhibited, and determining the efficacy of the test substance based on the evaluation results. When the evaluation is performed, the non-human model animals to which the test substance is not administered can be used as a control and compared with a test group to which the test substance is administered. This makes it possible to realize easy evaluation and improve the reliability of the evaluation. There is no limitation on the number of animals included in the test group and control group, but it is preferable that the number of animals is determined such that the reliability of the evaluation is secured.

Any of the above-mentioned findings of a retinal vascular disease such as the shapes of the retinal blood vessels, the thickness of the retina, and the like can be used as the index of the treatment effect or the prevention effect of the test substance, and these findings can be used alone or in combination of two or more as the index.

As a result of the evaluation, it is determined that the test substance has an effect of treating or preventing a retinal vascular disease in the cases where the symptoms of the retinal vascular disease decreases or disappears in the test group when the test group and the control are compared, the progress of the symptoms is delayed, the symptoms do not become severe, the onset of the retinal vascular disease is delayed, and the retinal vascular disease does not appear. It can be determined that such a test substance is a candidate substance useful as a drug for treating or preventing a retinal vascular disease.

The method for screening a drug for treating or preventing a retinal vascular disease according to this embodiment uses, as the non-human model animal, a non-human model animal in which symptoms similar to those of human retinal vascular diseases are reproduced, and therefore, the treatment effect and prevention effect of the test substance can be determined with high reliability. Since the degree of severity of a retinal vascular disease can be controlled by controlling the Akt activity of constitutively active Akt, a treatment drug and a prevention drug appropriate for the symptoms can be developed. The screening method can be favorably used for the development of treatment drugs and prevention drugs for retinal vascular diseases leading to retinal edema caused by increased vascular permeability for which no effective treatment method is currently present. Therefore, the method for screening a drug for treating or preventing a retinal vascular disease according to this embodiment is expected to significantly contribute to the development in techniques for treating and preventing retinal vascular diseases.

(Method for Screening Drug for Treating or Preventing Diabetic Nephropathy)

The non-human model animal of diabetic nephropathy according to this embodiment can be favorably used in a method for screening a drug for treating or preventing diabetic nephropathy, and the embodiment of the present disclosure encompasses this screening method. The method for screening a drug for treating or preventing diabetic nephropathy according to this embodiment can be performed in accordance with the screening method described in the section of the method for screening a drug for treating or preventing a retinal vascular disease according to this embodiment. This makes it possible to search for a candidate substance useful as a drug for treating or preventing diabetic nephropathy.

The method for screening a drug for treating or preventing diabetic nephropathy according to this embodiment uses, as the non-human model animal, a non-human model animal in which symptoms similar to those of human diabetic nephropathy are reproduced, and therefore, the treatment effect and prevention effect of the test substance can be determined with high reliability. Therefore, the method for screening a drug for treating or preventing diabetic nephropathy according to this embodiment is expected to significantly contribute to the development in techniques for treating and preventing diabetic nephropathy.

EXAMPLES

The present disclosure will be more specifically described by use of the following examples, but the present invention is not limited to these examples.

Example 1

Production of Transgenic Mouse in Which Constitutively Active Akt-Mer is Expressed In this example, the production of a transgenic mouse (also referred to as "constitutively active Akt-Mer TG mouse" hereinafter) in which a constitutively active Akt-Mer is expressed and the Akt activity can be reversibly controlled was examined.

Methods

Figure 2:
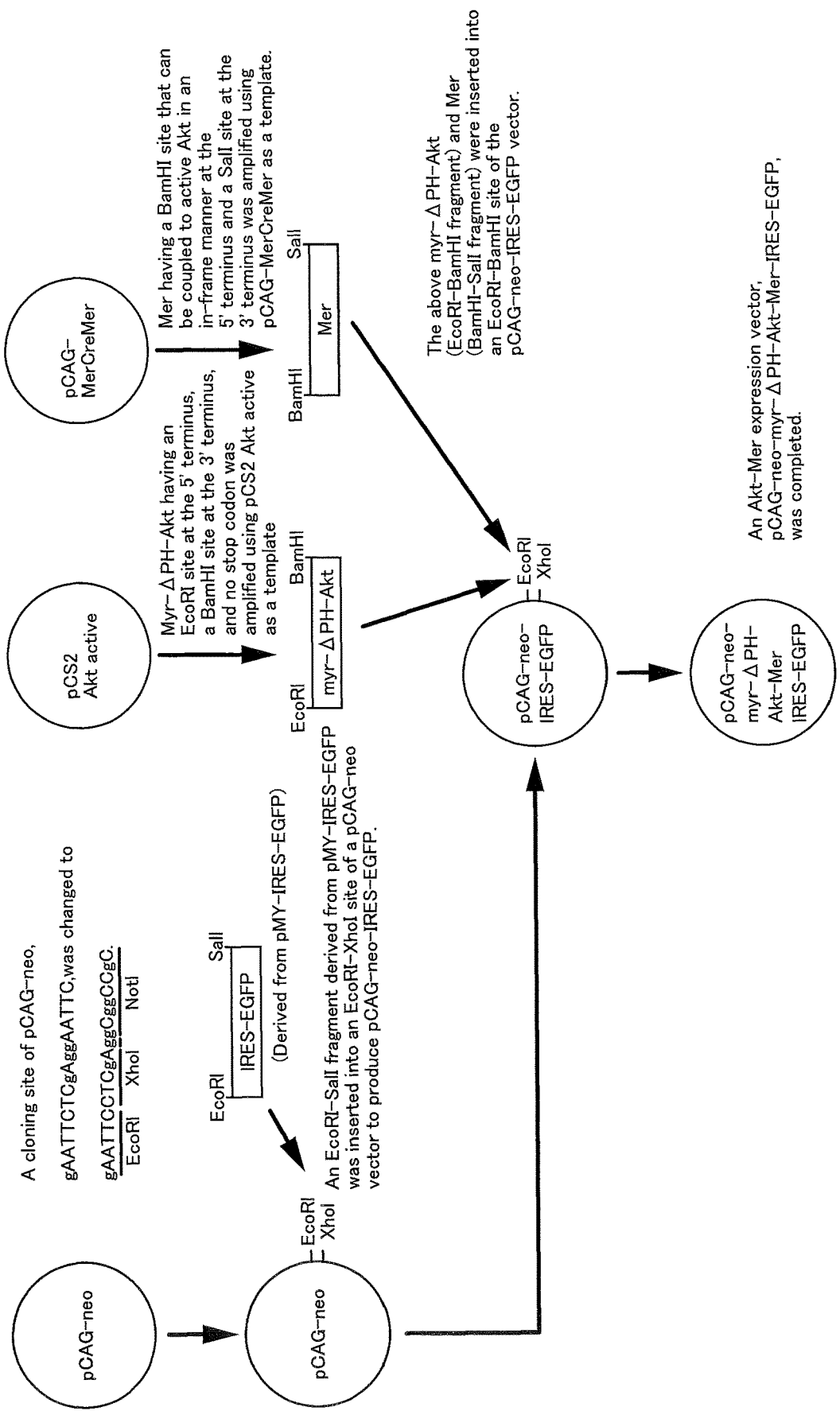
FIG. 2 is a schematic diagram illustrating the construction of an expression vector of constitutively active Akt-Mer in Example 1.

A gene expression plasmid (referred to as "constitutively active Akt-Mer expression vector" hereinaftre) obtained by coupling a chimeric gene coding for constitutively active Akt-Mer and IRES-EGFP (mRNA internal ribosomal entry site—enhanced green fluorescent protein: the base sequence is represented by Sequence ID No. 19) under the control of the CAG promoter was constructed (see JP 2005-304487A). The constructed constitutively active Akt-Mer expression vector was injected into the pronucleus of a fertilized egg of a BDF1 mouse. FIG. 1 is a schematic diagram illustrating the construction of the constitutively active Akt-Mer TG mouse, and FIG. 2 is a schematic diagram illustrating the construction of the constitutively active Akt-Mer expression vector.

Specifically, first, a vector (pCAG-neo-IRES-EGFP vector) was produced by inserting an EcoRI-SalI fragment (corresponding to the IRES-EGFP moiety) derived from pMY-IRES-EGFP (described in Murata K, Kumagai H, Kawashima T, Tamitsu K, Irie M, Nakajima H, Suzu S, Shibuya M, Kamihira S, Nosaka T, Asano S, Kitamura T. The EMBO Journal Vol. 18, pp. 4754-4765, 1999) into a cloning site of a pCAG-neo vector (pCXN vector) (described in Niwa H, Yamamura K, Miyazaki J. Gene. 1991 Dec. 15; 108(2): 193-199.).

```
Subsequently, a PCR was performed using primers
                                    (Sequence ID No. 20)
5'-cggaattcaccatggggagtagcaag-3',
and
                                    (Sequence ID No. 21)
5'-cggaattcggatccagcgtaatctggaacatcgtatgggtaggccgt
gctgctggccgag-3',
``` and a pCS2 Akt active vector (described in Masuyama N, Oishi K, Mon Y, Ueno T, Takahama Y, Gotoh Y. J Biol Chem. 2001 Aug. 31; 276(35): 32799-32805. Epub 2001 Jul. 3.) as a template to amplify a constitutively active Akt cDNA having an EcoRI site at the 5' terminus, a BamHI site at the 3' terminus, and no stop codon.

```
A PCR was performed using primers
                                    (Sequence ID No. 22)
5'-cgggatccggagatccacgaaatgaaatg-3',
and
```

-continued (Sequence ID No. 23)
5'-cgggatccgtcgactcagatcgtgttggggaagcc-3', and a pCAG-MerCreMer vector (described in SCL/tal-1-dependent process determines a competence to select the definitive hematopoietic lineage prior to endothelial differentiation. Endoh M, Ogawa M, Orkin S, Nishikawa S. EMBO J. 2002 Dec. 16; 21(24): 6700-6708) as a template to amplify a Mer cDNA (Mer) having a BamHi site that can be coupled to active Mer in an in-frame manner at the 5' terminus and a SalI site at the 3' terminus.

Next, these two DNA fragments, namely the constitutively active Akt cDNA and the Mer cDNA, were cloned into an EcoRI-XhoI site of the pCAG-neo-IRES-EGFP vector to construct a constitutively active Akt-Mer expression vector, pCAG-neo-myr-ΔPH-Akt-Mer-IRES-EGFP.

Next, the constitutively active Akt-Mer expression vector was introduced into a fertilized egg of a mouse. The vector could be introduced thereinto using any method known in the art. For example, the constitutively active Akt-Mer expression vector was digested using a restriction enzyme PvuI and linearized, and was then purified as appropriate in order to obtain a target fragment. The purified constitutively active Akt-Mer expression vector was inserted into the pronucleus of a fertilized egg of a BDF1 mouse through injection, and the fertilized egg was implanted into the oviduct of a adoptive parent mouse. The adoptive parent mouse was allowed to give birth naturally, and an offspring was obtained. It was confirmed whether or not the constitutively active Akt-Mer expression vector was appropriately introduced into the offspring mouse through the observation of fluorescence in the tail of the offspring mouse. The constitutively active Akt-Mer Tg mouse could be thus obtained.

Example 2

Confirmation of Akt Activity in Retina

With the constitutively active Akt-Mer, the activated state of Akt can be controlled depending on the presence or absence of 4-hydroxytamoxifen (abbreviated as "4-OHT" hereinafter). Therefore, in this example, the Akt activity in the retina of the constitutively active Akt-Mer Tg mouse produced in Example 1 was confirmed.

Methods

To the constitutively active Akt-Mer Tg mouse produced in Example 1, 10 μg/μl 4-OHT was intraperitoneally administered at a dose of 10 μl per day from the fourth day to the sixth day after birth (total dose was 100 μg/day×3 days). On the seventh day after birth, proteins were extracted from the retina removed without performing perfusion fixation, and the Akt phosphorylation was confirmed using Western blotting. A mouse to which 4-OHT was not administered was used as a control and subjected to the same treatment, followed by the confirmation of Akt phosphorylation.

Results

Figure 3:
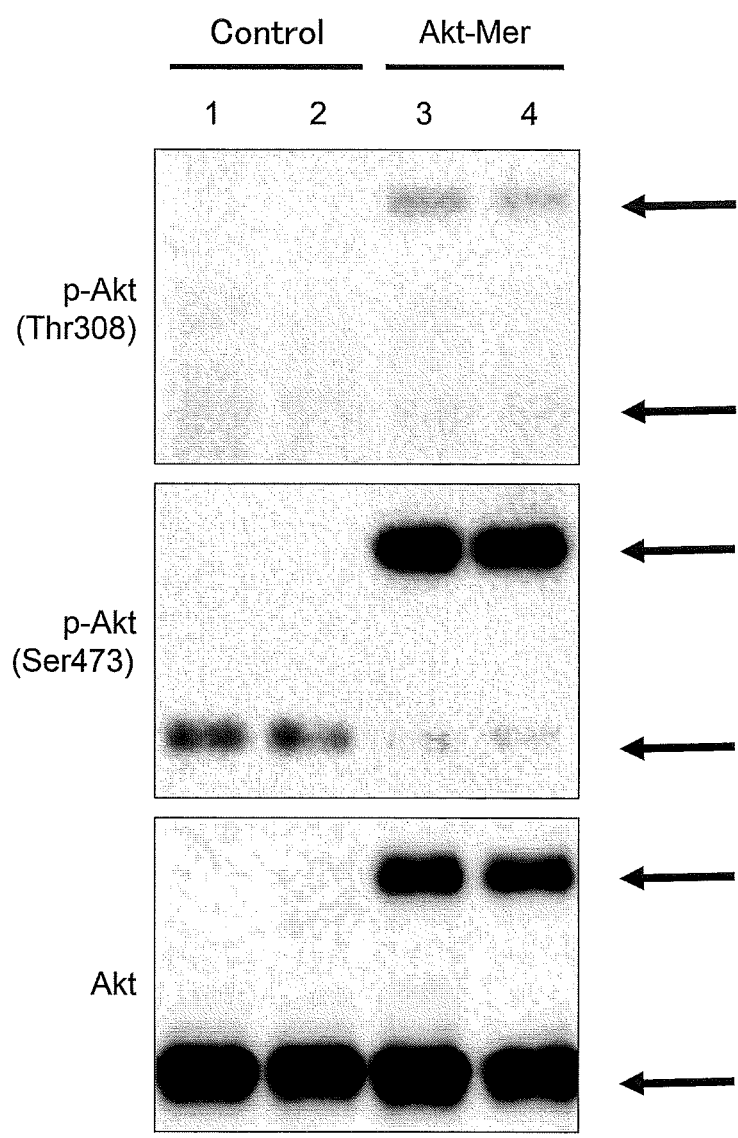
FIG. 3 shows Western blots illustrating the results of the examinations in Example 2 that investigated the Akt activity in retinas.

FIG. 3 shows the results. In each panel in FIG. 3, the upper bands are derived from the introduced constitutively active Akt, and the lower bands are derived from endogenous Akt. It can be confirmed that, in the retina of the constitutively active Akt-Mer Tg mouse (Akt-Mer), Thr-308 and Ser-473 were highly phosphorylated compared with the control. From these results, it can be confirmed that constitutively active Akt was expressed, and it can be understood that the Akt activity was constitutively activated. On the other hand, it can also be confirmed that endogenous Akt was expressed in both the control and the constitutively active Akt-Mer Tg mouse, and part of the endogenous Akt was phosphorylated.

Example 3

Influence of Persistent Activation of Akt on Retina

In this example, an influence of the persistent activation of Akt on the retina in the constitutively active Akt-Mer Tg mouse produced in Example 1 was investigated. Here, the influence on the retina was confirmed by observing the retina of the constitutively active Akt-Mer Tg mouse in which Akt had been persistently activated using an optical microscope.

Methods

To the constitutively active Akt-Mer Tg mouse produced in Example 1, 10 μg/μl 4-OHT was intraperitoneally administered at a dose of 10 μl per day from the fourth day to the sixth day after birth (total dose was 100 μg/day×3 days). On the seventh day after birth, perfusion fixation from the heart was performed using 4% paraformaldehyde (abbreviated as "PFA" hereinafter). Then, a retinal cup was produced from the removed eyeball, and an optical micrograph showing the retina was obtained using MZ16F (Leica). A mouse to which 4-OHT was not administered was used as a control and subjected to the same treatment, and then an image was obtained.

Results

Figure 4:
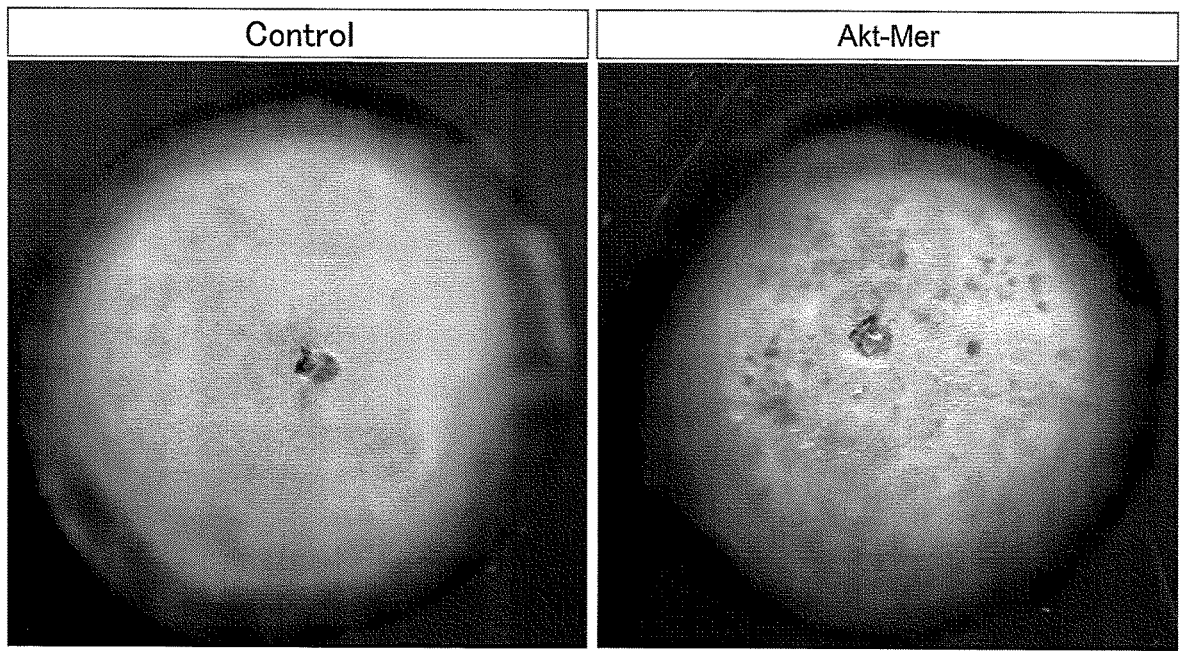
FIG. 4 shows retina cups illustrating the results of the examinations in Example 3 that investigated the influence of the persistent activation of Akt on retinas.

FIG. 4 shows the results. In FIG. 4, small dark gray punctuate changes indicate hemorrhage. In these results, punctuate retinal hemorrhage was observed in the constitutively active Akt-Mer Tg mouse (Akt-Mer) in which Akt was persistently activated through the administration of 4-OHT. Retinal hemorrhage is found in human diabetic retinopathy irrespective of the degree of severity. On the other hand, retinal hemorrhage was not observed in the control, and therefore, it can be understood that the retinal hemorrhage was caused by the persistent activation of Akt.

Example 4

Influence of Persistent Activation of Akt on Retinal Angiogenesis

In this example, an influence of the persistent activation of Akt on the retinal angiogenesis in the constitutively active Akt-Mer Tg mouse produced in Example 1 was investigated. Here, the retina of the constitutively active Akt-Mer Tg mouse in which Akt had been persistently activated was subjected to whole-mount immunostaining and observed.

Methods

To the constitutively active Akt-Mer Tg mouse produced in Example 1, 10 μg/μl 4-OHT was intraperitoneally administered at a dose of 10 μl per day from the fourth day to the sixth day after birth (total dose was 100 μg/day×3 days). On the seventh day after birth, perfusion fixation from the heart was performed using 4% PFA, and then a retinal cup was produced from the removed eyeball. Fluorescent immunostaining using an anti PECAM-1 (platelet endothelial cell adhesion molecule-1: CD31) antibody was performed to stain vascular endothelial cells. Subsequently, a flat-mount image of the retina was obtained using AxioObserver (Zeiss). A mouse to which 4-OHT was not administered was used as a control and subjected to the same treatment, and then an image was obtained.

Results

Figure 5:
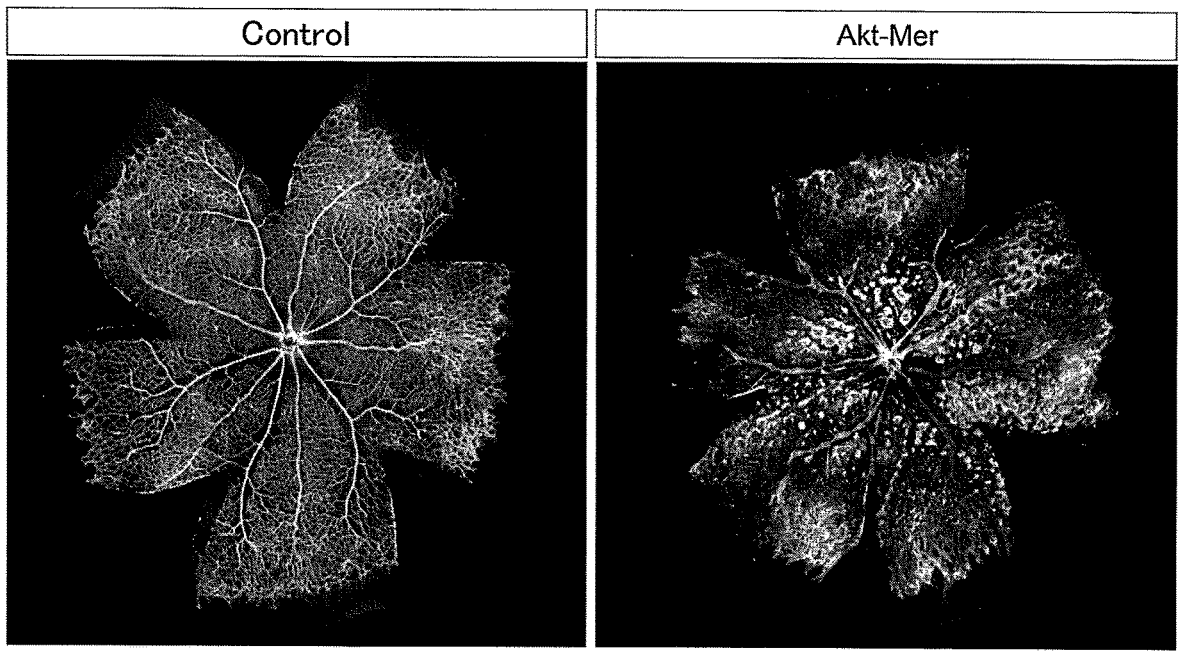
FIG. 5 shows whole-mount immunostaining images of retinas illustrating the results of the examinations in Example 4 that investigated the influence of the persistent activation of Akt on retinal angiogenesis.

FIG. 5 shows the results. Compared with the control, in the constitutively active Akt-Mer Tg mouse (Akt-Mer) in which Akt was persistently activated through the administration of 4-OHT, the formation of a dense vascular network was observed.

Figure 6:
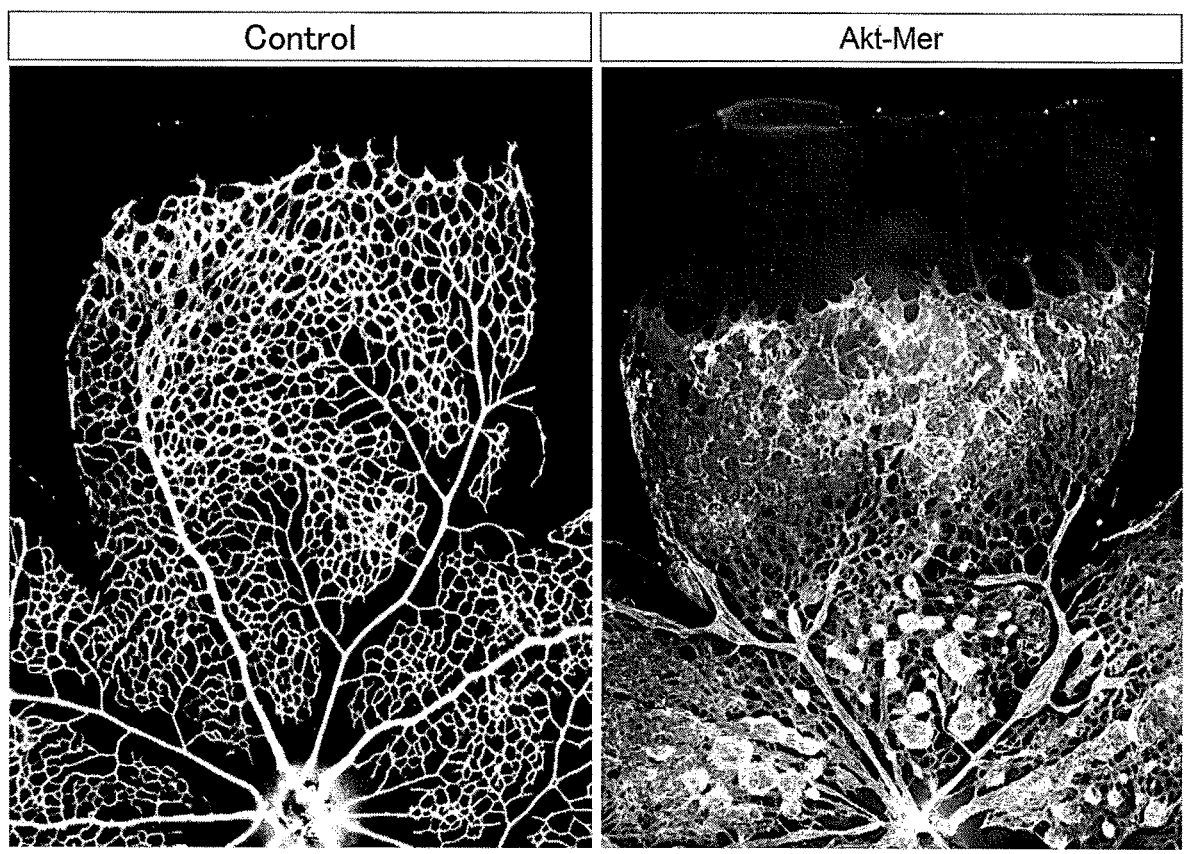
FIG. 6 shows whole-mount immunostaining images of retinas illustrating the results of the examinations in Example 4 that investigated the influence of the persistent activation of Akt on the shapes of retinal capillaries, which are enlarged diagrams of FIG. 5.

For the purpose of investigating the retinal vascular morphology in detail, enlarged diagrams of FIG. 5 are shown in FIG. 6. It can be confirmed that, in the active Akt-Mer Tg mouse (Akt-Mer) in which Akt was persistently activated through the administration of 4-OHT, blood vessels extended from the optic papilla (from the lower end of the diagram) toward the periphery thereof (toward the upper end of the diagram), but the extension of blood vessels was delayed compared with the control. It was observed that the vascular diameters of all of arteries, veins, and capillaries expanded, and thus the overall retinal blood vessels significantly expanded. In addition, it was confirmed that the formation of microaneurysms, which have a varicose structure, was induced. On the other hand, such findings were not confirmed in the control.

Figure 7:
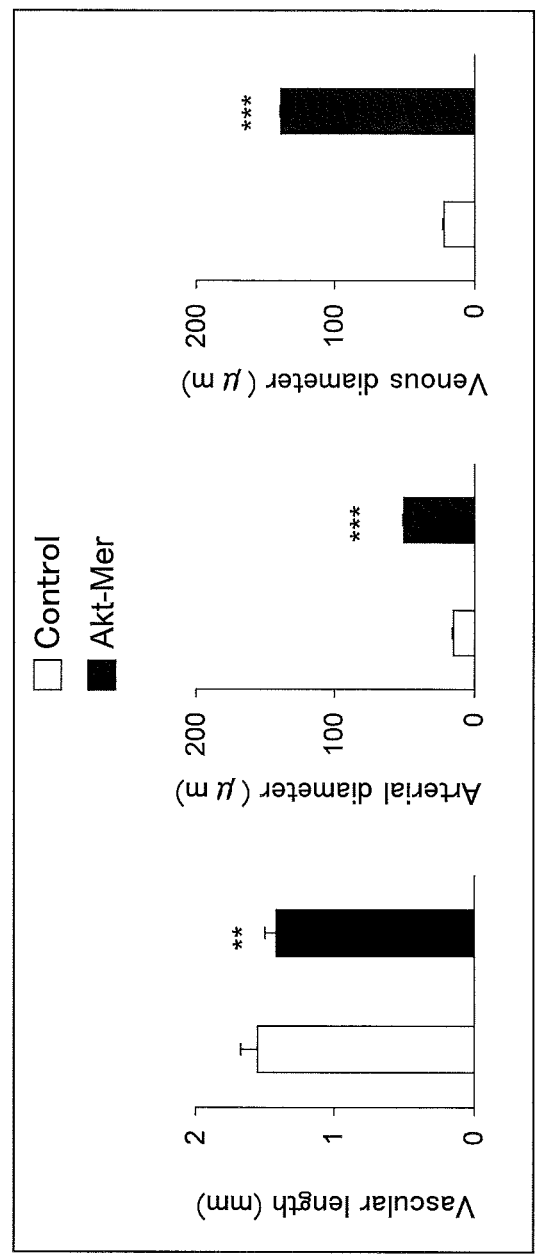
FIG. 7 is a graph showing the measurement results of the extensions of blood vessels (mm), the diameters of arteries (μm), and the diameters of veins (μm), illustrating the results of the examinations in Example 4 that investigated the influence of the persistent activation of Akt on the shapes of retinal capillaries.

For the purpose of further investigating the retinal vascular morphology in detail, the vascular lengths and vascular diameters were measured. Specifically, regarding the vascular lengths, a distance from the peripheral edge of the optic papilla to the leading end of the extending blood vessel along a vein was measured using Photoshop CS5 software. The vascular lengths at four positions in one retina were measured and quantified. Regarding the arterial diameters and venous diameters, the thickness of arteries and veins located on the circumference of a circle with a radius of 1500 μm about the optical papilla was measured also using Photoshop CS5 software (**<0.01). FIG. 7 shows the results. In the constitutively active Akt-Mer Tg mouse (Akt-Mer) in which Akt was persistently activated through the administration of 4-OHT, it was confirmed that the extension of blood vessels was delayed, and the blood vessels significantly expanded. With these results, the findings confirmed in the image of the retina in FIG. 6 are confirmed again.

It is confirmed from the results of this example that the findings such as microaneurysms, the expansion of capillaries, and angiogenesis, which are the findings of retinal vascular diseases such as human diabetic retinopathy, were observed due to the persistent activation of Akt. This reveals that a non-human model animal showing symptoms similar to those of human retinal vascular diseases such as human diabetic retinopathy can be constructed using the persistent activation of Akt.

Example 5

Influence of Persistent Activation (Low Activation) of Akt on Shapes of Retinal Blood Vessels In this example, an influence of the persistent activation of Akt on the shapes of the retinal blood vessels in the constitutively active Akt-Mer Tg mouse produced in Example 1 was investigated. Also here, the retina of the constitutively active Akt-Mer Tg mouse in which Akt had been persistently activated was subjected to whole-mount immunostaining and observed.

Methods

To the constitutively active Akt-Mer Tg mouse produced in Example 1, 1 μg/μl 4-OHT was intraperitoneally administered at a dose of 10 μl per day from the fourth day to the sixth day after birth (total dose was 10 μg/day×3 days). This dose was one tenth of the dose in the previous examples. On the seventh day after birth, perfusion fixation from the heart was performed using 4% PFA, and then a retinal cup was produced. Fluorescent immunostaining using an anti PECAM-1 (CD31) antibody was performed, and a flat-mount image of the retina was obtained using AxioObserver (Zeiss). A mouse to which 4-OHT was not administered was used as a control and subjected to the same treatment, and then an image was obtained.

Results

Figure 8:
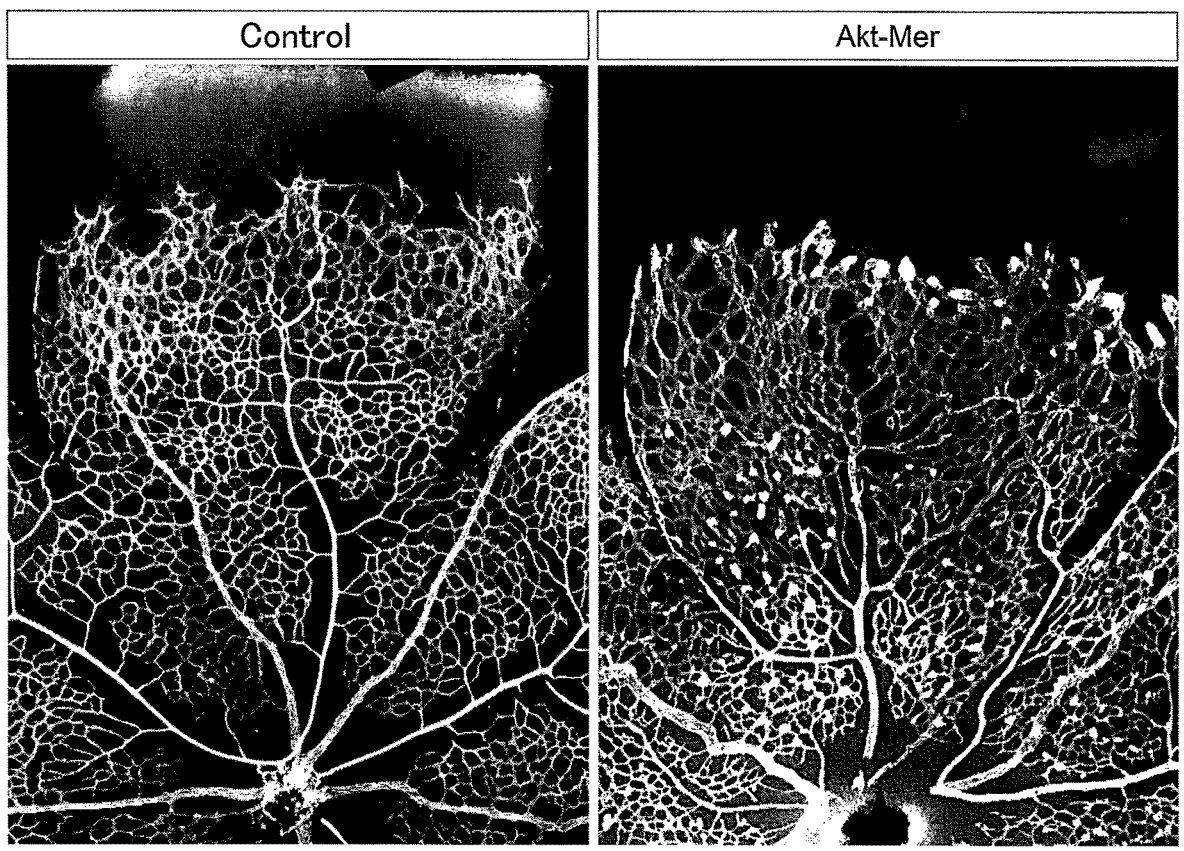
FIG. 8 shows whole-mount immunostaining images of retinas illustrating the results of the examinations in Example 5 that investigated the influence of the persistent activation (low activation) of Akt on the shapes of retinal capillaries.

FIG. 8 shows the results. It is confirmed that, in the persistently active Akt-Mer Tg mouse (Akt-Mer) in which Akt was constitutively activated through the administration of 4-OHT, the formation of microaneurysms was also induced through the administration of low-concentration 4-OHT resulting in the dose which was one tenth of the dose in the previous examples. On the other hand, such a finding was not confirmed in the control. The size and the number of microaneurysms were smaller than those confirmed in the previous examples, and therefore, it is revealed that the degree of severity of an expressed retinal vascular disease can be controlled depending on the degree of Akt activation.

Figure 9:
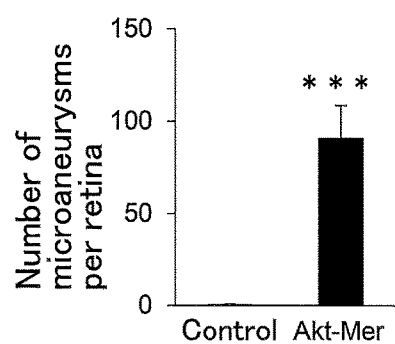
FIG. 9 is a graph showing the measurement results of the number of microaneurysms per retina, illustrating the results of the examinations in Example 5 that investigated the influence of the persistent activation (low activation) of Akt on the shapes of retinal capillaries.

For the purpose of further investigating the retinal vascular morphology in detail, the number of microaneurysms was measured. Specifically, regarding the measurement of the number of microaneurysms, the number of microaneurysms in one retina was manually measured using the flat-mount image of the retina. FIG. 9 shows the results. Microaneurysms were hardly observed in the control, whereas a large number of microaneurysms as many as an average of 90 were observed in one retina in the constitutively active Akt-Mer Tg mouse (Akt-Mer) in which Akt was persistently activated through the administration of 4-OHT.

Figure 10:
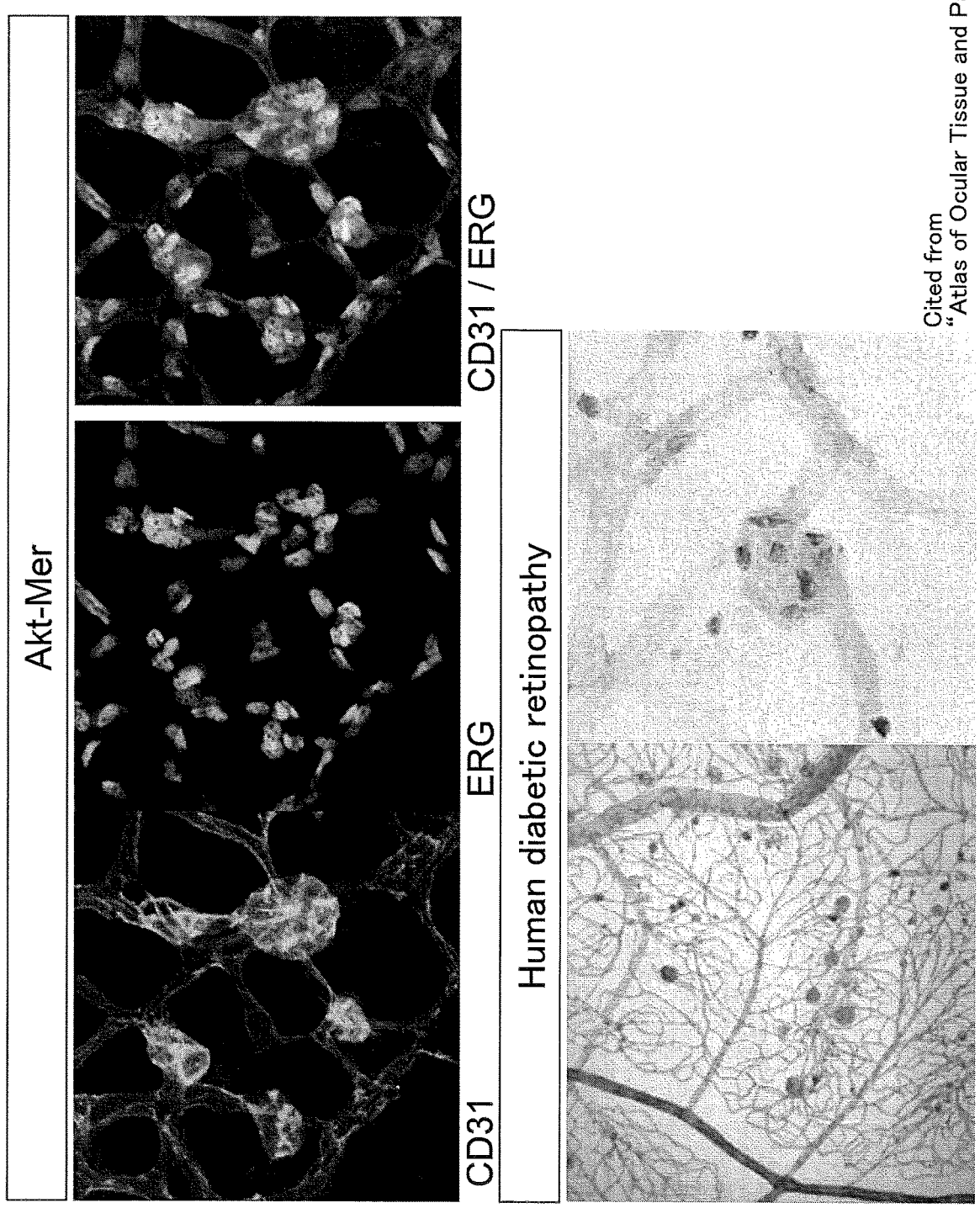
FIG. 10 shows comparison between whole-mount immunostaining images of retinas illustrating the results of the examinations in Example 5 that investigated the influence of the persistent activation (low activation) of Akt on the shapes of retinal capillaries, and pathological specimens of human diabetic retinopathy.

Next, for the purpose of investigating the structures of the microaneurysms in detail, double immunostaining using an anti ERG antibody in addition to an anti PECAM-1 (CD31) antibody was performed, so that vascular endothelial cells were stained using the anti PECAM-1 (CD31) antibody, and the endothelial cell nuclei were stained using the anti ERG antibody. FIG. 10 shows the results. The upper diagrams in FIG. 10 were images obtained using LSM710 (Zeiss). The left diagram indicates the result of staining of microaneurysms in the constitutively active Akt-Mer Tg mouse (Akt-Mer) using the anti PECAM-1 (CD31) antibody, the central diagram indicates the result of staining using the anti ERG antibody, and the right diagram indicates the result of double staining using both of the antibodies, where light-gray immunostained regions were observed. The lower diagrams in FIG. 10 indicate pathological specimens of microaneurysms in human diabetic retinopathy (cited from "Atlas of Ocular Tissue and Pathology") for comparison purposes, and specifically indicate optical micrographs showing specimens of a trypsin-treated vascular network. It can be understood from these results that the vascular varicose structure observed in FIG. 8 and the like included a plurality of endothelial cell nuclei, and was formed of clustered endothelial cells. It can also be understood that this structure is similar to those of the pathological specimens of microaneurysms in human diabetic retinopathy (dark-gray portions observed in vascular varicose structures and the like indicate the clusters of cell nuclei), which have been reported. This reveals that a non-human model animal showing symptoms having high similarity to those of human diabetic retinopathy can be provided using the persistent activation of Akt.

Example 6

Influence of Persistent Activation of Akt on Retinal Vascular Permeability

In this example, an influence of the persistent activation of Akt on the retinal vascular permeability in the constitutively active Akt-Mer Tg mouse produced in Example 1 was investigated. Here, the investigation was performed by observing dye leaking from the retina of the constitutively active Akt-Mer Tg mouse in which Akt had been persistently activated using a stereoscopic microscope.

Methods

To the constitutively active Akt-Mer Tg mouse produced in Example 1, 10 μg/μl 4-OHT was intraperitoneally administered at a dose of 10 μl per day from the fourth day to the sixth day after birth (total dose was 100 ηg/day×3 days). On the seventh day after birth, 20 μl of Evans blue was intraperitoneally administered, and 1 hour after this, perfusion fixation from the heart was performed using 4% PFA, and then, the eyeball was removed. An image of the removed eyeball was obtained using an MZ16F stereoscopic microscope (Leica). A mouse to which 4-OHT was not administered was used as a control and subjected to the same treatment, and then an image was obtained.

Results

Figure 11:
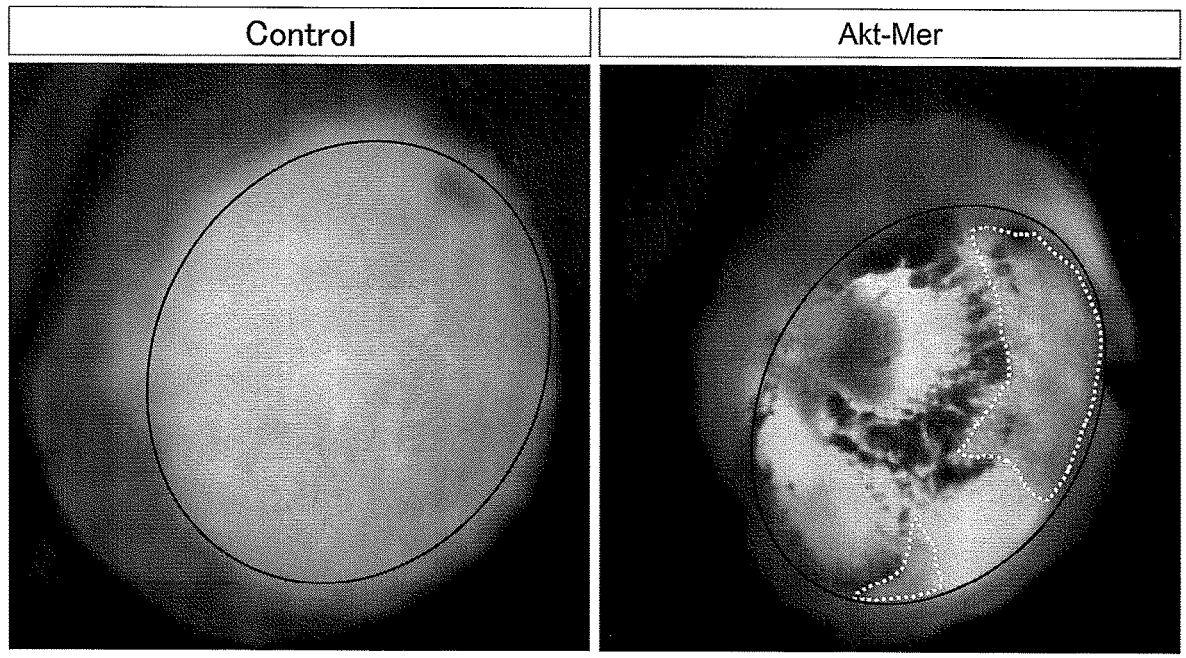
FIG. 11 shows retina cups illustrating the results of the examinations in Example 6 that investigated the influence of the persistent activation of Akt on the vascular permeability in retinas.

FIG. 11 shows the results. In FIG. 11, the inside of the solid line (black) indicates the retina viewed from the vitreous body side, and the inside of the dotted line (white) indicates a region in which the leakage of Evans blue, which is a blue dye, is observed under an optical microscope. It is confirmed from these results that, in the constitutively active Akt-Mer Tg mouse (Akt-Mer) in which Akt was persistently activated through the administration of 4-OHT, the leakage of the dye from the blood vessels was observed, and the vascular permeability was increased. On the other hand, the increase in vascular permeability was not confirmed in the control, and therefore, it can be understood that the increase in vascular permeability is caused by the persistent activation of Akt.

Figure 12:
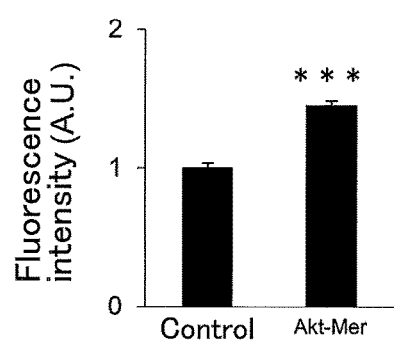
FIG. 12 is a graph showing the measurement results of fluorescence intensity of Evans blue leaking from retinal blood vessels, illustrating the results of the examinations in Example 6 that investigated the influence of the persistent activation of Akt on the vascular permeability in retinas.

Furthermore, for the purpose of evaluating the vascular permeability in a quantitative manner, the fluorescence intensity of Evans blue leaking from the retinal blood vessels was measured using an LSM710 confocal microscope (Zeiss) (***<0.001). FIG. 12 shows the results. It is confirmed from these results that, in the constitutively active Akt-Mer Tg mouse (Akt-Mer) in which Akt was persistently activated through the administration of 4-OHT, the amount of the dye leaking from the blood vessels was significantly larger than that in the control.

Example 7

Influence of Persistent Activation of Akt on Retinal Surface Layer

In this example, an influence of the persistent activation of Akt on the retinal surface layer of the retina in the constitutively active Akt-Mer Tg mouse produced in Example 1 was investigated. Here, the investigation was performed by observing an image of a retinal section obtained from the constitutively active Akt-Mer Tg mouse in which Akt had been persistently activated.

Methods

To the constitutively active Akt-Mer Tg mouse produced in Example 1, 10 μg/μl 4-OHT was intraperitoneally administered at a dose of 10 μl per day from the fourth day to the sixth day after birth (total dose was 100 μg/day×3 days). On the seventh day after birth, perfusion fixation from the heart was performed using 4% PFA. The eyeball was removed, and then a retinal cryosection was produced. The nuclei were visualized through Hoechst staining, and an image was obtained using a microscope (Zeiss). A mouse to which 4-OHT was not administered was used as a control and subjected to the same treatment, and then an image was obtained.

Results

Figure 13:
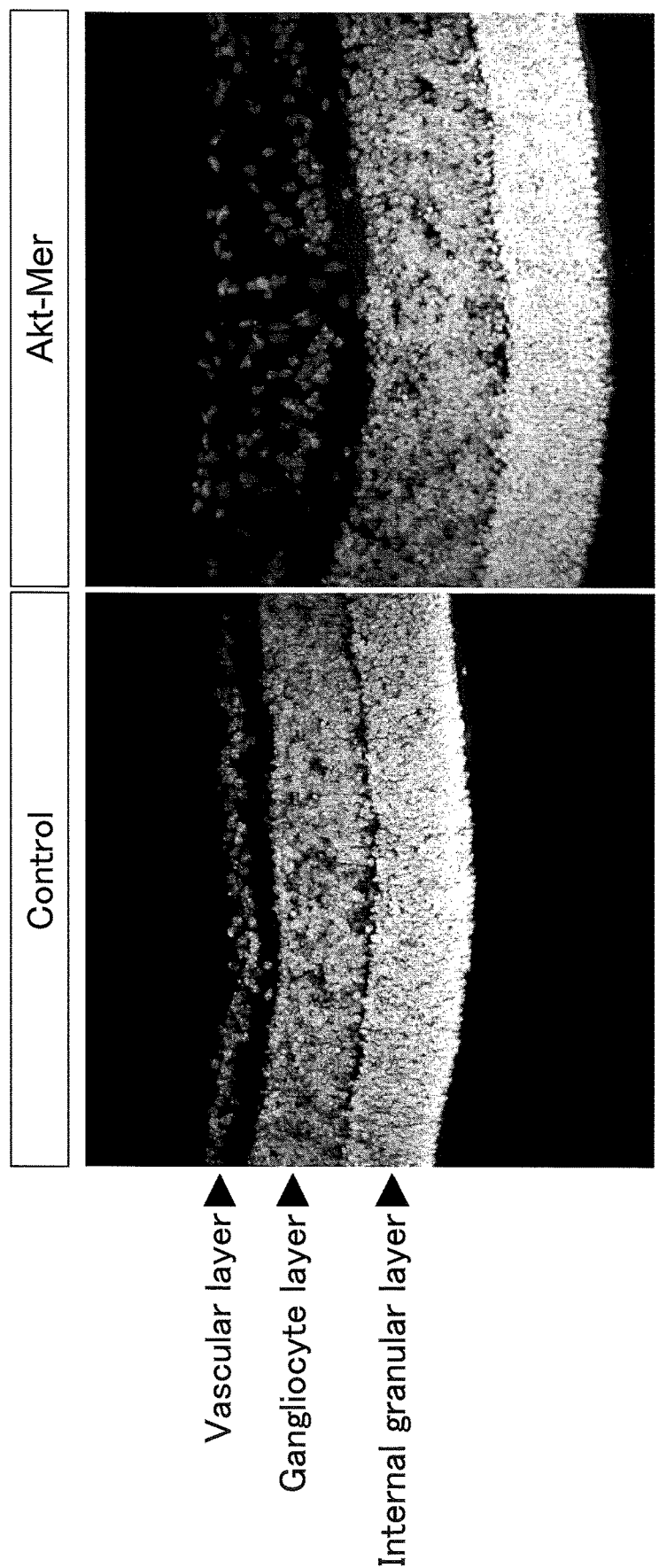
FIG. 13 shows nucleo-staining in cryosections of retinas illustrating the results of the examinations in Example 7 that investigated the influence of the persistent activation of Akt on retinal surface layers.

FIG. 13 shows the results. In the constitutively active Akt-Mer Tg mouse (Akt-Mer) in which Akt was persistently activated through the administration of 4-OHT, the overall retina, particularly the surface layer in which a vascular layer is present was significantly swollen. On the other hand, such a finding was not confirmed in the control, and therefore, it can be understood that the swollen surface layer is caused by the persistent activation of Akt.

It is confirmed from the results of Examples 6 and 7 that retinal edema occurs due to an increase in retinal vascular permeability caused by the persistent activation of Akt. Such retinal edema is found in human diabetic retinopathy irrespective of the degree of severity, and such a finding has hardly been confirmed in model animals that have been reported until the present time.

Example 8

Analysis of Factors of Abnormal Vascular Morphology Caused by Persistent Activation of Akt (Vascular Endothelial Cells and Astrocytes)

In this example, factors in the abnormal vascular morphology caused by the persistent activation of Akt, which is confirmed in the previous examples, was investigated. Here, the retina of the constitutively active Akt-Mer Tg mouse in which Akt had been persistently activated was subjected to whole-mount immunostaining and observed.

Methods

To the constitutively active Akt-Mer Tg mouse produced in Example 1, 10 μg/μl 4-OHT was intraperitoneally administered at a dose of 10 μl per day from the fourth day to the sixth day after birth (total dose was 100 μg/day×3 days). On the seventh day after birth, perfusion fixation from the heart was performed using 4% PFA, and then a retinal cup was produced. Fluorescent immunostaining using an anti PECAM-1 (CD31) antibody and an anti GFAP antibody was performed, and a flat-mount image of the retina was obtained using LSM710 (Zeiss).

Results

Figure 14:
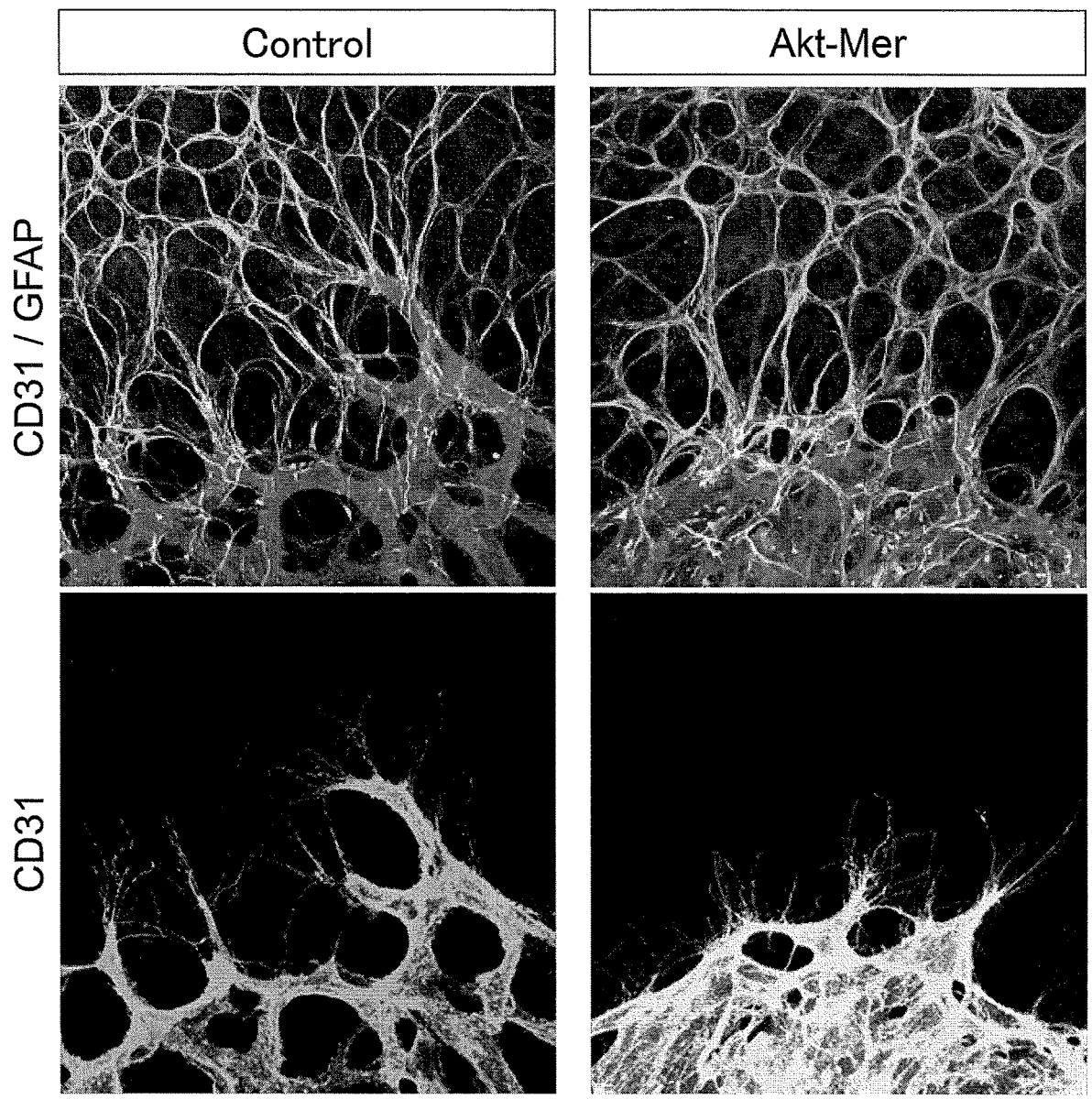
FIG. 14 shows whole-mount immunostaining images of retinas illustrating the results of the examinations in Example 8 that analyzed the factors (vascular endothelial cells and astrocytes) in abnormal vascular morphology caused by the persistent activation of Akt.

FIG. 14 shows the results. The upper diagrams in FIG. 14 indicate the results of double staining using the anti PECAM-1 (CD31) antibody and the anti GFAP antibody, and the lower diagrams indicate the results of staining using the anti PECAM-1 (CD31) antibody. It is confirmed from these results that, in the retinal vascular network of the constitutively active Akt-Mer Tg mouse (Akt-Mer) in which Akt had been persistently activated, the morphology of the astrocytes (GFAP) acting as a scaffold of vascular extension was not different from that in the control. Therefore, it can be understood that the abnormal vascular structure caused by the persistent activation of Akt, which is confirmed in the previous examples, is caused by abnormal endothelial cells.

Example 9

Analysis of Factors of Abnormal Vascular Morphology Caused by Persistent Activation of Akt (VEGF Expression Level)

In this example, factors in the abnormal vascular morphology caused by the persistent activation of Akt, which is confirmed in the previous examples, was investigated. Here, the VEGF expression level in the retina of the constitutively active Akt-Mer Tg mouse in which Akt had been persistently activated was measured.

Methods

To the constitutively active Akt-Mer Tg mouse produced in Example 1, 10 μg/μl 4-OHT was intraperitoneally administered at a dose of 10 μl per day from the fourth day to the sixth day after birth (total dose was 100 μg/day×3 days). On the seventh day after birth, RNAs were extracted from the retina removed without performing perfusion fixation. DNAs were synthesized through reverse transcription, and the expression of the VEGF gene was analyzed through a quantitative PCR. At this time, the expression of β-actin as a house-keeping gene was also analyzed. A mouse to which 4-OHT was not administered was used as a control and subjected to the same treatment, followed by the analysis.

The following are the sequences of primers used here.

```
For Vegf:
                                (Sequence ID No. 24)
5'-tacacaattcagagcgatgtgtggt-3'

(Sequence ID No. 25)
5'-ctggttcctccaatgggatatcttc-3'

For β-actin:
                                (Sequence ID No. 26)
5'-ggctgtaattcccctccatcg-3'

(Sequence ID No. 27)
5'-ccagttggtaacaatgccatgt-3'
```

Results

Figure 15:
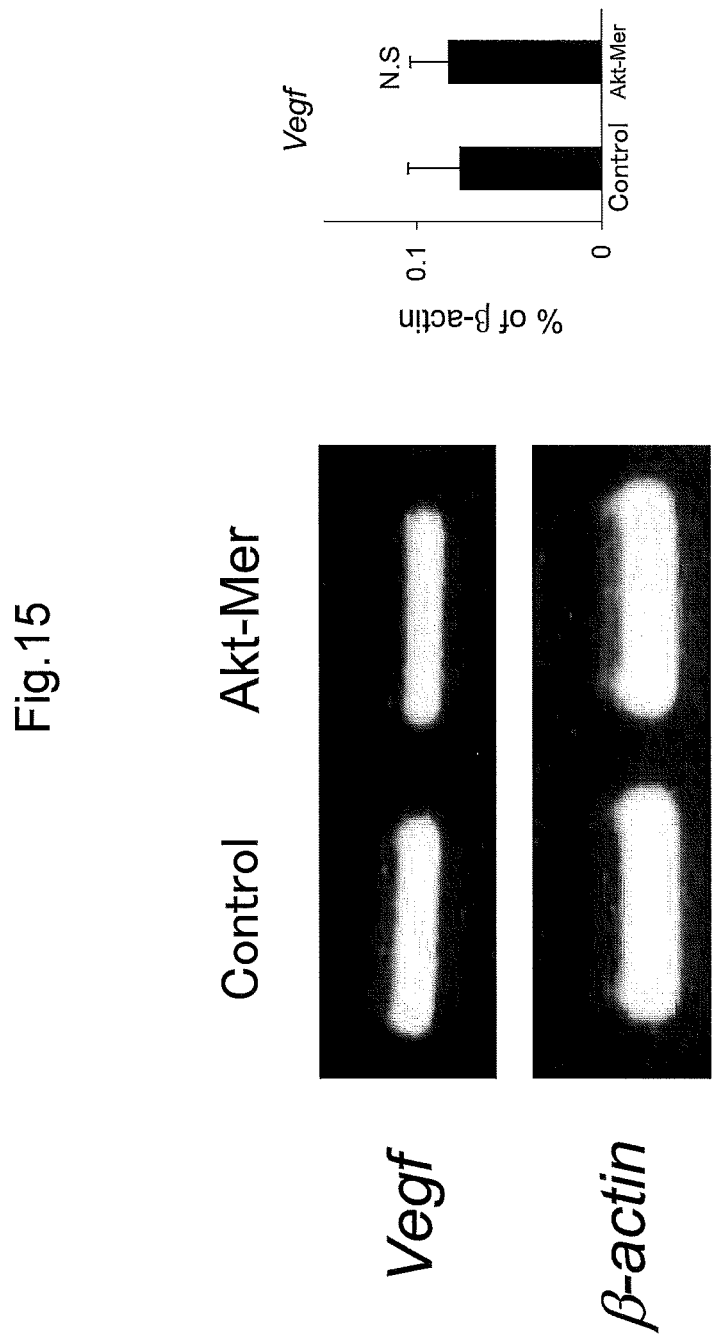
FIG. 15 shows Western bolts and a graph illustrating the results of the examinations in Example 9 that analyzed the factor (VEGF expression level) in abnormal vascular morphology caused by the persistent activation of Akt.

FIG. 15 shows the results. Graphs indicating the results of the measurement of the VEGF gene expression level are shown. In the constitutively active Akt-Mer Tg mouse (Akt-Mer) in which Akt had been persistently activated, the expression of the VEGF gene was not different from that in the control, and therefore, it can be understood that the abnormal vascular morphology is not a secondary change induced by excessive VEGF.

Example 10

Influence of Long-Term Persistent Activation of Akt on Retina

In this example, an influence of the long-term constitutive activation of Aid on the shapes of the retinal capillaries in the persistently active Akt-Mer Tg mouse produced in Example 1 was investigated. Here, the retina of the constitutively active Akt-Mer Tg mouse in which Akt had been activated for a longer period of time than those in the previous exampels was subjected to whole-mount immunostaining and observed.

Methods

To the constitutively active Akt-Mer Tg mouse produced in Example 1, 1 μg/μl 4-OHT was intraperitoneally administered at a dose of 10 μl per day from the fourth day to the sixth day after birth (total dose was 100 μg/day×3 days). On the fourteenth day after birth, fluorescent immunostaining using an anti PECAM-1 (CD31) antibody was performed, and a flat-mount image of the retina was obtained. The image obtained using LSM710 (Zeiss) was colored in different depths depending on the depth in a Z direction. A mouse to which 4-OHT was not administered was used as a control and subjected to the same treatment, and then an image was obtained.

Results

Figure 16:
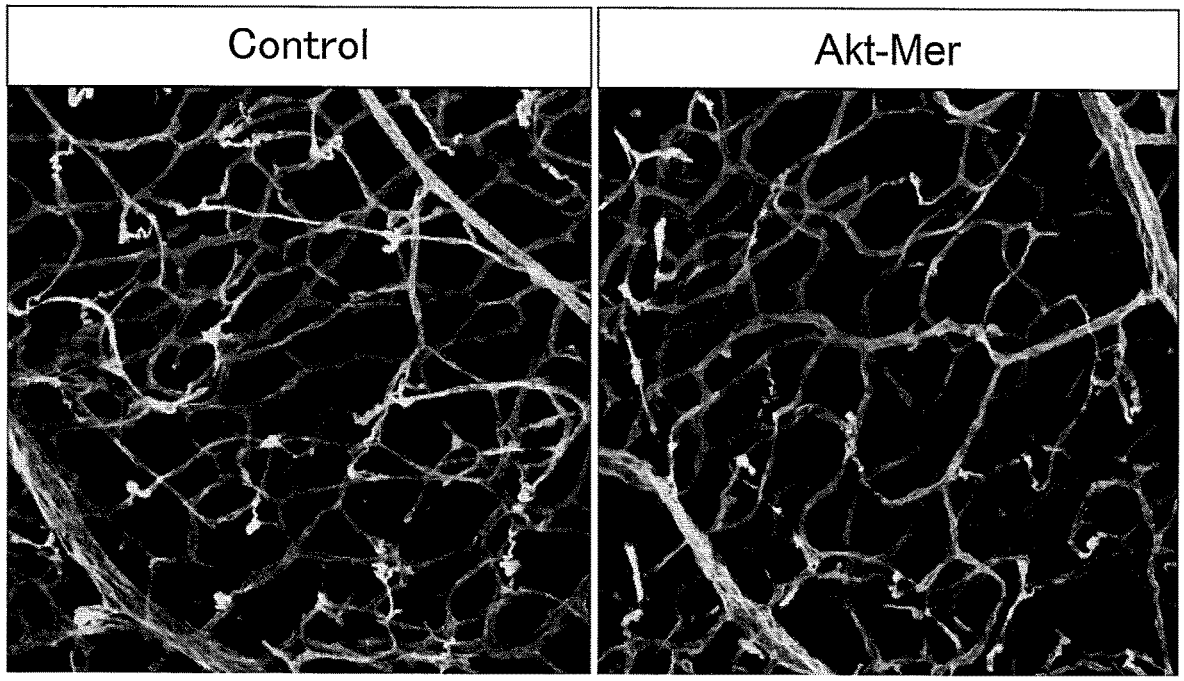
FIG. 16 shows whole-mount immunostaining images of retinas illustrating the results of the examinations in Example 10 that investigated the influence of the long-term persistent activation of Akt on retinas.

FIG. 16 shows the results. On the fourteenth day after birth, in the constitutively active Akt-Mer Tg mouse (Akt-Mer) in which Aid had been persistently activated, the expansion of the retinal vascular diameter and the decrease in a vascular density were confirmed.

Example 11

Influences of Activation Degree and Activation Period of Persistent Activation of Akt on Retina In this example, influences of the activation degree and activation period of the persistent activation of Akt on the morphology of the retinal capillaries in the constitutively active Akt-Mer Tg mouse produced in Example 1 was investigated. Here, the activation degree and activation period of the persistent activation of Akt were controlled by changing the dose and administration period of 4-OHT, and then the retina was subjected to whole-mount immunostaining and observed to confirm changes in the retinal vascular morphology of the constitutively active Akt-Mer Tg mouse.

Methods

4-OHT was administered to the constitutively active Akt-Mer Tg mouse produced in Example 1 in accordance with any of the following procedures: 10 μg/μl 4-OHT was intraperitoneally administered at a dose of 10 μl per day from the fourth day to the sixth day after birth (total dose was 100 μg/day×3 days); 1 μg/μl 4-OHT was intraperitoneally administered at a dose of 10 μl per day from the fourth day to the sixth day after birth (total dose was 10 μg/day×3 days); or 10 μg/μl 4-OHT was intraperitoneally administered at a dose of 10 μl per day only on the fourth day after birth (total dose was 100 μg/day×1 day). On the seventh day after birth, perfusion fixation from the heart was performed using 4% PFA, and then a retinal cup was produced. Subsequently, fluorescent immunostaining using an anti PECAM-1 (CD31) antibody was performed. Flat-mount images of the retinas were obtained using AxioObserver (Zeiss), and the obtained images were compared between the groups. A mouse to which 4-OHT was not administered was used as a control and subjected to the same treatment, and then an image was obtained.

Results

Figure 17:
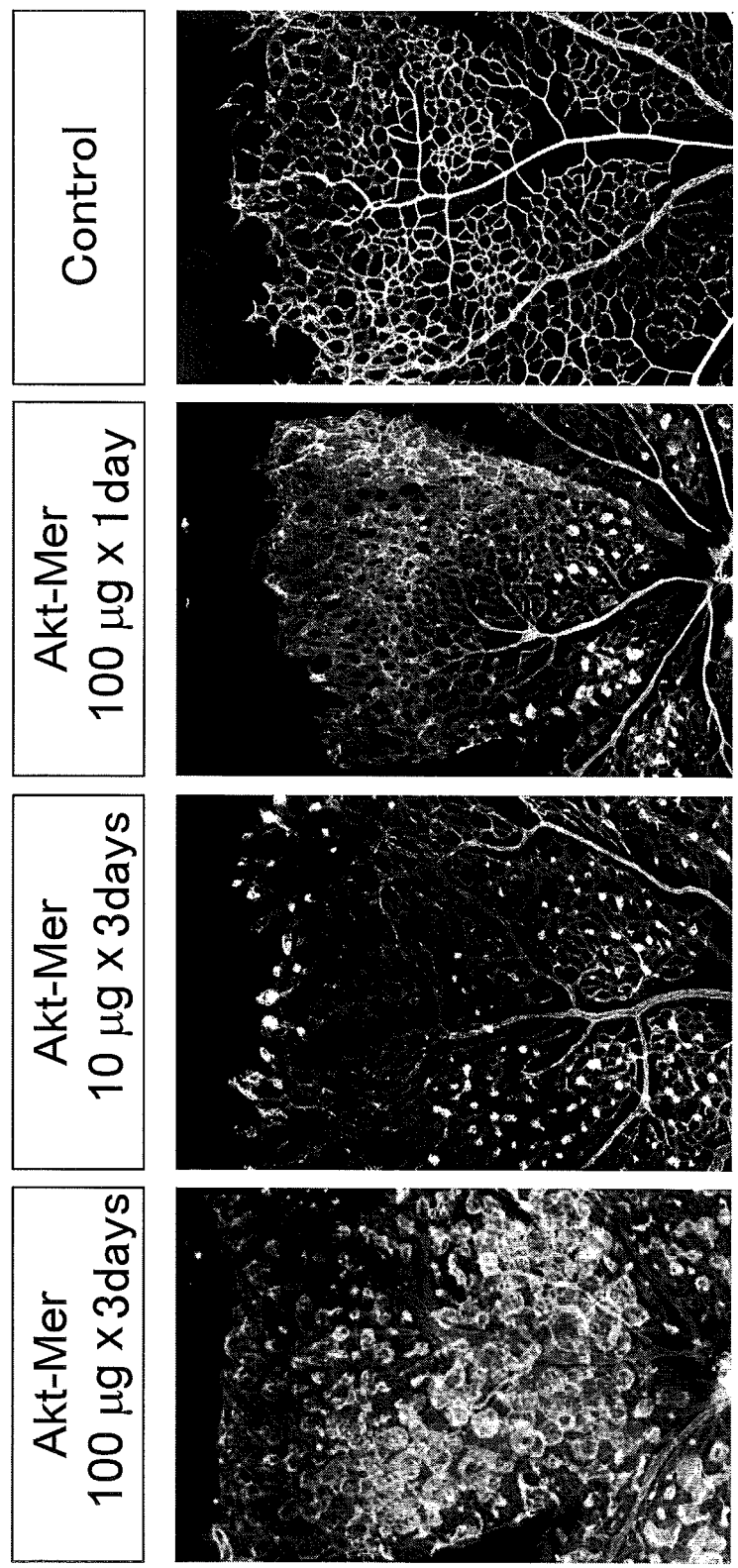
FIG. 17 shows whole-mount immunostaining images of retinas illustrating the results of the examinations in Example 11 that investigated the influences of the activation level and activation period of the persistent activation of Akt on retinas.

FIG. 17 shows the results. It is confirmed that the level of microaneurysms varied depending on the dose and the administration period of 4-OHT.

Figure 18:
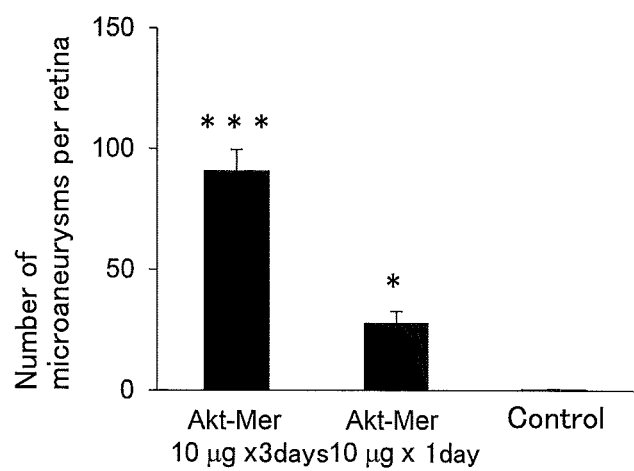
FIG. 18 is a graph showing the measurement results of the number of microaneurysms per retina, illustrating the results of the examinations in Example 11 that investigated the influences of the activation level and activation period of the persistent activation of Akt on retinas.

Furthermore, for the purpose of further investigating the retinal vascular morphology in detail, the number of microaneurysms was measured. Specifically, regarding the measurement of the number of microaneurysms, the number of microaneurysms in one retina was manually measured using the flat-mount image of the retina. FIG. 18 shows the results. It should be noted that, the results obtained from the group to which 10 μg/μl 4-OHT was intraperitoneally administered at a dose of 10 μl per day from the fourth day to the sixth day after birth (total dose was 100 μg/day×3 days) were not used in the quantification because aneurysms were fused, and the number thereof could not be measured.

It can be understood from the results above that the morphology of the retinal capillaries changes depending on the activation degree and the activation period of the persistent activation of Akt, desired retinal vascular morphology can be obtained based on an activation manner including the activation degree, the activation period, and the like of the persistent activation of Akt, and the degree of severity of a retinal vascular disease can be thus controlled.

Example 12

Use in Screening of Drug for Treating or Preventing Retinal Vascular Disease

In this example, an influence of an Akt inhibitor on the abnormal morphology of the retinal capillaries caused by the persistent activation of Aid in the constitutively active Akt-Mer Tg mouse produced in Example 1 was investigated. Here, the retina was subjected to whole-mount immunostaining and observed to confirm changes in the retinal vascular morphology of the constitutively active Akt-Mer Tg mouse caused by the application of an Akt inhibitor.

Methods

To the constitutively active Akt-Mer Tg mouse produced in Example 1, 10 μg/μl 4-OHT was intraperitoneally administered at a dose of 10 μl per day from the fourth day to the sixth day after birth (total dose was 100 μg/day×3 days). In addition, any of mitomycin C, an Akt inhibitor 1 (Tricirib-ine), and an Akt inhibitor 2 (GSK), which has a cell proliferation inhibition effect, was intraperitoneally administered 24 hours before the retina was collected. In the group to which a drug was administered and the group (Akt-Mer) to which no drug was administered, perfusion fixation from the heart was performed using 4% PFA, the retina was collected, and then a retinal cup was produced. The collected retina was subjected to fluorescent immunostaining using an anti PECAM-1 antibody. Flat-mount images of the retinas were obtained using AxioObserver (Zeiss), and the obtained images were compared between the groups. A mouse to which 4-OHT was not administered was used as a control and subjected to the same treatment, and then an image was obtained.

Results

Figure 19:
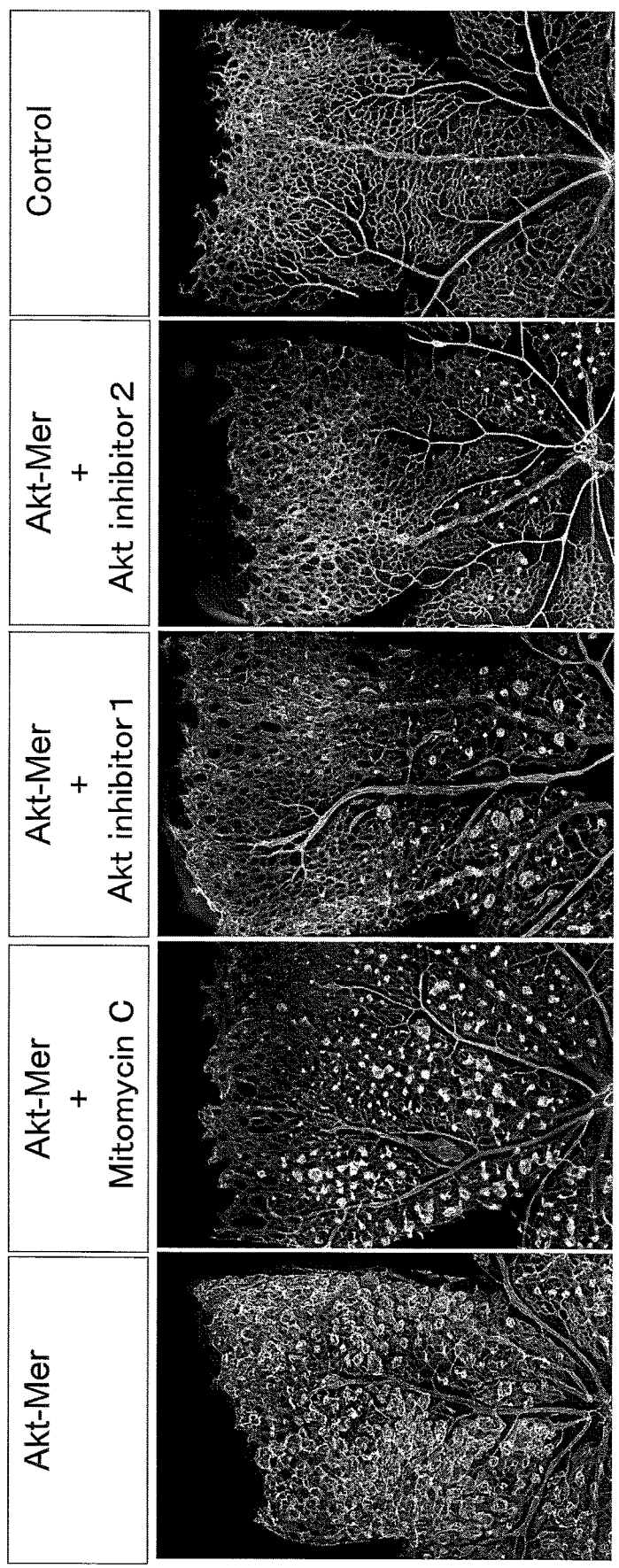
FIG. 19 shows whole-mount immunostaining images of retinas after the administration of drugs, illustrating the results of the examinations in Example 12 that used drugs for treating or preventing a retinal vascular disease in screening.

FIG. 19 shows the results. Microaneurysms formed through the persistent activation of Akt decreased due to the administration of the Akt inhibitor, and the vascular expansion caused by the persistent activation of Akt also disappeared. Therefore, it can be understood that the constitutively active Akt-Mer Tg mouse (Akt-Mer) model in which Akt is persistently activated can be used to determine the retinal vascular disease treatment effect of an administered drug.

INDUSTRIAL APPLICABILITY

The present disclosure can be used in the medical field, the biochemical field, and the like. In particular, the present disclosure can be used to develop a method for treating, preventing, or diagnosing a retinal vascular disease such as diabetic retinopathy and diabetic nephropathy, and to analyze the pathology thereof.

The invention claimed is:

1. A transgenic mouse model of a retinal vascular disease, wherein the mouse model has a genome comprising a nucleic acid sequence encoding a constitutively active Akt mutant protein:
 (i) comprising an E40K or E17K substitution mutation; or
 (ii) in which a Plekstrin homology (PH) domain at the N-terminus has been replaced with a myristoylation signal sequence, wherein the mouse model shows at least one symptom selected from the group consisting of retinal edema, retinal hemorrhage, a retinal microaneurysm, and retinal vascular expansion.

2. The transgenic mouse model of a retinal vascular disease according to claim 1, wherein the mouse model has a genome comprising a nucleic acid sequence encoding a constitutively active Akt mutant protein in which a PH domain at the N-terminus has been replaced with a myristoylation signal sequence.

3. The transgenic mouse model of a retinal vascular disease according to claim 1, wherein expression of the constitutively active Akt mutant protein of (i) or (ii) is under the control of a Cre-LoxP system.

4. The transgenic mouse model of a retinal vascular disease according to claim 1, wherein the retinal vascular disease is diabetic retinopathy.

5. A method for screening a test substance for treating a retinal vascular disease, comprising:
 a) administering a test substance to the transgenic mouse model of a retinal vascular disease according to claim 1, and
 b) determining the effect of the test substance on the at least one symptom, wherein a decrease in the at least one symptom as compared to a control indicates the test substance treats retinal vascular disease.

6. A method for producing a transgenic mouse model of a retinal vascular disease, the method comprising:
 a) introducing DNA into a fertilized mouse egg, wherein the DNA encodes: (i) a constitutively active Akt mutant protein comprising an E40K or E17K substitution mutation; or (ii) a constitutively active Akt mutant protein in which a Plekstrin homology (PH) domain at the N-terminus has been replaced with a myristoylation signal sequence; and
 b) implanting the fertilized mouse egg obtained in step a) into a recipient embryo such that a transgenic mouse model of a retinal vascular disease is obtained,
 wherein the mouse model has a genome comprising a nucleic acid sequence encoding: (i) a constitutively active Akt mutant protein comprising an E40K or E17K substitution mutation; or (ii) a constitutively active Akt mutant protein in which a PH domain at the N-terminus has been replaced with a myristoylation signal sequence, wherein the mouse model shows at least one symptom selected from the group consisting of retinal edema, retinal hemorrhage, a retinal microaneurysm, and retinal vascular expansion.

7. The method for producing a transgenic mouse model of a retinal vascular disease according to claim 6, wherein the mouse model has a genome comprising a nucleic acid sequence encoding a constitutively active Akt mutant protein in which a PH domain at the N-terminus has been replaced with a myristoylation signal sequence, and expression of the constitutively active Akt mutant protein is controlled using 4-hydroxytamoxifen.

8. The method for producing a transgenic mouse model of a retinal vascular disease according to claim 7, wherein the 4-hydroxytamoxifen is administered at a dose of 5 to 50 µg/g weight/day during a desired period between the first day and the fourteenth day after birth.

9. The method for producing a transgenic mouse model of a retinal vascular disease according to claim 6, wherein expression of the constitutively active Akt mutant protein is under the control of a Cre-loxP system.

10. A transgenic mouse whose genome comprises a nucleic acid sequence encoding a constitutively active Akt mutant protein:
 (i) comprising an E40K or E17K substitution mutation; or
 (ii) in which a Plekstrin homology (PH) domain at the N-terminus has been replaced with a myristoylation signal sequence,
 wherein the mouse is capable of developing at least one symptom selected from the group consisting of retinal edema, retinal hemorrhage, a retinal microaneurysm, and retinal vascular expansion after inducing expression of the constitutively active Akt mutant protein.

11. A method for screening a test substance for preventing retinal vascular disease, comprising:
 a) administering a test substance to the transgenic mouse according to claim 10,
 b) inducing expression of the constitutively active Akt mutant protein; and
 c) determining the effect of the test substance on preventing the at least one symptom after inducing expression of the constitutively active Alit mutant protein, wherein a delay in progress or decrease in the at least one symptom as compared to a control indicates the test substance prevents retinal vascular disease.

* * * * *